US012683021B2

(12) United States Patent
Kamath et al.

(10) Patent No.: US 12,683,021 B2
(45) Date of Patent: Jul. 14, 2026

(54) METHODS AND SYSTEMS FOR PROMOTING GLUCOSE MANAGEMENT

(71) Applicant: DexCom, Inc., San Diego, CA (US)

(72) Inventors: Apurv Ullas Kamath, San Diego, CA (US); Jack Pryor, Ladera Ranch, CA (US); Alexandra Lynn Carlton, San Marcos, CA (US); Kristin Koenekamp Cote, Walnut Creek, CA (US); Leif N. Bowman, San Diego, CA (US); Michael Robert Mensinger, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 1881 days.

(21) Appl. No.: 16/706,425

(22) Filed: Dec. 6, 2019

(65) Prior Publication Data

US 2020/0114078 A1 Apr. 16, 2020

Related U.S. Application Data

(63) Continuation of application No. 14/971,886, filed on Dec. 16, 2015, now Pat. No. 10,537,678, which is a
(Continued)

(51) Int. Cl.
*A61B 5/145* (2006.01)
*A61B 5/00* (2006.01)
(Continued)

(52) U.S. Cl.
CPC ........... *G16H 40/67* (2018.01); *A61B 5/0004* (2013.01); *A61B 5/14532* (2013.01);
(Continued)

(58) Field of Classification Search
CPC ............ A61B 5/14532; A61B 5/14546; A61B 5/4833; A61B 5/743; A61B 5/744;
(Continued)

(56) References Cited

U.S. PATENT DOCUMENTS

| 598,724 A | 2/1898 | Barker |
| 623,803 A | 4/1899 | Morrow |

(Continued)

FOREIGN PATENT DOCUMENTS

| EP | 0098592 A2 | 1/1984 |
| EP | 0127958 A2 | 12/1984 |

(Continued)

OTHER PUBLICATIONS

US 7,530,950 B2, 05/2009, Brister et al. (withdrawn)
(Continued)

*Primary Examiner* — Jacqueline Cheng
*Assistant Examiner* — Tho Q Tran
(74) *Attorney, Agent, or Firm* — Patterson + Sheridan, LLP

(57) ABSTRACT

Methods and systems for encouraging interactions with a glucose monitoring system include incrementing a score and/or providing a reward based on a variety of different interactions with the glucose monitoring system. The interactions which improve the score may include initiating or changing displays, downloading data, setting operational parameters and other interactions that are independent of a user's glucose measurements. Encouraging these interactions can enhance success in maintaining healthy glucose concentrations.

5 Claims, 16 Drawing Sheets

Related U.S. Application Data continuation of application No. 14/144,489, filed on Dec. 30, 2013, now Pat. No. 10,610,642, which is a continuation of application No. 12/748,069, filed on Mar. 26, 2010, now Pat. No. 9,446,194.

(60) Provisional application No. 61/164,326, filed on Mar. 27, 2009.

(51) Int. Cl.

| | |
|---|---|
| *A61B 5/1495* | (2006.01) |
| *A61M 5/142* | (2006.01) |
| *A61M 5/172* | (2006.01) |
| *G16H 40/63* | (2018.01) |
| *G16H 40/67* | (2018.01) |
| *G16H 20/17* | (2018.01) |
| *G16H 50/50* | (2018.01) |

(52) U.S. Cl.

CPC ........ *A61B 5/14546* (2013.01); *A61B 5/1495* (2013.01); *A61B 5/4833* (2013.01); *A61B 5/725* (2013.01); *A61B 5/743* (2013.01); *A61B 5/744* (2013.01); *A61B 5/746* (2013.01); *A61B 5/7475* (2013.01); *A61M 5/142* (2013.01); *A61M 5/1723* (2013.01); *G16H 40/63* (2018.01); *A61M 2205/3303* (2013.01); *A61M 2205/502* (2013.01); *A61M 2205/581* (2013.01); *A61M 2205/582* (2013.01); *A61M 2205/583* (2013.01); *A61M 2230/06* (2013.01); *A61M 2230/201* (2013.01); *A61M 2230/63* (2013.01); *G16H 20/17* (2018.01); *G16H 50/50* (2018.01); *Y02A 90/10* (2018.01)

(58) Field of Classification Search

CPC .... A61B 5/746; A61B 5/7475; A61M 5/1723; A61M 2205/3303; A61M 2205/502; A61M 2205/581; A61M 2205/582; A61M 2205/583; A61M 2230/201

See application file for complete search history.

(56) References Cited

U.S. PATENT DOCUMENTS

| | | | |
|---|---|---|---|
| 3,210,578 | A | 10/1965 | Sherer |
| 3,219,533 | A | 11/1965 | Mullins |
| 3,780,727 | A | 12/1973 | King |
| 3,898,984 | A | 8/1975 | Mandel et al. |
| 3,929,971 | A | 12/1975 | Roy |
| 3,943,918 | A | 3/1976 | Lewis |
| 3,979,274 | A | 9/1976 | Newman |
| 4,076,656 | A | 2/1978 | White et al. |
| 4,240,889 | A | 12/1980 | Yoda et al. |
| 4,253,469 | A | 3/1981 | Aslan |
| 4,403,984 | A | 9/1983 | Ash et al. |
| 4,415,666 | A | 11/1983 | D'Orazio et al. |
| 4,431,004 | A | 2/1984 | Bessman et al. |
| 4,436,094 | A | 3/1984 | Cerami |
| 4,454,295 | A | 6/1984 | Wittmann et al. |
| 4,494,950 | A | 1/1985 | Fischell |
| 4,506,680 | A | 3/1985 | Stokes |
| RE31,916 | E | 6/1985 | Oswin et al. |
| 4,554,927 | A | 11/1985 | Fussell |
| 4,577,642 | A | 3/1986 | Stokes |
| RE32,361 | E | 2/1987 | Duggan |
| 4,655,880 | A | 4/1987 | Liu |
| 4,671,288 | A | 6/1987 | Gough |
| 4,680,268 | A | 7/1987 | Clark, Jr. |
| 4,703,756 | A | 11/1987 | Gough et al. |
| 4,711,251 | A | 12/1987 | Stokes |
| 4,721,677 | A | 1/1988 | Clark, Jr. |
| 4,731,726 | A | 3/1988 | Allen, III |
| 4,757,022 | A | 7/1988 | Shults et al. |
| 4,759,828 | A | 7/1988 | Young et al. |
| 4,781,798 | A | 11/1988 | Gough |
| 4,805,625 | A | 2/1989 | Wyler |
| 4,849,458 | A | 7/1989 | Reed et al. |
| 4,852,573 | A | 8/1989 | Kennedy |
| 4,858,615 | A | 8/1989 | Meinema |
| 4,883,057 | A | 11/1989 | Broderick |
| 4,890,620 | A | 1/1990 | Gough |
| 4,890,621 | A | 1/1990 | Hakky |
| 4,919,141 | A | 4/1990 | Zier et al. |
| 4,927,516 | A | 5/1990 | Yamaguchi et al. |
| 4,944,299 | A | 7/1990 | Silvian |
| 4,953,552 | A | 9/1990 | Demarzo |
| 4,975,636 | A | 12/1990 | Desautels |
| 4,986,671 | A | 1/1991 | Sun et al. |
| 4,988,341 | A | 1/1991 | Columbus et al. |
| 4,994,167 | A | 2/1991 | Shults et al. |
| 5,002,572 | A | 3/1991 | Picha |
| 5,030,333 | A | 7/1991 | Clark, Jr. |
| 5,050,612 | A | 9/1991 | Matsumura |
| 5,068,536 | A | 11/1991 | Rosenthal |
| 5,077,476 | A | 12/1991 | Rosenthal |
| 5,097,834 | A | 3/1992 | Skrabal |
| 5,101,814 | A | 4/1992 | Palti |
| 5,108,819 | A | 4/1992 | Heller et al. |
| 5,137,028 | A | 8/1992 | Nishimura |
| 5,140,985 | A | 8/1992 | Schroeder et al. |
| 5,160,418 | A | 11/1992 | Mullen |
| 5,165,407 | A | 11/1992 | Wilson et al. |
| 5,190,041 | A | 3/1993 | Palti |
| 5,198,771 | A | 3/1993 | Fidler et al. |
| 5,208,147 | A | 5/1993 | Kagenow et al. |
| 5,243,983 | A | 9/1993 | Tarr et al. |
| 5,264,104 | A | 11/1993 | Gregg et al. |
| 5,266,179 | A | 11/1993 | Nankai et al. |
| 5,269,891 | A | 12/1993 | Colin |
| 5,282,848 | A | 2/1994 | Schmitt |
| 5,287,753 | A | 2/1994 | Routh et al. |
| 5,299,571 | A | 4/1994 | Mastrototaro |
| 5,307,263 | A | 4/1994 | Brown |
| 5,316,008 | A | 5/1994 | Suga et al. |
| 5,324,322 | A | 6/1994 | Grill, Jr. et al. |
| 5,330,634 | A | 7/1994 | Wong et al. |
| 5,331,555 | A | 7/1994 | Hashimoto et al. |
| 5,337,747 | A | 8/1994 | Neftel |
| 5,368,224 | A | 11/1994 | Richardson et al. |
| 5,372,133 | A | 12/1994 | Hogen Esch |
| 5,376,070 | A | 12/1994 | Purvis et al. |
| 5,390,671 | A | 2/1995 | Lord et al. |
| 5,391,250 | A | 2/1995 | Cheney, II et al. |
| 5,411,866 | A | 5/1995 | Luong et al. |
| 5,429,735 | A | 7/1995 | Johnson et al. |
| 5,431,160 | A | 7/1995 | Wilkins |
| 5,434,412 | A | 7/1995 | Sodickson et al. |
| 5,462,051 | A | 10/1995 | Oka et al. |
| 5,462,064 | A | 10/1995 | D'Angelo et al. |
| 5,474,552 | A | 12/1995 | Palti |
| 5,494,562 | A | 2/1996 | Maley et al. |
| 5,497,772 | A | 3/1996 | Schulman et al. |
| 5,502,396 | A | 3/1996 | Desarzens et al. |
| 5,507,288 | A | 4/1996 | Bocker et al. |
| 5,513,636 | A | 5/1996 | Palti |
| 5,518,601 | A | 5/1996 | Foos et al. |
| 5,531,878 | A | 7/1996 | Vadgama et al. |
| 5,540,828 | A | 7/1996 | Yacynych |
| 5,553,616 | A | 9/1996 | Ham et al. |
| 5,568,806 | A | 10/1996 | Cheney, II et al. |
| 5,569,186 | A | 10/1996 | Lord et al. |
| 5,582,184 | A | 12/1996 | Erickson et al. |
| 5,584,813 | A | 12/1996 | Livingston et al. |
| 5,586,553 | A | 12/1996 | Halili et al. |
| 5,653,863 | A | 8/1997 | Genshaw et al. |
| 5,660,163 | A | 8/1997 | Schulman et al. |
| 5,678,571 | A | 10/1997 | Brown |
| 5,695,623 | A | 12/1997 | Michel et al. |
| 5,711,861 | A | 1/1998 | Ward et al. |
| 5,730,654 | A | 3/1998 | Brown |
| 5,743,262 | A | 4/1998 | Lepper, Jr. et al. |
| 5,749,907 | A | 5/1998 | Mann |

(56)  References Cited

U.S. PATENT DOCUMENTS

| | | | |
|---|---|---|---|
| 5,781,455 A | 7/1998 | Hyodo |
| 5,791,344 A | 8/1998 | Schulman et al. |
| 5,795,774 A | 8/1998 | Matsumoto et al. |
| 5,800,420 A | 9/1998 | Gross et al. |
| 5,806,517 A | 9/1998 | Gerhardt et al. |
| 5,807,375 A | 9/1998 | Gross et al. |
| 5,814,599 A | 9/1998 | Mitragotri et al. |
| 5,822,715 A | 10/1998 | Worthington et al. |
| 5,836,887 A | 11/1998 | Oka et al. |
| 5,836,989 A | 11/1998 | Shelton |
| 5,861,019 A | 1/1999 | Sun et al. |
| 5,871,514 A | 2/1999 | Wiklund et al. |
| 5,882,494 A | 3/1999 | Van Antwerp |
| 5,897,578 A | 4/1999 | Wiklund et al. |
| 5,899,855 A | 5/1999 | Brown |
| 5,904,708 A | 5/1999 | Goedeke |
| 5,913,998 A | 6/1999 | Butler et al. |
| 5,914,026 A | 6/1999 | Blubaugh, Jr. et al. |
| 5,919,215 A | 7/1999 | Wiklund et al. |
| 5,931,814 A | 8/1999 | Alex et al. |
| 5,933,136 A | 8/1999 | Brown |
| 5,944,661 A | 8/1999 | Swette et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,976,085 A | 11/1999 | Kimball et al. |
| 5,982,285 A | 11/1999 | Bueche et al. |
| 5,995,860 A | 11/1999 | Sun et al. |
| 6,001,067 A | 12/1999 | Shults et al. |
| 6,016,448 A | 1/2000 | Busacker et al. |
| 6,024,699 A | 2/2000 | Surwit et al. |
| 6,027,445 A | 2/2000 | Von Bahr |
| 6,036,924 A | 3/2000 | Simons et al. |
| 6,049,727 A | 4/2000 | Crothall |
| 6,059,946 A | 5/2000 | Yukawa et al. |
| 6,081,735 A | 6/2000 | Diab et al. |
| 6,081,736 A | 6/2000 | Colvin et al. |
| 6,083,523 A | 7/2000 | Dionne et al. |
| 6,088,608 A | 7/2000 | Schulman et al. |
| 6,091,975 A | 7/2000 | Daddona et al. |
| 6,093,172 A | 7/2000 | Funderburk et al. |
| 6,107,083 A | 8/2000 | Collins et al. |
| 6,122,536 A | 9/2000 | Sun et al. |
| 6,123,827 A | 9/2000 | Wong et al. |
| 6,135,978 A | 10/2000 | Houben et al. |
| 6,144,869 A | 11/2000 | Berner et al. |
| 6,162,611 A | 12/2000 | Heller et al. |
| 6,167,362 A | 12/2000 | Brown et al. |
| 6,168,568 B1 | 1/2001 | Gavriely |
| 6,175,752 B1 | 1/2001 | Say et al. |
| 6,180,416 B1 | 1/2001 | Kurnik et al. |
| 6,201,980 B1 | 3/2001 | Darrow et al. |
| 6,201,993 B1 | 3/2001 | Kruse et al. |
| 6,208,894 B1 | 3/2001 | Schulman et al. |
| 6,212,416 B1 | 4/2001 | Ward et al. |
| 6,212,424 B1 | 4/2001 | Robinson |
| 6,223,083 B1 | 4/2001 | Rosar |
| 6,230,059 B1 | 5/2001 | Duffin |
| 6,233,080 B1 | 5/2001 | Brenner et al. |
| 6,233,471 B1 | 5/2001 | Berner et al. |
| 6,248,067 B1 | 6/2001 | Causey, III et al. |
| 6,256,522 B1 | 7/2001 | Schultz |
| 6,259,937 B1 | 7/2001 | Schulman et al. |
| 6,272,364 B1 | 8/2001 | Kurnik |
| 6,272,480 B1 | 8/2001 | Tresp et al. |
| 6,275,717 B1 | 8/2001 | Gross et al. |
| 6,284,478 B1 | 9/2001 | Heller et al. |
| 6,299,578 B1 | 10/2001 | Kurnik et al. |
| 6,302,855 B1 | 10/2001 | Lav et al. |
| 6,309,351 B1 | 10/2001 | Kurnik et al. |
| 6,309,884 B1 | 10/2001 | Cooper et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,366,794 B1 | 4/2002 | Moussy et al. |
| 6,370,941 B2 | 4/2002 | Nakamura et al. |
| 6,379,301 B1 | 4/2002 | Worthington et al. |
| 6,416,651 B1 | 7/2002 | Millar |
| 6,424,847 B1 | 7/2002 | Mastrototaro et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,484,046 B1 | 11/2002 | Say et al. |
| 6,510,329 B2 | 1/2003 | Heckel |
| 6,512,939 B1 | 1/2003 | Colvin et al. |
| 6,526,298 B1 | 2/2003 | Khalil et al. |
| 6,527,729 B1 | 3/2003 | Turcott |
| 6,537,806 B1 | 3/2003 | Osborne et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,579,498 B1 | 6/2003 | Eglise |
| 6,579,690 B1 | 6/2003 | Bonnecaze et al. |
| 6,585,519 B1 | 7/2003 | Jenkins et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,072 B2 | 8/2003 | Struys et al. |
| 6,618,934 B1 | 9/2003 | Feldman et al. |
| 6,633,772 B2 | 10/2003 | Ford et al. |
| 6,641,533 B2 | 11/2003 | Causey, III et al. |
| 6,673,022 B1 | 1/2004 | Bobo et al. |
| 6,673,596 B1 | 1/2004 | Sayler et al. |
| 6,699,188 B2 | 3/2004 | Wessel |
| 6,702,857 B2 | 3/2004 | Brauker et al. |
| 6,702,972 B1 | 3/2004 | Markle |
| 6,741,877 B1 | 5/2004 | Shults et al. |
| 6,869,413 B2 | 3/2005 | Langley et al. |
| 6,895,263 B2 | 5/2005 | Shin et al. |
| 6,925,393 B1 | 8/2005 | Kalatz et al. |
| 6,931,327 B2 | 8/2005 | Goode, Jr. et al. |
| 6,952,604 B2 | 10/2005 | Denuzzio et al. |
| 6,998,247 B2 | 2/2006 | Monfre et al. |
| 7,011,630 B2 | 3/2006 | Desai et al. |
| 7,025,743 B2 | 4/2006 | Mann et al. |
| 7,029,444 B2 | 4/2006 | Shin et al. |
| 7,060,059 B2 | 6/2006 | Keith et al. |
| 7,074,307 B2 | 7/2006 | Simpson et al. |
| 7,098,803 B2 | 8/2006 | Mann et al. |
| 7,134,999 B2 | 11/2006 | Brauker et al. |
| 7,169,289 B2 | 1/2007 | Schulein et al. |
| 7,229,288 B2 | 6/2007 | Stuart et al. |
| 7,261,671 B2 | 8/2007 | Ortmann et al. |
| 7,261,690 B2 | 8/2007 | Teller et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,354,420 B2 | 4/2008 | Steil et al. |
| 7,359,723 B2 | 4/2008 | Jones |
| 7,402,153 B2 | 7/2008 | Steil et al. |
| 7,417,164 B2 | 8/2008 | Suri |

(56) References Cited

U.S. PATENT DOCUMENTS

| | | | |
|---|---|---|---|
| 7,426,408 B2 | 9/2008 | Denuzzio et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,618,368 B2 | 11/2009 | Brown |
| 7,624,028 B1 | 11/2009 | Brown |
| 7,640,032 B2 | 12/2009 | Jones |
| 7,640,048 B2 | 12/2009 | Dobbles et al. |
| 7,905,833 B2 | 3/2011 | Brister et al. |
| 7,963,917 B2 | 6/2011 | Kellogg et al. |
| 8,533,007 B2 | 9/2013 | Egami et al. |
| 8,585,593 B2 | 11/2013 | Kovatchev et al. |
| 8,892,999 B2 | 11/2014 | Nims et al. |
| 8,974,439 B2 | 3/2015 | Estes |
| 9,446,194 B2 | 9/2016 | Kamath et al. |
| 10,537,678 B2 | 1/2020 | Kamath et al. |
| 10,610,642 B2 | 4/2020 | Kamath et al. |
| 10,675,405 B2 | 6/2020 | Kamath et al. |
| 2001/0016682 A1 | 8/2001 | Berner et al. |
| 2001/0029319 A1* | 10/2001 | Kazlausky ............ A61B 5/486 |
| | | 600/300 |
| 2001/0041830 A1 | 11/2001 | Varalli et al. |
| 2001/0051768 A1 | 12/2001 | Schulman et al. |
| 2002/0019022 A1 | 2/2002 | Dunn et al. |
| 2002/0026111 A1 | 2/2002 | Ackerman |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0055859 A1* | 5/2002 | Goodman .......... G06Q 30/0226 |
| | | 705/3 |
| 2002/0065453 A1 | 5/2002 | Lesho et al. |
| 2002/0068860 A1 | 6/2002 | Clark, Jr. |
| 2002/0099282 A1 | 7/2002 | Knobbe et al. |
| 2002/0111547 A1 | 8/2002 | Knobbe et al. |
| 2002/0119711 A1 | 8/2002 | Vanantwerp et al. |
| 2002/0155615 A1 | 10/2002 | Novikov et al. |
| 2002/0161288 A1 | 10/2002 | Shin et al. |
| 2002/0198513 A1 | 12/2002 | Lebel et al. |
| 2003/0006669 A1 | 1/2003 | Pei et al. |
| 2003/0023171 A1 | 1/2003 | Sato et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0050537 A1* | 3/2003 | Wessel ................ A61B 5/6887 |
| | | 600/300 |
| 2003/0050546 A1 | 3/2003 | Desai et al. |
| 2003/0070548 A1 | 4/2003 | Clausen |
| 2003/0076082 A1 | 4/2003 | Morgan et al. |
| 2003/0078481 A1 | 4/2003 | Mcivor et al. |
| 2003/0078560 A1 | 4/2003 | Miller et al. |
| 2003/0097082 A1 | 5/2003 | Purdy et al. |
| 2003/0100821 A1 | 5/2003 | Heller et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0187338 A1 | 10/2003 | Say et al. |
| 2003/0188427 A1 | 10/2003 | Say et al. |
| 2003/0211625 A1 | 11/2003 | Cohan et al. |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0235817 A1 | 12/2003 | Bartkowiak et al. |
| 2004/0011671 A1 | 1/2004 | Shults et al. |
| 2004/0015063 A1 | 1/2004 | Denuzzio et al. |
| 2004/0024327 A1 | 2/2004 | Brodnick |
| 2004/0039297 A1 | 2/2004 | Abreu |
| 2004/0039298 A1 | 2/2004 | Abreu |
| 2004/0045879 A1 | 3/2004 | Shults et al. |
| 2004/0054263 A1* | 3/2004 | Moerman ............ A61B 5/0002 |
| | | 600/300 |
| 2004/0078219 A1 | 4/2004 | Kaylor et al. |
| 2004/0106857 A1 | 6/2004 | Gough |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0167801 A1 | 8/2004 | Say et al. |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2005/0010265 A1 | 1/2005 | Baru Fassio et al. |
| 2005/0010442 A1 | 1/2005 | Kragh |
| 2005/0021372 A1* | 1/2005 | Mikkelsen ........... A61B 5/4833 |
| | | 600/300 |
| 2005/0027180 A1 | 2/2005 | Goode, Jr. et al. |
| 2005/0027181 A1 | 2/2005 | Goode, Jr. et al. |
| 2005/0027182 A1 | 2/2005 | Siddiqui et al. |
| 2005/0027463 A1 | 2/2005 | Goode, Jr. et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 | 5/2005 | Denuzzio et al. |
| 2005/0101847 A1 | 5/2005 | Routt et al. |
| 2005/0102159 A1 | 5/2005 | Mondshine |
| 2005/0113653 A1 | 5/2005 | Fox et al. |
| 2005/0115832 A1 | 6/2005 | Simpson et al. |
| 2005/0121322 A1 | 6/2005 | Say et al. |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0187720 A1 | 8/2005 | Goode, Jr. et al. |
| 2005/0187749 A1 | 8/2005 | Singley |
| 2005/0192557 A1 | 9/2005 | Brauker et al. |
| 2005/0203360 A1 | 9/2005 | Brauker et al. |
| 2005/0211571 A1 | 9/2005 | Schulein et al. |
| 2005/0215872 A1 | 9/2005 | Berner et al. |
| 2005/0239154 A1 | 10/2005 | Feldman et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0289092 A1 | 12/2005 | Sumner, II et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0047192 A1 | 3/2006 | Hellwig et al. |
| 2006/0089542 A1 | 4/2006 | Sands |
| 2006/0100588 A1 | 5/2006 | Brunnberg et al. |
| 2006/0149156 A1 | 7/2006 | Cochran et al. |
| 2006/0183984 A1 | 8/2006 | Dobbles et al. |
| 2006/0183985 A1 | 8/2006 | Brister et al. |
| 2006/0217329 A1* | 9/2006 | Feinstein ................ A61P 9/00 |
| | | 514/44 A |
| 2006/0222566 A1 | 10/2006 | Brauker et al. |
| 2006/0239934 A1 | 10/2006 | Cheatham et al. |
| 2006/0258929 A1 | 11/2006 | Goode, Jr. et al. |
| 2006/0272652 A1 | 12/2006 | Stocker et al. |
| 2007/0010950 A1 | 1/2007 | Abensour et al. |
| 2007/0012324 A1 | 1/2007 | Nirkondar et al. |
| 2007/0016381 A1 | 1/2007 | Kamath et al. |
| 2007/0032706 A1 | 2/2007 | Kamath et al. |

(56)                References Cited

U.S. PATENT DOCUMENTS

| | | | |
|---|---|---|---|
| 2007/0049873 A1 | 3/2007 | Hansen et al. | |
| 2007/0066873 A1 | 3/2007 | Kamath et al. | |
| 2007/0129621 A1 | 6/2007 | Kellogg et al. | |
| 2007/0179356 A1* | 8/2007 | Wessel | G16H 40/63 |
| | | | 128/920 |
| 2007/0203410 A1 | 8/2007 | Say et al. | |
| 2007/0203966 A1 | 8/2007 | Brauker et al. | |
| 2007/0208244 A1 | 9/2007 | Brauker et al. | |
| 2007/0208245 A1 | 9/2007 | Brauker et al. | |
| 2007/0208246 A1 | 9/2007 | Brauker et al. | |
| 2007/0213610 A1 | 9/2007 | Say et al. | |
| 2007/0288266 A1 | 12/2007 | Sysko et al. | |
| 2008/0015422 A1 | 1/2008 | Wessel | |
| 2008/0021666 A1 | 1/2008 | Goode, Jr. et al. | |
| 2008/0033254 A1 | 2/2008 | Kamath et al. | |
| 2008/0086533 A1 | 4/2008 | Neuhauser et al. | |
| 2008/0125636 A1* | 5/2008 | Ward | A61B 5/14532 |
| | | | 600/365 |
| 2008/0171967 A1 | 7/2008 | Blomquist et al. | |
| 2008/0183061 A1 | 7/2008 | Goode et al. | |
| 2008/0183399 A1 | 7/2008 | Goode et al. | |
| 2008/0187655 A1 | 8/2008 | Markle et al. | |
| 2008/0188722 A1 | 8/2008 | Markle et al. | |
| 2008/0188725 A1 | 8/2008 | Markle et al. | |
| 2008/0189051 A1 | 8/2008 | Goode et al. | |
| 2008/0193936 A1 | 8/2008 | Squirrell | |
| 2008/0194936 A1 | 8/2008 | Goode et al. | |
| 2008/0194937 A1 | 8/2008 | Goode et al. | |
| 2008/0195967 A1 | 8/2008 | Goode et al. | |
| 2008/0215003 A1 | 9/2008 | Kornerup et al. | |
| 2008/0228055 A1* | 9/2008 | Sher | A61B 5/14532 |
| | | | 600/365 |
| 2008/0249384 A1 | 10/2008 | Skyggebjerg et al. | |
| 2008/0262469 A1* | 10/2008 | Brister | A61M 5/1723 |
| | | | 604/246 |
| 2008/0287764 A1 | 11/2008 | Rasdal et al. | |
| 2008/0287765 A1 | 11/2008 | Rasdal et al. | |
| 2008/0287766 A1 | 11/2008 | Rasdal et al. | |
| 2008/0305009 A1 | 12/2008 | Gamsey et al. | |
| 2008/0305506 A1 | 12/2008 | Suri | |
| 2008/0306368 A1 | 12/2008 | Goode, Jr. et al. | |
| 2008/0306433 A1 | 12/2008 | Cesaroni | |
| 2008/0306434 A1 | 12/2008 | Dobbles et al. | |
| 2008/0306435 A1 | 12/2008 | Kamath et al. | |
| 2008/0306444 A1 | 12/2008 | Brister et al. | |
| 2008/0311968 A1 | 12/2008 | Hunter | |
| 2009/0012379 A1 | 1/2009 | Goode, Jr. et al. | |
| 2009/0018418 A1 | 1/2009 | Markle et al. | |
| 2009/0018426 A1 | 1/2009 | Markle et al. | |
| 2009/0036758 A1 | 2/2009 | Brauker et al. | |
| 2009/0043181 A1 | 2/2009 | Brauker et al. | |
| 2009/0043182 A1 | 2/2009 | Brauker et al. | |
| 2009/0043525 A1 | 2/2009 | Brauker et al. | |
| 2009/0043541 A1 | 2/2009 | Brauker et al. | |
| 2009/0043542 A1 | 2/2009 | Brauker et al. | |
| 2009/0058635 A1 | 3/2009 | Lalonde et al. | |
| 2009/0061528 A1 | 3/2009 | Suri | |
| 2009/0062635 A1 | 3/2009 | Brauker et al. | |
| 2009/0062645 A1 | 3/2009 | Fehre et al. | |
| 2009/0076361 A1 | 3/2009 | Kamath et al. | |
| 2009/0081803 A1 | 3/2009 | Gamsey et al. | |
| 2009/0093687 A1 | 4/2009 | Telfort et al. | |
| 2009/0124877 A1 | 5/2009 | Goode, Jr. et al. | |
| 2009/0124878 A1 | 5/2009 | Goode, Jr. et al. | |
| 2009/0143661 A1* | 6/2009 | Taub | A61B 5/14532 |
| | | | 600/365 |
| 2009/0144639 A1 | 6/2009 | Nims et al. | |
| 2009/0156924 A1 | 6/2009 | Shariati et al. | |
| 2009/0177143 A1 | 7/2009 | Markle et al. | |
| 2009/0177147 A1* | 7/2009 | Blomquist | A61M 5/1723 |
| | | | 702/19 |
| 2009/0182217 A1 | 7/2009 | Li et al. | |
| 2009/0192366 A1 | 7/2009 | Mensinger et al. | |
| 2009/0192380 A1 | 7/2009 | Shariati et al. | |

| | | | |
|---|---|---|---|
| 2009/0192722 A1 | 7/2009 | Shariati et al. | |
| 2009/0192724 A1 | 7/2009 | Brauker et al. | |
| 2009/0192745 A1 | 7/2009 | Kamath et al. | |
| 2009/0192751 A1 | 7/2009 | Kamath et al. | |
| 2009/0203981 A1 | 8/2009 | Brauker et al. | |
| 2009/0204341 A1 | 8/2009 | Brauker et al. | |
| 2009/0216103 A1 | 8/2009 | Brister et al. | |
| 2009/0240120 A1 | 9/2009 | Mensinger et al. | |
| 2009/0240128 A1 | 9/2009 | Mensinger et al. | |
| 2009/0240193 A1 | 9/2009 | Mensinger et al. | |
| 2009/0242399 A1 | 10/2009 | Kamath et al. | |
| 2009/0242425 A1 | 10/2009 | Kamath et al. | |
| 2009/0264719 A1 | 10/2009 | Markle et al. | |
| 2009/0287074 A1 | 11/2009 | Shults et al. | |
| 2009/0299151 A1 | 12/2009 | Taub et al. | |
| 2009/0299162 A1 | 12/2009 | Brauker et al. | |
| 2009/0299276 A1 | 12/2009 | Brauker et al. | |
| 2010/0010324 A1 | 1/2010 | Brauker et al. | |
| 2010/0010331 A1 | 1/2010 | Brauker et al. | |
| 2010/0010332 A1 | 1/2010 | Brauker et al. | |
| 2010/0016687 A1 | 1/2010 | Brauker et al. | |
| 2010/0022855 A1 | 1/2010 | Brauker et al. | |
| 2010/0030053 A1 | 2/2010 | Goode, Jr. et al. | |
| 2010/0030484 A1 | 2/2010 | Brauker et al. | |
| 2010/0036215 A1 | 2/2010 | Goode, Jr. et al. | |
| 2010/0036216 A1 | 2/2010 | Goode, Jr. et al. | |
| 2010/0036222 A1 | 2/2010 | Goode, Jr. et al. | |
| 2010/0036223 A1 | 2/2010 | Goode, Jr. et al. | |
| 2010/0036224 A1 | 2/2010 | Goode, Jr. et al. | |
| 2010/0036225 A1 | 2/2010 | Goode, Jr. et al. | |
| 2010/0045465 A1 | 2/2010 | Brauker et al. | |
| 2010/0052899 A1 | 3/2010 | Bruce | |
| 2010/0057043 A1 | 3/2010 | Kovatchev et al. | |
| 2010/0081908 A1 | 4/2010 | Dobbles et al. | |
| 2010/0106000 A1* | 4/2010 | Thomas | A61B 5/14532 |
| | | | 604/890.1 |
| 2010/0161269 A1 | 6/2010 | Kamath et al. | |
| 2010/0174266 A1 | 7/2010 | Estes | |
| 2010/0191075 A1* | 7/2010 | Angelides | G16H 20/10 |
| | | | 709/219 |
| 2010/0240978 A1* | 9/2010 | LaBastide | G16H 20/60 |
| | | | 600/365 |
| 2010/0261987 A1 | 10/2010 | Kamath et al. | |
| 2010/0274218 A1 | 10/2010 | Yodfat et al. | |
| 2010/0280499 A1* | 11/2010 | Yodfat | G16H 20/17 |
| | | | 604/890.1 |
| 2010/0312483 A1 | 12/2010 | Peyser et al. | |
| 2011/0160544 A1* | 6/2011 | Hayter | G16H 50/20 |
| | | | 600/300 |
| 2012/0035448 A1 | 2/2012 | Taub et al. | |
| 2012/0051983 A1* | 3/2012 | Hoenes | A61B 5/1411 |
| | | | 422/430 |
| 2013/0324823 A1* | 12/2013 | Koski | A61B 5/0004 |
| | | | 600/365 |
| 2014/0012511 A1* | 1/2014 | Mensinger | A61B 5/4839 |
| | | | 702/19 |
| 2014/0114161 A1 | 4/2014 | Kamath et al. | |
| 2016/0081632 A1 | 3/2016 | Kamath et al. | |
| 2016/0101232 A1 | 4/2016 | Kamath et al. | |
| 2019/0142345 A1 | 5/2019 | Dehennis et al. | |

FOREIGN PATENT DOCUMENTS

| | | | |
|---|---|---|---|
| EP | 0320109 A1 | 6/1989 | |
| EP | 0353328 A1 | 2/1990 | |
| EP | 0390390 A1 | 10/1990 | |
| EP | 0563795 A1 | 10/1993 | |
| EP | 0817809 A1 | 1/1998 | |
| EP | 0838230 A2 | 4/1998 | |
| EP | 0880936 A2 | 12/1998 | |
| EP | 0885932 A2 | 12/1998 | |
| EP | 1077634 A1 | 2/2001 | |
| EP | 1078258 A1 | 2/2001 | |
| FR | 2656423 A1 | 6/1991 | |
| FR | 2760962 A1 | 9/1998 | |
| GB | 1442303 A | 7/1976 | |
| GB | 2149918 A | 6/1985 | |
| WO | WO-8902720 A1 | 4/1989 | |

(56) References Cited

FOREIGN PATENT DOCUMENTS

| | | |
|---|---|---|
| WO | WO-9000738 A1 | 1/1990 |
| WO | WO-9010861 A1 | 9/1990 |
| WO | WO-9213271 A1 | 8/1992 |
| WO | WO-9314693 A1 | 8/1993 |
| WO | WO-9422367 A1 | 10/1994 |
| WO | WO-9614026 A1 | 5/1996 |
| WO | WO-9625089 A1 | 8/1996 |
| WO | WO-9630431 A1 | 10/1996 |
| WO | WO-9701986 A1 | 1/1997 |
| WO | WO-9728737 A1 | 8/1997 |
| WO | WO-9824358 A2 | 6/1998 |
| WO | WO-9948419 A1 | 9/1999 |
| WO | WO-9956613 A1 | 11/1999 |
| WO | WO-9958051 A1 | 11/1999 |
| WO | WO-9958973 A1 | 11/1999 |
| WO | WO-0012720 A2 | 3/2000 |
| WO | WO-0019887 A1 | 4/2000 |
| WO | WO-0032098 A1 | 6/2000 |
| WO | WO-0033065 A1 | 6/2000 |
| WO | WO-0059373 A1 | 10/2000 |
| WO | WO-0074753 A1 | 12/2000 |
| WO | WO-0078210 A1 | 12/2000 |
| WO | WO-0120019 A2 | 3/2001 |
| WO | WO-0120334 A1 | 3/2001 |
| WO | WO-0134243 A1 | 5/2001 |
| WO | WO-0152727 A1 | 7/2001 |
| WO | WO-0158348 A2 | 8/2001 |
| WO | WO-0168901 A2 | 9/2001 |
| WO | WO-0169222 A2 | 9/2001 |
| WO | WO-0188524 A1 | 11/2001 |
| WO | WO-0188534 A2 | 11/2001 |
| WO | WO-0224065 A1 | 3/2002 |
| WO | WO-0078210 A9 | 5/2002 |
| WO | WO-02082989 A1 | 10/2002 |
| WO | WO-02100266 A1 | 12/2002 |
| WO | WO-2005011489 A1 | 2/2005 |
| WO | WO-2005012873 A2 | 2/2005 |
| WO | WO-2005057168 A2 | 6/2005 |
| WO | WO-2005057175 A2 | 6/2005 |
| WO | WO-2005081119 A2 | 9/2005 |
| WO | WO-2005026689 A9 | 10/2005 |
| WO | WO-2006105146 A2 | 10/2006 |
| WO | WO-2008076868 A2 | 6/2008 |

OTHER PUBLICATIONS

Aalders, et al., "Development of a Wearable Glucose Sensor; Studies in Healthy Volunteers and in Diabetic Patients," The International Journal Of Artificial Organs, 1991, vol. 14, No. 2, pp. 102-108.
Abe, et al., "Characterization of Glucose Microsensors for Intracellular Measurements," Analytical Chemistry, 1992, vol. 64, No. 18, pp. 2160-2163.
Abel, et al., "Biosensors For in Vivo Glucose Measurements: Can We Cross the Experimental Stage," Biosensors & Bioelectronics, 2002, vol. 17, pp. 1059-1070.
Abel, et al., "Experience With An Implantable Glucose Sensor as a Prerequisite of an Artificial Beta Cell," Biomed. Biochim. Actan, 1984, vol. 43, No. 5, pp. 577-584.
Adilman, et al., "Videogames: Knowing The Score, Creative Computing," Dec. 1983, Dialog: File 148; IAC Trade & Industry Database, vol. 9, p. 224(5) (9 pages).
Alcock S.J., et al., "Continuous Analyte Monitoring To Aid Clinical Practice," IEEE Engineering in Medicine & Biology, 1994, vol. 13, pp. 319-325.
Amer M.M.B., "An Accurate Amperometric Glucose Sensor Based Glucometer with Eliminated Cross-Sensitivity," Journal of Medical Engineering & Technology, vol. 26 (5), Sep./Oct. 2002, pp. 208-213.
Amin R., et al., "Hypoglycemia Prevalence in Prepubertal Children With Type 1 Diabetes on Standard Insulin Regimen: Use of Continuous Glucose Monitoring System," Diabetes Care, 2003, vol. 26, No. 3, pp. 662-667.

Armour J.C., et al., "Application of Chronic Intravascular Blood Glucose Sensor in Dogs," Diabetes, Dec. 1990, vol. 39, pp. 1519-1526.
Atanasov P., et al., "Biosensor for Continuous Glucose Monitoring," Biotechnology and Bioengineering, John Wiley & sons Inc, 1994, vol. 43, pp. 262-266.
Atanasov P., et al., "Implantation of a Refillable Glucose Monitoring-Telemetry Device," Biosenors and Bioelectronics, vol. 12 (7), 1997, pp. 669-680.
Aussedat B., et al., "A User-Friendly Method For Calibrating a Subcutaneous Glucose Sensor-Based Hypoglycaemic Alarm," Elsevier Science Limited, Biosensors & Bioelectronic, 1997, vol. 12, No. 11, pp. 1061-1071.
Bailey T.S., et al., "Reduction in Hemoglobin A1C with Real-Time Continuous Glucose Monitoring: Results from a 12-Week Observational Study," Diabetes Technology & Therapeutics, vol. 9 (3), 2007, pp. 203-210.
Baker D.A., et al., "Dynamic Concentration Challenges for Biosensor Characterization," Biosensors & Bioelectronics, vol. 8, 1993, pp. 433-441.
Baker D.A., et al., "Dynamic Delay and Maximal Dynamic Error in Continuous Biosensors," Analytical Chemistry, vol. 68 (8), Apr. 15, 1996, pp. 1292-1297.
Bard A.J., et al., "Electrochemical Methods," Fundamentals and Applications, John Wiley & Sons, New York, 1980, pp. 173-175.
Beach R.D., et al., "Subminiature Implantable Potentiostat and Modified Commercial Telemetry Device for Remote Glucose Monitoring," IEEE Transactions on Instrumentation and Measurement, vol. 48 (6), Dec. 1999, pp. 1239-1245.
Bellucci F., et al., "Electrochemical Behaviour of Graphite-Epoxy Composite Materials (GECM) in Aqueous Salt Solutions," Journal of Applied Electrochemistry, vol. 16 (1), Jan. 1986, pp. 15-22.
Bessman S.P., et al., "Progress toward a Glucose Sensor for the Artificial Pancreas," Proceedings of a Workshop on Ion-Selective Microelectrodes, Jun. 4-5, 1973, Boston University, 1973, pp. 189-197.
Biermann E., et al., "How Would Patients Behave if they were Continually Informed of their Blood Glucose Levels? A Simulation Study Using a "Virtual" Patient," Diabetes Technology & Therapeutics, vol. 10 (3), 2008, pp. 178-187.
Bindra D.S., et al., "Design and in Vitro Studies of a Needle-Type Glucose Sensor for Subcutaneous Monitoring," Analytical Chemistry, vol. 63, Sep. 1, 1991, pp. 1692-1696.
Bindra D.S., et al., "Pulsed Amperometric Detection of Glucose in Biological Fluids at a Surface-Modified Gold Electrode," Analytical Chemistry, vol. 61 (22), Nov. 15, 1989, pp. 2566-2570.
Bisenberger M., et al., "A Triple-Step Potential Waveform at Enzyme Multisensors with Thick-Film Gold Electrodes for Detection of Glucose and Sucrose," Sensors and Actuators B, vol. 28, 1995, pp. 181-189.
Bland J.M., et al., "A Note on the Use of the Intraclass Correlation Coefficient in the Evaluation of Agreement between Two Methods of Measurement," Computers in Biology and Medicine, vol. 20 (5), 1990, pp. 337-340.
Bland J.M., et al., "Statistical Methods for Assessing Agreement Between Two Methods of Clinical Measurement," The Lancet, Feb. 8, 1986, pp. 307-310.
Bobbioni-Harsch E., et al., "Lifespan of Subcutaneous Glucose Sensors and their Performances during Dynamic Glycaemia Changes in Rats," J. Biomed. Eng., vol. 15, 1993, pp. 457-463.
Bode B.W., "Clinical Utility of the Continuous Glucose Monitoring System," Diabetes Technology & Therapeutics, vol. 2, Supplement 1, 2000, pp. S35-S41.
Bode B.W., et al., "Continuous Glucose Monitoring Used to Adjust Diabetes Therapy Improves Glycosylated Hemoglobin: A Pilot Study," Diabetes Research and Clinical Practice, vol. 46, 1999, pp. 183-190.
Bode B.W., et al., "Using the Continuous Glucose Monitoring System to Improve the Management of Type 1 Diabetes," Diabetes Technology & Therapeutics, vol. 2, Supplement 1, 2000, pp. S43-S48.

(56)　　　　　References Cited

OTHER PUBLICATIONS

Boedeker Plastics Inc, "Polyethylene Specifications," Polyethylene Data Sheet, Retrieved from http://www.boedeker.com/polye.sub.--p.htm on Aug. 19, 2009, 4 pages.

Boland E., et al., "Limitations of Conventional Methods of Self-Monitoring of Blood Glucose," Diabetes Care, vol. 24 (11), Nov. 2001, pp. 1858-1862.

Bolinder J., et al., "Self-Monitoring of Blood Glucose in Type I Diabetic Patients: Comparison with Continuous Microdialysis Measurements of Glucose in Subcutaneous Adipose Tissue during Ordinary Life Conditions," Diabetes Care, vol. 20 (1), Jan. 1997, pp. 64-70.

Bolinder J., et al., "Microdialysis Measurement of the Absolute Glucose Concentration in Subcutaneous Adipose Tissue Allowing Glucose Monitoring in Diabetic Patients," Rapid Communication, Diabetologia, vol. 35, 1992, pp. 1177-1180.

Bott A.W., "A Comparison of Cyclic Voltammetry and Cyclic Staircase Voltammetry," Current Separations, vol. 16 (1), 1997, pp. 23-26.

Bott A.W., "Electrochemical Methods for the Determination of Glucose," Current Separations, vol. 17 (1), 1998, pp. 25-31.

Bowman L., et al., "The Packaging of Implantable Integrated Sensors," IEEE Transactions in Biomedical Engineering, vol. BME-33 (2), Feb. 1986, pp. 248-255.

Brauker J., et al., "Local Inflammatory Response Around Diffusion Chambers Containing Xenografts," Transplantation, vol. 61 (12), Jun. 27, 1996, pp. 1671-1677.

Braunwald E., "Biomarkers in Heart Failure," Medical Progress, The New England Journal of Medicine, vol. 358, May 15, 2008, pp. 2148-2159.

Bremer T., et al., "Is Blood Glucose Predictable from Previous Values? A Solicitation for Data," Perspectives in Diabetes, vol. 48, Mar. 1999, pp. 445-451.

Bremer T.M., et al., "Benchmark Data from the Literature for Evaluation of New Glucose Sensing Technologies," Diabetes Technology & Therapeutics, vol. 3 (3), 2001, pp. 409-418.

Brooks S.L., et al., "Development of an On-line Glucose Sensor for Fermentation Monitoring," Biosensors, vol. 3, 1987/1988, pp. 45-56.

Bruckel J., et al., "In Vivo Measurement of Subcutaneous Glucose Concentrations with an Enzymatic Glucose Sensor and a Wick Method," Klin Wochenschr, vol. 67, 1989, pp. 491-495.

Brunstein E., et al., "Preparation and Validation of Implantable Electrodes for the Measurement of Oxygen and Glucose," Biomed Biochim. Acta, vol. 48 (11/12), 1989, pp. 911-917.

Cai Q., et al., "A Wireless, Remote Query Glucose Biosensor Based on a pH-Sensitive Polymer," Analytical Chemistry, vol. 76 (14), Jul. 15, 2004, pp. 4038-4043.

Cameron T., et al., "Micromodular Implants to Provide Electrical Stimulation of Paralyzed Muscles and Limbs," IEEE Transactions on Biomedical Engineering, vol. 44 (9), Sep. 1997, pp. 781-790.

Campanella L., et al., "Biosensor for Direct Determination of Glucose and Lactate in Undiluted Biological Fluids," Biosensors & Bioelectronics, vol. 8, 1993, pp. 307-314.

Candas B., et al., "An Adaptive Plasma Glucose Controller Based on a Nonlinear Insulin/Glucose Model," IEEE Transactions on Biomedical Engineering, vol. 41 (2), Feb. 1994, pp. 116-124.

Cass A.E.G., et al., "Ferrocene-Mediated Enzyme Electrodes for Amperometric Determination of Glucose," Analytical Chemistry, vol. 56 (4), Apr. 1984, pp. 667-671.

Cassidy J.F., et al., "Novel Electrochemical Device for the Detection of Cholesterol or Glucose," Analyst, vol. 118, Apr. 1993, pp. 415-418.

Chase H.P., et al., "Continuous Subcutaneous Glucose Monitoring in Children with Type 1 Diabetes," Pediatrics, vol. 107 (2), Feb. 2001, pp. 222-226.

Chen T., et al., "Defining the Period of Recovery of the Glucose Concentration after its Local Perturbation by the Implantation of a Miniature Sensor," Clinical Chemistry and Laboratory Medicine, vol. 40 (8), 2002, pp. 786-789.

Chia C.W., et al., "Glucose Sensors: Toward Closed Loop Insulin Delivery," Endocrinology and Metabolism Clinics of North America, vol. 33, 2004, pp. 175-195.

Choleau C., et al., "Calibration of a Subcutaneous Amperometric Glucose Sensor Implanted for 7 Days in Diabetic Patients Part 2. Superiority of the One-point Calibration Method," Biosensors and Bioelectronics, vol. 17 (8), 2002, pp. 647-654.

Choleau C., et al., "Calibration of a Subcutaneous Amperometric Glucose Sensor Part 1. Effect of Measurement Uncertainties on the Determination of Sensor Sensitivity and Background Current," Biosensors and Bioelectronics, vol. 17, 2002, pp. 641-646.

Ciba Specialty Chemicals, "Ciba® IRGACURE® 2959," Coating Effects Segment, Photoinitiator Product Description, Basel Switzerland, Apr. 2, 1998, 3 pages.

Claremont D.J., et al., "Potentially-Implantable, Ferrocene-Mediated Glucose Sensor," Journal of Biomedical Engineering, vol. 8, Jul. 1986, pp. 272-274.

Claremont D.J., et al., "Subcutaneous Implantation of a Ferrocene-Mediated Glucose Sensor in Pigs," Diabetologia, vol. 29, 1986, pp. 817-821.

Clark L.C., et al., "Configurational Cyclic Voltammetry: Increasing the Specificity and Reliability of Implanted Electrodes," IEEE/Ninth Annual Conference of the Engineering in Medicine and Biology Society, 1987, pp. 0782-0783.

Clark L.C., et al., "Long-Term Stability of Electroenzymatic Glucose Sensors Implanted in Mice," vol. XXXIV, Transactions—American Society for Artificial Internal Organs, 1988, vol. 34, pp. 259-265.

Clark L.C., et al., "One-Minute Electrochemical Enzymic Assay for Cholesterol in Biological Materials," Clinical Chemistry, vol. 27 (12), 1981, pp. 1978-1982.

Clarke W.L., et al., "Evaluating Clinical Accuracy of Systems for Self Monitoring of Blood Glucose," Technical Articles, Diabetes Care, vol. 10 (5), Sep.-Oct. 1987, pp. 622-628.

Colangelo V.J., et al., "Corrosion Rate Measurements in Vivo," Journal of Biomedical Materials Research, vol. 1, 1967, pp. 405-414.

Colowick S.P., et al., "Methods in Enzymology," vol. XLIV, Immobilized Enzymes, Edited by Mosbach K, New York Academic Press, 1976, 11 pages.

Cox D.J., et al., "Accuracy of Perceiving Blood Glucose in IDDM," Diabetes Care, vol. 8 (6), Nov.-Dec. 1985, pp. 529-536.

Csoregi E., et al., "Amperometric Microbiosensors for Detection of Hydrogen Peroxide and Glucose Based on Peroxidase-Modified Carbon Fibers," Electroanalysis, vol. 6, 1994, pp. 925-933.

Csoregi E., et al., "Design, Characterization and One-Point in Vivo Calibration of a Subcutaneously Implanted Glucose Electrode," American Chemical Society, Analytical Chemistry, vol. 66 (19), Oct. 1, 1994, pp. 3131-3138.

Currie J.F., et al., "Novel Non-Intrusive Trans-Dermal Remote Wireless Micro-Fluidic Monitoring System Applied to Continuous Glucose and Lactate Assays for Casualty Care and Combat Readiness Assessment," RTO HFM Symposium, RTO-MP-HFM-109, Aug. 16-18, 2004, pp. 24-1-24-18.

Danielsson B., et al., "Enzyme Thermistors," Methods in Enzymology, vol. 137, 1988, pp. 181-197.

Dassau E., et al., "In Silico Evaluation Platform for Artificial Pancreatic β-Cell Development—A Dynamic Simulator for Closed-Loop Control with Hardware-in-the-loop," Diabetes Technology & Therapeutics, vol. 11 (3), 2009, pp. 1-8.

Davies M.L., et al., "Polymer Membranes in Clinical Sensor Applications," An overview of membrane function, Biomaterials, vol. 13 (14), 1992, pp. 971-978.

Davis G., et al., "Bioelectrochemical Fuel Cell and Sensor Based on a Quinoprotein, Alcohol Dehydrogenase," Enzyme and Microbial Technology, vol. 5 (5), Sep. 1983, pp. 383-388.

Deutsch T., et al., "Time Series Analysis and Control of Blood Glucose Levels in Diabetic Patients," Computer Methods and Programs in Biomedicine, Elsevier Scientific Publishers, vol. 41, 1994, pp. 167-182.

(56)               References Cited

OTHER PUBLICATIONS

Dixon B.M., et al., "Characterization in Vitro and in Vivo of the Oxygen Dependence of an Enzyme/Polymer Biosensor for Monitoring Brain Glucose," Journal of Neuroscience Methods, vol. 119, 2002, pp. 135-142.

DuPont, "Dimension® AR Clinical Chemistry System," The Chemistry Analyzer that Makes the most of your Time, Money and Effort, Dade International, Chemistry Systems, Newark, 1998, 18 pages.

Durliat H., et al., "Spectrophotometric and Electrochemical Determinations of L( +)-Lactate in Blood by Use of Lactate Dehydrogenase from Yeast," Clinical Chemistry, vol. 22 (11), 1976, pp. 1802-1805.

Edwards Lifesciences, "Accuracy for You and Your Patients," Marketing materials, 2002, 4 pages.

El Degheidy M.M., et al., "Optimization of an Implantable Coated Wire Glucose Sensor," Journal of Biomedical Engineering, vol. 8, Apr. 1986, pp. 121-129.

ELCO Diagnostics Company, "Direct 30/30® Blood Glucose Sensor," Markwell Medical Catalog, 1990, 1 page.

El-Khatib F.H., et al., "Adaptive Closed-Loop Control Provides Blood-Glucose Regulation Using Dual Subcutaneous Insulin and Glucagon Infusion in Diabetic Swine," Journal of Diabetes Science and Technology, Diabetes Technology Society, vol. 1 (2), 2007, pp. 181-192.

El-Sa'ad L., et al., "Moisture Absorption by Epoxy Resins: The Reverse Thermal Effect," Journal of Materials Science, vol. 25, 1990, pp. 3577-3582.

Ernst H., et al., "Reliable Glucose Monitoring Through the Use of Microsystem Technology," Analytical Bioanalytical Chemistry, vol. 373, 2002, pp. 758-761.

Extended European Search Report for Application No. 06748336.2 mailed Jun. 16, 2010, 9 pages.

Extended European Search Report for Application No. 10756957.6 mailed Sep. 11, 2014, 10 pages.

Fabietti P.G., et al., "Clinical Validation of a New Control-Oriented Model of Insulin and Glucose Dynamics in Subjects with Type 1 Diabetes," Diabetes Technology & Therapeutics, vol. 9 (4), 2007, pp. 327-338.

Fahy B.G., et al., "An Analysis: Hyperglycemic Intensive Care Patients Need Continuous Glucose Monitoring-Easier Said Than Done," Journal of Diabetes Science and Technology, Diabetes Technology Society, vol. 2 (2), Mar. 2008, pp. 201-204.

Fare T.L., et al., "Functional Characterization of a Conducting Polymer-Based Immunoassay System," Biosonsors & Bioelectronics, vol. 13 (3-4), 1998, pp. 459-470.

Feldman B., et al., "A Continuous Glucose Sensor Based on Wired EnzymeTM Technology—Results from a 3-Day Trial in Patients with Type 1 Diabetes," Diabetes Technology & Therapeutics, vol. 5 (5), 2003, pp. 769-779.

File History of U.S. Appl. No. 11/157,365, filed Jun. 21, 2005, 977 pages.

Fischer U., et al., "Assessment of Subcutaneous Glucose Concentration: Validation of the Wick Technique as a Reference for Implanted Electrochemical Sensors in Normal and Diabetic Dogs," Diabetologia, vol. 30, 1987, pp. 940-945.

Fischer U., et al., "Hypoglycaemia-Warning by Means of Subcutaneous Electrochemical Glucose Sensors: An Animal Study," Horm. Metab. Res, vol. 27, 1995, p. 53. (Abstract Only).

Fischer U., et al., "Oxygen Tension at the Subcutaneous Implantation Site of Glucose Sensors," Biomed. Biochim. Acta, vol. 48 (11/12), 1989, pp. 965-971.

Freedman D., et al., "Statistics," Second Edition, W.W. Norton & Company, New York & London, 1991, p. 74 (3 pages).

Freiberger P., "Video Game Takes on Diabetes Superhero 'Captain Novolin' Offers Treatment Tips," Fourth Edition, Jun. 26, 1992, Business Section, 2 pages.

Frohnauer M.K., et al., "Graphical Human Insulin Time-Activity Profiles Using Standardized Definitions," Diabetes Technology & Therapeutics, vol. 3 (3), 2001, pp. 419-429.

Frost M.C., et al., "Implantable Chemical Sensors for Real-Time Clinical Monitoring: Progress and Challenges," Current Opinion in Chemical Biology, Analytical Techniques, vol. 6, 2002, pp. 633-641.

Gabby R.A., et al., "Optical Coherence Tomography-Based Continuous Noninvasive Glucose Monitoring in Patients with Diabetes," Diabetes Technology & Therapeutics, vol. 10, Nov. 3, 2008, pp. 188-193.

Ganesan N., et al., "Gold Layer-Based Dual Crosslinking Procedure of Glucose Oxidase with Ferrocene Monocarboxylic Acid Provides a Stable Biosensor," Analytical Biochemistry, Notes & Tips, vol. 343, 2005, pp. 188-191.

Ganesh A., et al., "Evaluation of the VIA® Blood Chemistry Monitor for Glucose in Healthy and Diabetic Volunteers," Journal of Diabetes Science and Technology, vol. 2 (2), Mar. 2008, pp. 182-193.

Garg S.K., et al., "Correlation of Fingerstick Blood Glucose Measurements With GlucoWatch Biographer Glucose Results in Young Subjects With Type 1 Diabetes," Emerging Treatments and Technologies, Diabetes Care, vol. 22 (10), Oct. 1999, pp. 1708-1714.

Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.

Gerritsen M., et al., "Performance of Subcutaneously Implanted Glucose Sensors for Continuous Monitoring," The Netherlands Journal of Medicine, vol. 54, 1999, pp. 167-179.

Gerritsen M., et al., "Problems Associated with Subcutaneously Implanted Glucose Sensors," Diabetes Care, vol. 23 (2), Feb. 2000, pp. 143-145.

Gilligan B.J., et al., "Evaluation of a Subcutaneous Glucose Sensor Out to 3 Months in a Dog Model" Diabetes Care, vol. 17 (8), Aug. 1994, pp. 882-887.

Gilligan B.J., et al., "Feasibility of Continuous Long-Term Glucose Monitoring from a Subcutaneous Glucose Sensor in Humans," Diabetes Technology & Therapeutics, vol. 6 (3), 2004, pp. 378-386.

Godsland I.F., et al., "Maximizing the Success Rate of Minimal Model Insulin Sensivity Measurement in Humans: The Importance of Basal Glucose Levels," The Biochemical Society and the Medical Research Society, Clinical Science, vol. 101, 2001, pp. 1-9.

Gouda M.D., et al., "Thermal Inactivation of Glucose Oxidase," The Journal of Biological Chemistry, vol. 278 (27), Issue of Jul. 4, 2003, pp. 24324-24333.

Gough D.A., et al., "Frequency Characterization of Blood Glucose Dynamics," Annals of Biomedical Engineering, vol. 31, 2003, pp. 91-97.

Gough D.A., et al., "Immobilized Glucose Oxidase in Implantable Glucose Sensor Technology," Diabetes Technology & Therapeutics, vol. 2 (3), 2000, pp. 377-380.

Gross, et al., "Diabetes Technology & Therapeutics," Letters to the Editor, Diabetes Technology & Therapeutics, vol. 3 (1), 2001, pp. 129-131.

Gross T.M., et al., "Efficacy and Reliability of the Continuous Glucose Monitoring System," Diabetes Technology & Therapeutics, vol. 2, Supplement 1, 2000, pp. S19-S26.

Gross T.M., et al., "Performance Evaluation Of The Minimed® Continuous Glucose Monitoring System During Patient Home Use," Diabetes Technology & Therapeutics, vol. 2(1), 2000, pp. 49-56.

Guerci B., et al., "Clinical Performance of CGMS in Type 1 Diabetic Patients Treated by Continuous Subcutaneous Insulin Infusion Using Insulin Analogs," Diabetes Care, vol. 26, 2003, pp. 582-589.

Hall S.B., et al., "Electrochemical Oxidation of Hydrogen Peroxide at Platinum Electrodes. Part 1. An Adsorption-controlled Mechanism," Electrochimica Acta, vol. 43, Nos. 5/6, 1998, pp. 579-588.

Hall S.B., et al., "Electrochemical Oxidation of Hydrogen Peroxide at Platinum Electrodes. Part II: Effect of potential," Electrochimica Acta, vol. 43 (14-15), 1998, pp. 2015-2024.

Hall S.B., et al., "Electrochemical Oxidation of Hydrogen Peroxide at Platinum Electrodes. Part III: Effect of Temperature," Electrochimica Acta, vol. 44, 1999, pp. 2455-2462.

(56) References Cited

OTHER PUBLICATIONS

Hall S.B., et al., "Electrochemical Oxidation of Hydrogen Peroxide at Platinum Electrodes. Part IV: Phosphate Buffer Dependence," Electrochimica Acta, vol. 44, 1999, pp. 4573-4582.

Hall S.B., et al., "Electrochemical Oxidation of Hydrogen Peroxide at Platinum Electrodes. Part V: Inhibition by Chloride," Electrochimica Acta, vol. 45, 2000, pp. 3573-3579.

Hamilton, "Complete Guide to Selecting the Right Hamilton Gastight, Microliter, and Specialty Syringe for your Application," Syringe Selection, www.hamiltoncompany.com, 2006, 20 pages.

Hashiguchi Y., et al., "Development of a Miniaturized Glucose Monitoring System by Combining a Needle-Type Glucose Sensor with Microdialysis Sampling Method: Long-term subcutaneous tissue glucose monitoring in ambulatory diabetic patients," Diabetes Care, vol. 17, No. 5, May 1994, pp. 387-396.

Heise T., et al., "Hypoglycemia warning signal and glucose sensors: Requirements and concepts," Diabetes Technology & Therapeutics, vol. 5, No. 4, 2003, pp. 563-571.

Heller A., "Electrical Connection of Enzyme Redox Centers to Electrodes," J. Phys. Chem., vol. 96, 1992, pp. 3579-3587.

Heller A., "Electrical Wiring of Redox Enzymes," Ace. Chem. Res., vol. 23, 1990, pp. 128-134.

Heller A., "Implanted Electrochemical Glucose Sensors for the Management of Diabetes," Annu. Rev., Biomed Eng., vol. 1, 1999, pp. 153-175.

Heller A., "Plugging Metal Connectors into Enzymes," Nature Biotechnology, vol. 21, No. 6, Jun. 2003, pp. 631-632.

Hicks J.M., "In Situ Monitoring," Clinical Chemistry, vol. 31 (12), 1985, pp. 1931-1935.

Hitchman M.L., "Measurement of Dissolved Oxygen," Edited by Elving P.J et al., Chemical Analysis, New York, John Wiley & Sons, vol. 49, Chapter 3, 1978, pp. 34-49 and 59-123.

Hoel P.G., "Elementary Statistics," Fourth Edition, John Wiley & Sons, Inc., 1976, pp. 113-114.

Houghton Mifflin Company, "American Heritage Dictionary," 4th Edition, 2000, pp. 82.

Houghton Mifflin Company, "Xenogenic, the American Heritage Stedman's Medical Dictionary," 2002, Answers.Com, retrieved from http://www.answers.com/topic/xenogenic, on Nov. 7, 2006, 2 Pages.

Hrapovic S., et al., "Picoamperometric Detection of Glucose at Ultrasmall Platinum-Based Biosensors Preparation and Characterization," Anal. Chem, vol. 75, 2003, pp. 3308-3315.

Hu Y., et al., "A Needle-Type Enzyme-Based Lactate Sensor for In Vivo Monitoring," Analytica Chimica Acta, vol. 281, 1993, pp. 503-511.

Huang C., et al., "Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode," U.S. Department of Commence/NTIS, 1975, 126 pages.

Huang Q., et al., "A 0.5mW Passive Telemetry IC for Biomedical Applications," Proceedings of the 23rd European Solid-State Circuits Conference (ESSCIRC '97), Southampton, UK, Sep. 16-18, 1997, pp. 172-175.

Hunter I., et al., "Minimally Invasive Glucose Sensor and Insulin Delivery System," MIT Home Automation and Healthcare Consortium, Mar. 31, 2000, Progress Report No. 25, 17 pages.

International Preliminary Report on Patentability for Application No. PCT/US2010/028927, mailed Sep. 27, 2011, 6 pages.

International Search Report and Written Opinion for Application No. PCT/US2010/028927, mailed May 26, 2010, 8 pages.

Ishikawa M., et al., "Initial Evaluation of A 290-Mm Diameter Subcutaneous Glucose Sensor: Glucose Monitoring With A Biocompatible, Flexible-Wire, Enzyme-Based Amperometric Microsensor in Diabetic and Nondiabetic Humans," Journal of Diabetes and Its Complications, vol. 12, 1998, pp. 295-301.

Jablecki M., et al., "Simulations of the Frequency Response of Implantable Glucose Sensors," Analytical Chemistry, vol. 72, 2000, 1853-1859.

Jaremko J., et al., "Advances Toward the Implantable Artificial Pancreas for Treatment of Diabetes," Diabetes Care, vol. 21 (3), Mar. 1998, pp. 444-450.

Jensen M.B., et al., "Fast Wave Forms for Pulsed Electrochemical Detection of Glucose by Incorporation of Reductive Desorption of Oxidation Products," Analytical Chemistry, vol. 69 (9), May 1997, pp. 1776-1781.

Jeong R.A., et al., "In Vivo Calibration of the Subcutaneous Amperometric Glucose Sensors Using a Non-Enzyme Electrode," Biosensors and Bioelectronics, Elsevier, vol. 19, 2003, pp. 313-319.

Jeutter D.C., "A Transcutaneous Implanted Battery Recharging and Biotelemeter Power Switching System," IEEE Transactions on Biomedical Engineering, vol. BME-29 (5), May 1982, pp. 314-321.

Jeutter D.C., et al., "Design of a Radio-Linked Implantable Cochlear Prosthesis Using Surface Acoustic Wave Devices," IEEE Transactions on Ultrasonics, Ferroelectrics and Frequency Control, vol. 40 (5), Sep. 1993, pp. 469-477.

Johnson K.W., et al., "In Vivo Evaluation of an Electroenzymatic Glucose Sensor Implanted in Subcutaneous Tissue," Biosensors and Bioelectronics, 1992, vol. 7, pp. 709-714.

Johnson K.W., "Reproducible Electrodeposition of Biomolecules for the Fabrication of Miniature Electroenzymatic Biosensors," Sensors and Actuators B, vol. 5, 1991, pp. 85-89.

Joung G.B., et al., "An Energy Transmission System for an Artificial Heart Using Leakage Inductance Compensation of Transcutaneous Transformer," IEEE Transactions on Power Electronics, vol. 13 (6), Nov. 1998, pp. 1013-1022.

Jovanovic L.M.D., "The Role of Continuous Glucose Monitoring in Gestational Diabetes Mellitus," Diabetes Technology and Therapeutics, vol. 2 (1), 2000, pp. S67-S71.

Kacaniklic V., et al., "Amperometric Biosensors for Detection of L- and D-Amino Acids Based on Coimmoblized Peroxidase and L- and D-Amino Acid Oxidases in Carbon Paste Electrodes," Electroanalysis, vol. 6, May-Jun. 1994, pp. 381-390.

Kamath A., et al., "Calibration of a Continuous Glucose Monitor: Effect of Glucose Rate of Change," Eighth Annual Diabetes Technology Meeting, Nov. 13-15, 2008, pp. A88 (2 pages).

Kang S.K., et al., "In Vitro and Short-Term in Vivo Characteristics of a Kel-F Thin Film Modified Glucose Sensor," Analytical Sciences, vol. 19, Nov. 2003, pp. 1481-1486.

Kaplan S.M., "Wiley Electrical and Electronics Engineering Dictionary," IEEE Press, John Wiley & Sons, Inc., 2004, pp. 141, 142, 548 & 549.

Kaufman F.R., et al., "A Pilot Study of the Continuous Glucose Monitoring System," Diabetes Care, vol. 24 (12), Dec. 2001, pp. 2030-2034.

Kaufman F.R., "Role of the Continuous Glucose Monitoring System in Pediatric Patients," Diabetes Technology and Therapeutics, vol. 2 (1), 2000, S49-S52.

Kawagoe J.L., et al., "Enzyme-Modified Organic Conducting Salt Microelectrode," Analytical Chemistry, vol. 63, 1991, pp. 2961-2965.

Keedy F.H., et al., "Determination of Urate in Undiluted Whole Blood by Enzyme Electrode," Biosensors and Bioelectronics, vol. 6, 1991, pp. 491-499.

Kerner, et al., "A Potentially Implantable Enzyme Electrode for Amperometric Measurement of Glucose," Hormone and Metabolic Research Supplement, vol. 20, 1988, pp. 8-13.

Kerner W., et al., "The Function of a Hydrogen Peroxide-Detecting Electroenzymatic Glucose Electrode is Markedly Impaired in Human Sub-Cutaneous Tissue and Plasma," Biosensors and Bioelectronics, vol. 8, 1993, pp. 473-482.

Kerner W., "Implantable Glucose Sensors: Present Status and Future Developments," Experimental and Clinical Endocrinol Diabetes, vol. 109 (2), 2001, pp. S341-S346.

Klonoff D., et al., "Performance Metrics for Continuous Interstitial Glucose Monitoring; Approved Guideline," Clinical and Laboratory Standards Institute, POCT05-A, vol. 28 (33), 2008, 72 pages.

Klueh U., et al., "Use of Vascular Endothelial Cell Growth Factor Gene Transfer to Enhance Implantable Sensor Function in Vivo," Biosensor Function and VEGF-Gene Transfer, vol. 67 (4), 2003, pp. 1072-1086.

(56)    References Cited

OTHER PUBLICATIONS

Kondo T., et al., "A Miniature Glucose Sensor, Implantable in the Blood Stream," Diabetes Care, vol. 5 (3), May-Jun. 1982, 218-221.

Koschinsky T., et al., "Sensors For Glucose Monitoring: Technical And Clinical Aspects," Diabetes Metabolism Research and Reviews, vol. 17, 2001, pp. 113-123.

Koschinsky T., et al., "New Approach to Technical and Clinical Evaluation of Devices for Self-Monitoring of Blood Glucose," Diabetes Care, vol. 11 (8), Sep. 1988, pp. 619-629.

Kost J., et al., "Glucose-Sensitive Membranes Containing Glucose Oxidase: Activity, Swelling, And Permeability Studies," Journal of Biomedical Materials Research, vol. 19, 1985, pp. 1117-1133.

Koudelka M., et al., "In Vivo Response of Microfabricated Glucose Sensors to Glycemia Changes in Normal Rats," Biomed. Biochim. Acta, vol. 48 (11/12), Nov.-Dec. 1989, pp. 953-956.

Koudelka M., et al., "In-Vivo Behaviour of Hypodermically Implanted Microfabricated Glucose Sensors," Biosensors and Bioelectronics, vol. 6, 1991, pp. 31-36.

Kovatchev B.P., et al., "Evaluating the Accuracy of Continuous Glucose-Monitoring Sensors: Continuous Glucose-Error Grid Analysis Illustrated by TheraSense Freestyle Navigator Data," Diabetes Care, vol. 27 (8), Aug. 2004, pp. 1922-1928.

Kraver., et al., "A Mixed-Signal Sensor Interface Microinstrument," Sensors and Actuators A, Physical 2001, vol. 91, pp. 266-277.

Krouwer J.S., "Setting Performance Goals and Evaluating Total Analytical Error for Diagnostic Assays," Clinical Chemistry, vol. 48 (6), 2002, pp. 919-927.

Kruger D., et al., "Psychological Motivation and Patient Education: A Role for Continuous Glucose Monitoring," Diabetes Technology and Therapeutics, vol. 2 (1), 2000, pp. S93-S97.

Kulys J., et al., "Carbon-Paste Biosensors Array for Long-Term Glucose Measurement," Biosensors & Bioelectronics, vol. 9, 1994, pp. 491-500.

Kunjan K., et al., "Automated Blood Sampling and Glucose Sensing in Critical Care Settings," Journal of Diabetes Science and Technology, vol. 2 (2), Mar. 2008, pp. 194-200.

Kurnik R.T., et al., "Application of the Mixtures of Experts Algorithm for Signal Processing in a Noninvasive Glucose Monitoring System," Sensors and Actuators B, vol. 60, 1999, pp. 19-26.

Kurtz T.W., et al., "Recommendations for Blood Pressure Measurement in Humans and Experimental Animals, Part 2: Blood Pressure Measurement In Experimental Animals: A Statement for Professionals From the Subcommittee of Professional and Public Education of the American Heart Association Council on High Blood Pressure Research," Hypertension, Feb. 2005, vol. 45, pp. 299-310.

Lacourse W.R., et al., "Optimization of Waveforms for Pulsed Amperometric Detection of Carbohydrates Based on Pulsed Voltammetry," Analytical Chemistry, vol. 65, 1993, pp. 50-52.

Ladd M.F.C., et al., "Structure Determination By X-Ray Crystallography," 3rd Edition, Plenum Press, 1994, Ch. 1, pp. xxi-xxiv and 1-58.

Lehmann E.D., et al., Retrospective Validation of a Physiological Model of Glucose-Insulin Interaction in Type 1 Diabetes Mellitus. Medical Engineering & Physics, vol. 16, May 1994, pp. 193-202.

Lerner., et al., "An Implantable Electrochemical Glucose Sensor," Ann. N. Y. Acad. Sci., vol. 428, May 1984, pp. 263-278.

Lewandowski J.J., et al., "Evaluation of a Miniature Blood Glucose Sensor," Transactions—American Society for Artificial Internal Organs, vol. 34, 1988, pp. 255-258.

Leypoldt J.K., et al., "Model of a Two-Substrate Enzyme Electrode for Glucose," Analytical Chemistry, vol. 56, 1984, pp. 2896-2904.

Linke B., et al., "Amperometric Biosensor for In Vivo Glucose Sensing Based on Glucose Oxidase Immobilized In A Redox Hydrogel," Biosensors and Bioelectronics, vol. 9, 1994, pp. 151-158.

Lohn A., et al., "A Knowledge-Based System for Real-Time Validation of Calibrations and Measurements," Chemometrics and Intelligent Laboratory Systems, vol. 46, 1999, pp. 57-66.

Lowe C.R., "Biosensors," Trends in Biotechnology, vol. 2 (3), 1984, pp. 59-65.

Luong J.H.T., et al., "Solubilization of Multiwall Carbon Nanotubes by 3-Aminopropyltriethoxysilane towards the Fabrication of Electrochemical Biosensors with Promoted Electron Transfer," Electroanalysis, vol. 16 (1-2), 2004, pp. 132-139.

Lyandres O., et al. "Progress toward an In Vivo Surface-Enhanced Raman Spectroscopy Glucose Sensor," Diabetes Technology and Therapeutics, vol. 10 (4), 2008, pp. 257-265.

Lynch S.M., et al., "Estimation-Based Model Predictive Control of Blood Glucose in Type I Diabetics: A Simulation Study," Proceedings of the IEEE 27th Annual Northeast Bioengineering Conference, 2001, pp. 79-80.

Lynn P.A., "Recursive Digital Filters for Biological Signals," Med. & Biol. Engineering, vol. 9, 1971, pp. 37-43.

Maidan R., et al., "Elimination of Electrooxidizable Interferent-Produced Currents in Amperometric Biosensors," Analytical Chemistry, vol. 64, 1992, pp. 2889-2896.

Makale M.T., et al., "Tissue Window Chamber System for Validation of Implanted Oxygen Sensors," American Journal of Physiology-Heart and Circulatory Physiology, vol. 284, Feb. 21, 2003, pp. 1-27.

Malin S.F., et al., "Noninvasive Prediction of Glucose by Near-Infrared Diffuse Reflectance Spectroscopy," Clinical Chemistry, vol. 45 (9), 1999, pp. 1651-1658.

Mancy K.H., et al., "A Galvanic Cell Oxygen Analyzer," Journal of Electroanalytical Chemistry, vol. 4, 1962, pp. 65-92.

Maran A., et al., "Continuous Subcutaneous Glucose Monitoring in Diabetic Patients," A Multicenter Analysis, Diabetes Care, vol. 25 (2), Feb. 2002, pp. 347-352.

March W.F., "Dealing with the Delay," Diabetes Technology & Therapeutics, vol. 4 (1), 2002, pp. 49-50.

Marena S., et al., "The Artificial Endocrine Pancreas in Clinical Practice and Research," Panminerva Medica, vol. 35 (2), 1993, pp. 67-74.

Martin R.F., "General Deming Regression for Estimating Systematic Bias and its Confidence Interval in Method-Comparison Studies," Clinical Chemistry, vol. 46 (1), 2000, pp. 100-104.

Mascini M., et al., "Glucose Electrochemical Probe with Extended Linearity for Whole Blood," Journal Pharmaceutical and Biomedical Analysis, vol. 7 (12), 1989, pp. 1507-1512.

Mastrototaro J.J., et al., "An Electroenzymatic Glucose Sensor Fabricated on a Flexible Substrate," Sensors and Actuators B, vol. 5, 1991, pp. 139-144.

Mastrototaro J.J., et al., "Reproducibility of the Continuous Glucose Monitoring System Matches Previous Reports and the Intended Use of the Product," Diabetes Care, vol. 26 (1), Jan. 2003, pp. 256-257.

Mastrototaro J.J., "The MiniMed Continuous Glucose Monitoring System," Diabetes Technology & Therapeutics, vol. 2, Supplement 1, 2000, pp. S13-18.

Matsuki H., "Energy Transfer System Utilizing Amorphous Wires For Implantable Medical Devices," IEEE Transactions on Magnetics, vol. 31 (2), 1994, pp. 1276-1282.

Matsumoto T., et al., "A Micro-Planar Amperometric Glucose Sensor Unsusceptible to Interference Species," Sensors and Actuators B, 49, 1998, pp. 68-72.

Matthews D.R., et al., "An Amperometric Needle-Type Glucose Sensor Testing in Rats and Man," Diabetic Medicine, vol. 5, 1988, pp. 248-252.

Mazze R.S., et al., "Characterizing Glucose Exposure for Individuals with Normal Glucose Tolerance Using Continuous Glucose Monitoring and Ambulatory Glucose Profile Analysis," Diabetes Technology & Therapeutics, vol. 10 (3), 2008, pp. 149-159.

Mazzola F., et al., "Video Diabetes: A Teaching Tool for Children with Insulin-Dependent Diabetes," IEEE, Proceedings 7th Annual Symposium on Computer Applications in Medical Care, Oct. 1983, 1 page Abstract.

McCartney L.J., et al., "Near-Infrared Fluorescence Lifetime Assay for Serum Glucose Based on Allophycocyanin-Labeled Concanavalin A," Analytical Biochemistry, vol. 292, 2001, pp. 216-221.

McGrath M.J., et al., "The Use of Differential Measurements with a Glucose Biosensor for Interference Compensation During Glucose Determinations by Flow Injection Analysis," Biosens Bioelectron, vol. 10, 1995, pp. 937-943.

(56)         References Cited

OTHER PUBLICATIONS

McKean B.D., et al., "A Telemetry Instrumentation System for Chronically Implanted Glucose and Oxygen Sensors," IEEE Transactions on Biomedical Engineering, vol. 35 (7), Jul. 1988, pp. 526-532.

Memoli A., et al., "A Comparison between Different Immobilised Glucoseoxidase-Based Electrodes," Journal of Pharmaceutical and Biomedical Analysis, vol. 29, 2002, pp. 1045-1052.

Merriam Webster Online Dictionary, Definition for "Aberrant," retrieved from https://www.merriam-webster.com/dictionary/aberrant, Aug. 19, 2008, 1 page.

Merriam-Webster Online Dictionary, Definition of "Acceleration" retrieved from http://www.merriam-webster.com/dictionary/Acceleration, Jan. 11, 2010, 1 page.

Merriam-Webster Online Dictionary, Definition of "Nominal" retrieved from http://www.merriam-webster.com/dictionary/nominal, Apr. 23, 2007, 1 page.

Merriam-Webster Online Dictionary, Definition of "System". http://www.merriamwebster.com/dictionary/System, Jan. 11, 2010, 2 pages.

Metzger M., et al., "Reproducibility of Glucose Measurements using the Glucose Sensor," Diabetes Care, vol. 25 (6), Jul. 2002, pp. 1185-1191.

Meyerhoff C., et al., "On Line Continuous Monitoring of Subcutaneous Tissue Glucose in Men by Combining Portable Glucosensor With Microdialysis," Diabetologia, vol. 35 (11), 1992, pp. 1087-1092.

Miller J.A., et al., "Development of an Autotuned Transcutaneous Energy Transfer System," ASAIO Journal, vol. 39, 1993, pp. M706-M710.

Moatti-Sirat D., et al., "Evaluating In Vitro and In Vivo the Interference of Ascorbate and Acetaminophen on Glucose Detection by a Needle-Type Glucose Sensor," Biosensors and Bioelectronics, vol. 7, 1992, pp. 345-352.

Moatti-Sirat D., et al., "Reduction of Acetaminophen Interference in Glucose Sensors by a Composite Nafion Membrane: Demonstration in Rats and Man," Diabetologia, vol. 37 (6), Jun. 1994, pp. 610-616.

Moatti-Sirat., et al., "Towards Continuous Glucose Monitoring: In Vivo Evaluation of a Miniaturized Glucose Sensor Implanted for Several Days in Rat Subcutaneous Tissue," Diabetologia, vol. 35, 1992, pp. 224-230.

Monsod T.P., et al., "Do Sensor Glucose Levels Accurately Predict Plasma Glucose Concentrations During Hypoglycemia And Hyperinsulinemia?, "Diabetes Care, vol. 25 (5), 2002, pp. 889-893.

Morff R.J., et al., "Microfabrication of Reproducible, Economical, Electroenzymatic Glucose Sensors," Annual International Conference of the IEEE Engineering in Medicine and Biology Society, vol. 12 (2), 1990, pp. 0483-0484.

Mosbach K., et al., "Determination of Heat Changes in the Proximity of Immobilized Enzymes with an Enzyme Thermistor and its Use for the Assay of Metabolites," Biochimica Biophysica Acta, vol. 403, 1975, pp. 256-265.

Motonaka J., et al., "Determination of Cholesterol and Cholesterol Ester with Novel enzyme Microsensors," Anal. Chem., vol. 65, 1993, pp. 3258-3261.

Moussy F., et al., "A Miniaturized Nafion-Based Glucose Sensor: In Vitro and In Vivo Evaluation in Dogs," International Journals of Artificial Organs, vol. 17 (2), 1994, pp. 88-94.

Murphy S.M., et al., "Polymer Membranes in Clinical Sensor Applications, II. The Design and Fabrication of Permselective Hydrogels for Electrochemical Devices," Biomaterials, 1992, vol. 13 (14), pp. 979-990.

Muslu, "Trickling Filter Performance," Applied Biochemistry and Biotechnology, vol. 37, 1992, pp. 211-224.

Neuburger G.G., et al., "Pulsed Amperometric Detection of Carbohydrates at Gold Electrodes with a Two-Step Potential Waveform," Anal. Chem., vol. 59, 1987, pp. 150-154.

Nintendo Healthcare, Wired, Dec. 1993, 1 page.

Novo Nordisk Pharmaceuticals Inc., "Diabetes Educational Video Game Recognized by Software Publishers Association," Press Release, Mar. 14, 1994, 4 pages.

Office Action for U.S. Appl. No. 09/636,369, mailed Sep. 30, 2002, 4 pages.

Office Action for U.S. Appl. No. 10/632,537, mailed Dec. 21, 2004, 7 pages.

Office Action for U.S. Appl. No. 10/632,537, mailed Oct. 20, 2004, 7 pages.

Office Action for U.S. Appl. No. 10/633,329, mailed Apr. 27, 2010, 5 pages.

Office Action for U.S. Appl. No. 10/633,329, mailed Dec. 18, 2008, 9 pages.

Office Action for U.S. Appl. No. 10/633,329, mailed Feb. 4, 2008, 7 pages.

Office Action for U.S. Appl. No. 10/633,329, mailed Jul. 30, 2007, 9 pages.

Office Action for U.S. Appl. No. 10/633,329, mailed Jun. 11, 2009, 8 pages.

Office Action for U.S. Appl. No. 10/633,329, mailed Jun. 12, 2008, 7 pages.

Office Action for U.S. Appl. No. 10/633,329, mailed Mar. 26, 2007, 05 pages.

Office Action for U.S. Appl. No. 10/633,329, mailed Oct. 5, 2006, 6 pages.

Office Action for U.S. Appl. No. 10/633,367, mailed Jul. 15, 2008, 8 pages.

Office Action for U.S. Appl. No. 10/633,367, mailed Jun. 11, 2009, 7 pages.

Office Action for U.S. Appl. No. 10/633,404, mailed Feb. 12, 2007, 14 pages.

Office Action for U.S. Appl. No. 10/648,849, mailed Jun. 23, 2009, 10 pages.

Office Action for U.S. Appl. No. 10/789,359, mailed Mar. 20, 2008, 7 pages.

Office Action for U.S. Appl. No. 10/789,359, mailed Nov. 27, 2006, 10 pages.

Office Action for U.S. Appl. No. 10/789,359, mailed Oct. 3, 2008, 7 pages.

Office Action for U.S. Appl. No. 10/838,909, mailed Jun. 5, 2008, 8 pages.

Office Action for U.S. Appl. No. 10/838,909, mailed Mar. 16, 2009, 12 pages.

Office Action for U.S. Appl. No. 10/991,966, mailed Jul. 22, 2008, 12 pages.

Office Action for U.S. Appl. No. 10/991,966, mailed Nov. 28, 2007, 13 pages.

Office Action for U.S. Appl. No. 11/007,920, mailed Jun. 24, 2008, 10 pages.

Office Action for U.S. Appl. No. 11/038,340, mailed Feb. 2, 2010, 18 pages.

Office Action for U.S. Appl. No. 11/038,340, mailed Jan. 5, 2009, 13 pages.

Office Action for U.S. Appl. No. 11/038,340, mailed Jun. 7, 2010, 18 pages.

Office Action for U.S. Appl. No. 11/038,340, mailed Jun. 17, 2008, 11 pages.

Office Action for U.S. Appl. No. 11/038,340, mailed May 19, 2009, 14 pages.

Office Action for U.S. Appl. No. 11/038,340, mailed Nov. 9, 2009, 16 pages.

Office Action for U.S. Appl. No. 11/077,739, mailed Dec. 29, 2009, 7 pages.

Office Action for U.S. Appl. No. 11/077,739, mailed Jul. 21, 2009, 8 pages.

Office Action for U.S. Appl. No. 11/077,739, mailed Mar. 1, 2010, 9 pages.

Office Action for U.S. Appl. No. 11/077,740, mailed Apr. 28, 2009, 27 pages.

Office Action for U.S. Appl. No. 11/077,740, mailed Feb. 7, 2008, 16 pages.

Office Action for U.S. Appl. No. 11/077,740, mailed Jul. 25, 2008, 24 pages.

Office Action for U.S. Appl. No. 11/077,740, mailed Jun. 1, 2007, 14 pages.

(56) References Cited

OTHER PUBLICATIONS

Office Action for U.S. Appl. No. 11/077,740, mailed Nov. 1, 2007, 13 pages.
Office Action for U.S. Appl. No. 11/077,759, mailed Jul. 10, 2008, 10 pages.
Office Action for U.S. Appl. No. 11/077,759, mailed Mar. 31, 2008, 16 pages.
Office Action for U.S. Appl. No. 11/077,759, mailed May 26, 2009, 8 pages.
Office Action for U.S. Appl. No. 11/077,765, mailed Dec. 31, 2007, 10 pages.
Office Action for U.S. Appl. No. 11/077,765, mailed Feb. 3, 2010, 10 pages.
Office Action for U.S. Appl. No. 11/077,765, mailed Jan. 23, 2009, 11 pages.
Office Action for U.S. Appl. No. 11/077,765, mailed May 16, 2008, 9 pages.
Office Action for U.S. Appl. No. 11/077,765, mailed Sep. 19, 2008, 9 pages.
Office Action for U.S. Appl. No. 11/334,876, mailed Aug. 25, 2009, 18 pages.
Office Action for U.S. Appl. No. 11/334,876, mailed Aug. 26, 2008, 8 pages.
Office Action for U.S. Appl. No. 11/334,876, mailed May 2, 2008, 18 pages.
Office Action for U.S. Appl. No. 11/334,876, mailed Oct. 4, 2006, 9 pages.
Office Action for U.S. Appl. No. 11/334,876, mailed Sep. 25, 2007, 14 pages.
Office Action for U.S. Appl. No. 11/360,252, mailed Jan. 29, 2009, 15 pages.
Office Action for U.S. Appl. No. 11/360,252, mailed Jul. 23, 2009, 10 pages.
Office Action for U.S. Appl. No. 11/360,252, mailed Jun. 30, 2008, 10 pages.
Office Action for U.S. Appl. No. 11/360,819, mailed Apr. 7, 2010, 10 pages.
Office Action for U.S. Appl. No. 11/360,819, mailed Aug. 11, 2008, 10 pages.
Office Action for U.S. Appl. No. 11/360,819, mailed Dec. 26, 2008, 12 pages.
Office Action for U.S. Appl. No. 11/360,819, mailed Oct. 29, 2009, 15 pages.
Office Action for U.S. Appl. No. 12/098,359, mailed Jul. 7, 2010, 18 pages.
Office Action for U.S. Appl. No. 12/102,654, mailed Jul. 30, 2009, 9 pages.
Office Action for U.S. Appl. No. 12/102,654, mailed Mar. 10, 2010, 6 pages.
Office Action for U.S. Appl. No. 12/102,745, mailed Dec. 23, 2008, 4 pages.
Office Action for U.S. Appl. No. 12/182,073, mailed Jun. 28, 2010, 20 pages.
Office Action for U.S. Appl. No. 12/182,083, mailed Jun. 24, 2010, 8 pages.
Office Action for U.S. Appl. No. 12/536,852, mailed Jun. 25, 2010, 8 pages.
Office Action for U.S. Appl. No. 95/001,038, mailed Jun. 17, 2008, 32 pages.
Office Action for U.S. Appl. No. 95/001,038, mailed May 28, 2010, 32 pages.
Office Action for U.S. Appl. No. 95/001,039, mailed May 29, 2008, 21 pages.
Ohara T.J., et al., "Glucose Electrodes Based On Cross-Linked [Os(bpy)2Cl](+/2+) Complexed Poly(1-Vinylimidazole) Films," Analytical Chemistry, vol. 65, Dec. 1993, pp. 3512-3517.
Ohara T.J., et al., ""Wired" Enzyme Electrodes for Amperometric Determination of Glucose or Lactate in the Presence of Interfering Substances," Anal Chem, vol. 66, 1994, pp. 2451-2457.

Okuda, et al., "Mutarotase Effect on Micro Determinations of D-Glucose and its Anomers with β D-Glucose Oxidase," Anal Biochem, vol. 43 (1), 1971, pp. 312-315.
Oxford English Dictionary Online, Definition of "Impending," http://www.askoxford.com/results/?view=devdict&field-12668446_Impending&branch=, Jan. 11, 2010, 1 page.
Palmisano F., et al., "Simultaneous Monitoring of Glucose and Lactate by an Interference and Cross-Talk Free Dual Electrode Amperometric Biosensor Based on Electropolymerized Thin Films," Biosensors & Bioelectronics, vol. 15, 2000, pp. 531-539.
Panteleon A.E., et al., "The Role of the Independent Variable to Glucose Sensor Calibration," Diabetes Technology & Therapeutics, vol. 5 (3), 2003, pp. 401-410.
Parker R.S., et al., "A Model-Based Algorithm for Blood Glucose Control In Type I Diabetic Patients," IEEE Trans Biomed Engg (BME), vol. 46(2), 1999, pp. 148-157.
Patel H., et al., "Amperometric Glucose Sensors Based on Ferrocene Containing Polymeric Electron Transfer Systems—A Preliminary Report," Biosensors & Bioelectronics, vol. 18, 2003, pp. 1073-1076.
Peacock W.F., et al., "Cardiac Troponin and Outcome in Acute Heart Failure," N. Engl. J. Med., vol. 358, 2008, pp. 2117-2126.
Pfeiffer E.F., et al., "On Line Continuous Monitoring of Subcutaneous Tissue Glucose is Feasible by Combining Portable Glucosensor with Microdialysis," Horm. Metab. Res., vol. 25, 1993, pp. 121-124.
Pfeiffer E.F., "The Glucose Sensor: The Missing Link in Diabetes Therapy," Horm Metab Res Suppl., vol. 24, 1990, pp. 154-164.
Phillips R.P., "A High Capacity Transcutaneous Energy Transmission System," ASIAO Journal, vol. 41, 1995, pp. M259-M262.
Pichert J.W., et al., "Issues for the Coming Age of Continuous Glucose Monitoring," Diabetes Educator, vol. 26 (6), Nov.-Dec. 2000, pp. 969-980.
Pickup J.C., et al., "Developing Glucose Sensors for In Vivo Use," Elsevier Science Publishers Ltd (UK), Tibtech, vol. 11, 1993, pp. 285-291.
Pickup J.C., et al., "Implantable Glucose Sensors: Choosing the Appropriate Sensor Strategy," Biosensors, vol. 3, (1987/1988), pp. 335-346.
Pickup J.C., et al., "In Vivo Molecular Sensing in Diabetes Mellitus: An Implantable Glucose Sensor with Direct Electron Transfer," Diabetologia, vol. 32, 1989, pp. 213-217.
Pickup J.C., et al., "Potentially-Implantable, Amperometric Glucose Sensors with Mediated Electron Transfer: Improving the Operating Stability," Biosensors, vol. 4, 1989, pp. 109-119.
Pickup J.C., et al., "Responses and Calibration of Amperometric Glucose Sensors Implanted in the Subcutaneous Tissue of Man," ACTA Diabetol, vol. 30, 1993, pp. 143-148.
Pinner S.H., et al., "Cross-Linking of Cellulose Acetate by Ionizing Radiation," Nature, vol. 184, Oct. 24, 1959, pp. 1303-1304.
Pishko M.V., et al., "Amperometric Glucose Microelectrodes Prepared Through Immobilization of Glucose Oxidase in Redox Hydrogels," Analytical Chemistry, vol. 63 (20), 1991, pp. 2268-2272.
Pitzer K.R., et al., "Detection of Hypogylcemia with the Glucowatch Biographer," Diabetes Care, vol. 24 (5), 2001, pp. 881-885.
Poirier J.Y., et al., "Clinical and Statistical Evaluation of Self-Monitoring Blood Glucose Meters," Diabetes Care, vol. 21 (11), Nov. 1998, pp. 1919-1924.
Poitout V., et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, vol. 36, 1993, pp. 658-663.
Poitout V., et al., "Development of a Glucose Sensor for Glucose Monitoring in Man: The Disposable Implant Concept," Clinical Materials, vol. 15, 1994, pp. 241-246.
Poitout V., et al., "In Vitro and In Vivo Evaluation in Dogs of a Miniaturized Glucose Sensor," ASAIO Transactions, vol. 37, 1991, pp. M298-M300.
Postlethwaite T.A., et al., "Interdigitated Array Electrode as an Alternative to the Rotated Ring-Disk Electrode for Determination of the Reaction Products of Dioxygen Reduction," Analytical Chemistry, vol. 68 (17), Sep. 1996, pp. 2951-2958.

(56) References Cited

OTHER PUBLICATIONS

Prabhu V.G., et al., "Electrochemical Studies of Hydrogen Peroxide at a Platinum Disc Electrode," Electrochimica Acta, vol. 26 (6), 1981, pp. 725-729.

Quinn C.A.P., et al., "Biocompatible, Glucose-Permeable Hydrogel for In situ Coating of Implantable Biosensors," Biomaterials, vol. 18 (24), 1997, pp. 1665-1670.

Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.

Rabah M.A., et al., "Electrochemical Wear of Graphite Anodes During Electrolysis of Brine," Carbon, vol. 29 (2), 1991, pp. 165-171.

RAYA Systems Pioneers, "Raya Systems Pioneers Healthy Video Games," PlayRight, Nov. 1993, pp. 14-15.

Reach G., "A Method for Evaluating in vivo the Functional Characteristics of Glucose Sensors," Biosensors, vol. 2, 1986, pp. 211-220.

Reach G., et al., "Can Continuous Glucose Monitoring Be Used for the Treatment of Diabetes?," Analytical Chemistry, vol. 64 (6), Mar. 15, 1992, pp. 381A-386A.

Reach G., "Which Threshold to Detect Hypoglycemia? Value of Receiver-Operator Curve Analysis to Find a Compromise Between Sensitivity and Specificity," Diabetes Care, vol. 24 (5), May 2001, pp. 803-804.

Rebrin K., et al., "Automated Feedback Control of Subcutaneous Glucose Concentration in Diabetic Dogs," Diabetologia, vol. 32, 1989, pp. 573-576.

Rebrin K., et al., "Subcutaenous Glucose Monitoring by Means of Electrochemical Sensors: Fiction or Reality?," Journal of Biomedical Engineering, vol. 14, Jan. 1992, pp. 33-40.

Rebrin K., et al., "Subcutaneous Glucose Predicts Plasma Glucose Independent of Insulin: Implications for Continuous Monitoring," The American Physiological Society, vol. 277, 1999, pp. E561-E571.

Reush, "Organometallic Compounds," Chemical Reactivity, Virtual Textbook of Organic Chemistry, Retrieved from http://www.cem.msu.edu/-reuschlVirtualText/orgmetal.htm, 2004, pp. 1-16.

Rhodes R.K., et al., "Prediction of Pocket-Portable and Implantable Glucose Enzyme Electrode Performance from Combined Species Permeability and Digital Simulation Analysis," Analytical Chemistry, vol. 66 (9), May 1, 1994, pp. 1520-1529.

Rigla M., et al., "Real-Time Continuous Glucose Monitoring Together with Telemedical Assistance Improves Glycemic Control and Glucose Stability in Pump-Treated Patients," Diabetes Technology & Therapeutics, vol. 10 (3), 2008, pp. 194-199.

Rinken T., et al., "Calibration of Glucose Biosensors By Using Pre-Steady State Kinetic Data," Biosensors & Bioelectronics, vol. 13, 1998, pp. 801-807.

Rivers E.P., et al., "Central Venous Oxygen Saturation Monitoring in the Critically Ill Patient," Current Opinion in Critical Care, 2001, vol. 7, pp. 204-211.

Sakakida M., et al., "Development of Ferrocene-Mediated Needle-Type Glucose Sensor as a Measure of True Subcutaneous Tissue Glucose Concentrations," Artif. Organs Today, vol. 2 (2), 1992, pp. 145-158.

Sakakida M., et al., "Ferrocene-Mediated Needle Type Glucose Sensor Covered with Newly Designed Biocompatible Membrane," Sensors and Actuators B, vol. 13-14, 1993, pp. 319-322.

Salardi S., et al., "The Glucose Area Under the Profiles Obtained with Continuous Glucose Monitoring System Relationships with HbA1C in Pediatric Type 1 Diabetic Patients," Diabetes Care, vol. 25 (10), Oct. 2002, pp. 1840-1844.

San Diego Plastics Inc, "Polyethylene," Datasheet, Retrieved from http://www.sdplastics.com/polyeth.html on Aug. 19, 2009, 7 pages.

Sansen W., et al., "A Smart Sensor for the Voltammetric Measurement of Oxygen or Glucose Concentrations," Sensors and Actuators B1, 1990, pp. 298-302.

Sansen W., et al., "Glucose Sensor with Telemetry System," In Implantable Sensors for Closed Loop Prosthetic Systems edited by Ko W.H, Chapter 12, 1985, pp. 167-175.

Schmidt F.J., et al., "Calibration of a Wearable Glucose Sensor," The International Journal of Artificial Organs, Wichtig Publishing, IT, vol. 15 (1), Jan. 1, 1992, pp. 55-61.

Schmidt F.J., et al., "Glucose Concentration in Subcutaneous Extracellular Space," Diabetes Care, vol. 16 (5), May 1993, pp. 695-700.

Schmidtke D.W., et al., "Accuracy of the One-Point in Vivo Calibration of "Wired" Glucose Oxidase Electrodes Implanted in Jugular Veins of Rats in Periods of Rapid Rise and Decline of the Glucose Concentration," Analytical Chemistry, vol. 70 (10), May 15, 1998, pp. 2149-2155.

Schmidtke D.W., et al., "Measurement and Modeling of the Transient Difference Between Blood and Subcutaneous Glucose Concentrations in the Rat After Injection of Insulin," Proceedings of the National Academy of Sciences, vol. 95, Jan. 1998, pp. 294-299.

Schoemaker M., et al., "The SCGMI System: Subcutaneous Continuous Glucose Monitoring Based on Microdialysis Technique," Diabetes Technology & Therapeutics, vol. 5 (4), 2003, pp. 599-608.

Schoonen A.J.M., et al., "Development of a Potentially Wearable Glucose Sensor for Patients with Diabetes Mellitus: Design and In-vitro Evaluation," Biosensors & Bioelectronics, vol. 5, 1990, pp. 37-46.

Service F.J., et al., "Mean Amplitude of Glycemic Excursions, A Measure of Diabetic Instability," Diabetes, vol. 19 (9), Sep. 1970, pp. 644-655.

Service F.J., et al., "Measurements of Glucose Control," Diabetes Care, vol. 10 (2), Mar.-Apr. 1987, pp. 225-237.

Service R.F., "Can Sensors Make a Home in the Body?," Science, Materials Science: Soft Surface, vol. 297, Aug. 9, 2002, pp. 962-963.

Sharkawy A.A., et al., "Engineering the Tissue Which Encapsulates Subcutaneous Implants. I. Diffusion Properties," Journal of Biomedical Materials Research, vol. 37, 1997, pp. 401-412.

Shaw G.W., et al., "In Vitro Testing of a Simply Constructed, Highly Stable Glucose Sensor Suitable for Implantation in Diabetic Patients," Biosensors & Bioelectronics, vol. 6, 1991, pp. 401-406.

Shichiri M., et al., "Glycaemic Control in Pancreatectomized Dogs with a Wearable Artificial Endocrine Pancreas," Diabetologia, vol. 24, 1983, pp. 179-184.

Shichiri M., et al., "Membrane Design for Extending the Long-Life of an Implantable Glucose Sensor," Diabetes Nutrition & Metabolism, vol. 2 (4), 1989, pp. 309-313.

Shichiri M., et al., "Needle Type Glucose Sensor for Wearable Artificial Endocrine Pancreas," In Implantable Sensors for Closed-Loop Prosthetic Systems edited by Ko W.H, Chapter 15, 1985, pp. 197-210.

Shichiri M., et al., "Telemetry Glucose Monitoring Device with Needle-Type Glucose Sensor: A Useful Tool for Blood Glucose Monitoring in Diabetic Individuals," Diabetes Care, vol. 9 (3), May-Jun. 1986, pp. 298-301.

Shichiri M., et al., "Wearable Artificial Endocrine Pancreas with Needle-Type Glucose Sensor," Preliminary Communication, Lancet, vol. 2, Nov. 20, 1982, pp. 1129-1131.

Shults M.C., et al., "A Telemetry-Instrumentation System for Monitoring Multiple Subcutaneously Implanted Glucose Sensors," IEEE Transactions on Biomedical Engineering, vol. 41 (10), Oct. 1994, pp. 937-942.

Sigma-Aldrich Corp "Nafion® 117 Solution Product Description, Product No. 70160," retrieved from https//:www.sigmaaldrich.com/cgi-bin/hsrun/Suite7/Suite/HAHTpage/Suite.HsExternalProd on Apr. 7, 2005, 1 page.

Skyler J.S., "The Economic Burden of Diabetes and the Benefits of Improved Glycemic Control: The Potential Role of a Continuous Glucose Monitoring System," Diabetes Technology & Therapeutics, vol. 2, Supplement 1, 2000, pp. S7-S12.

Slater-Maclean L., et al., "Accuracy of Glycemic Measurements in the Critically Ill," Diabetes Technology and Therapeutics, vol. 10 (3), 2008, pp. 169-177.

(56)             References Cited

OTHER PUBLICATIONS

Smith B., et al., "An Externally Powered, Multichannel, Implantable Stimulator-Telemeter for Control of Paralyzed Muscle," IEEE Transactions on Biomedical Engineering, vol. 45 (4), Apr. 1998, pp. 463-475.

Sokol L., et al., "Immobilized-Enzyme Rate-Determination Method for Glucose Analysis," Clinical Chemistry, vol. 26 (1), 1980, pp. 89-92.

Sokolov S., et al., "Metrological Opportunities of the Dynamic Mode of Operating an Enzyme Amperometric Biosensor," Medical Engineering & Physics, vol. 17 (6), 1995, pp. 471-476.

Sparacino G., et al., "Continuous Glucose Monitoring Time Series and Hypo-Hyperglycemia Prevention: Requirements, Methods, Open Problems," Current Diabetes Reviews, vol. 4 (3), 2008, pp. 181-192.

Sproule B.A., et al., "Fuzzy Pharmacology: Theory and Applications," Trends in Pharmacological Sciences, vol. 23 (9), Sep. 2002, pp. 412-417.

Sriyudthsak M., et al., "Enzyme-Epoxy Membrane Based Glucose Analyzing System and Medical Applications," Biosensors & Bioelectronics, vol. 11 (8), 1996, pp. 735-742.

Steil G.M., et al., "Determination of Plasma Glucose During Rapid Glucose Excursions with a Subcutaneous Glucose Sensor," Diabetes Technology & Therapeutics, vol. 5 (1), 2003, pp. 27-31.

Stern M., et al., "Electrochemical Polarization: I. A Theoretical Analysis of the Shape of Polarization Curves," Journal of the Electrochemical Society, vol. 104 (1), Jan. 1957, pp. 56-63.

Sternberg F., et al., "Does Fall in Tissue Glucose Precede Fall in Blood Glucose?," Diabetologia, vol. 39, 1996, pp. 609-612.

Sternberg R., et al., "Study and Development of Multilayer Needle-type Enzyme Based Glucose Microsensors," Biosensors, vol. 4, 1988, pp. 27-40.

Street J.O., et al., "A Note on Computing Robust Regression Estimates Via Iteratively Reweighted Least Squares," The American Statistician, vol. 42 (2), May 1988, pp. 152-154.

Sumino T., et al., "Preliminary Study of Continuous Glucose Monitoring with a Microdialysis Technique," Proceedings of the 20th Annual International Conference of the IEEE Engineering in Medicine and Biology Society, vol. 20 (4), 1998, pp. 1775-1778.

Takegami S., et al., "Pervaporation of Ethanol/Water Mixtures Using Novel Hydrophobic Membranes Containing Polydimethylsiloxane," Journal of Membrane Science, vol. 75, 1992, pp. 93-105.

Tamura T., et al., "Preliminary Study of Continuous Glucose Monitoring with a Microdialysis Technique and a Null Method—A Numerical Analysis," Frontiers of Medical & Biological Engineering, vol. 10 (2), 2000, pp. 147-156.

Tanenberg R.J., et al., "Continuous Glucose Monitoring System: A New Approach to the Diagnosis of Diabetic Gastroparesis," Diabetes Technology & Therapeutics, vol. 2, Supplement 1, 2000, pp. S73-S80.

Tatsuma T., et al., "Oxidase/Peroxidase Bilayer-Modified Electrodes as Sensors for Lactate, Pyruvate, Cholesterol and Uric Acid," Analytica Chimica Acta, vol. 242, 1991, pp. 85-89.

Thome V., et al., "(Abstract) Can the Decrease in Subcutaneous Glucose Concentration Precede the Decrease in Blood Glucose Level? Proposition for a Push-Pull Kinetics Hypothesis," Horm. metab. Res., vol. 27, 1995, p. 53.

Thome-Duret V., et al., "Continuous Glucose Monitoring in the Free-Moving Rat," Metabolism, vol. 47 (7), Jul. 1998, pp. 799-803.

Thome-Duret V., et al., "Modification of the Sensitivity of Glucose Sensor Implanted into Subcutaneous Tissue," Diabetes & Metabolism, vol. 22, 1996, pp. 174-178.

Thome-Duret V., et al., "Use of a Subcutaneous Glucose Sensor to Detect Decreases in Glucose Concentration Prior to Observation in Blood," Analytical Chemistry, vol. 68 (21), Nov. 1, 1996, pp. 3822-3826.

Thompson M., et al., "In Vivo Probes: Problems and Perspectives," Clinical Biochemistry, vol. 19 (5), Oct. 1986, pp. 255-261.

Tierney M.J., et al., "Effect of Acetaminophen on the Accuracy of Glucose Measurements Obtained with the GlucoWatch Biographer," Diabetes Technology & Therapeutics, vol. 2 (2), 2000, pp. 199-207.

Tierney M.J., et al., "The Gluco Watch® Biographer: A Frequent, Automatic and Noninvasive Glucose Monitor," Annals of Medicine, vol. 32, 2000, pp. 632-641.

Tilbury J.B., et al., "Receiver Operating Characteristic Analysis for Intelligent Medical Systems—A New Approach for Finding Confidence Intervals," IEEE Transactions on Biomedical Engineering, vol. 47 (7), Jul. 2000, pp. 952-963.

Torjman M.C., et al., "Glucose Monitoring in Acute Care: Technologies on the Horizon," Journal of Diabetes Science and Technology, vol. 2 (2), Mar. 2008, pp. 178-181.

Trajanoski Z., et al., "Neural Predictive Controller For Insulin Delivery Using The Subcutaneous Route," IEEE Transactions on Biomedical Engineering, vol. 45(9), 1998, pp. 1122-1134.

Trecroci D., "A Glimpse into the Future-Continuous Monitoring of Glucose with a Microfiber," Diabetes Interview, Jul. 2002, pp. 42-43.

Tse P.S.H., et al., "Time-Dependent Inactivation of Immobilized Glucose Oxidase and Catalase," Biotechnology & Bioengineering, vol. 29, 1987, pp. 705-713.

Turner A.P.F., et al., "Carbon Monoxide: Acceptor Oxidoreductase from Pseudomonas Thermocarboxydovorans Strain C2 and its Use in a Carbon Monoxide Sensor," Analytica Chimica Acta, vol. 163, 1984, pp. 161-174.

Turner A.P.F., et al., "Diabetes Mellitus: Biosensors for Research and Management," Biosensors, vol. 1, 1985, pp. 85-115.

Unger J., et al., "Glucose Control in the Hospitalized Patient," Emergency Medicine, vol. 36 (9), 2004, pp. 12-18.

Updike S.J., et al., "A Subcutaneous Glucose Sensor with Improved Longevity, Dynamic Range, and Stability of Calibration," Diabetes Care, vol. 23 (2), Feb. 2000, pp. 208-214.

Updike S.J., et al., "Continuous Glucose Monitor Based on an Immobilized Enzyme Electrode Detector," Journal of Laboratory and Clinical Medicine, vol. 93(4), 1979, pp. 518-527.

Updike S.J., et al., "Enzymatic Glucose Sensor: Improved Long-Term Performance in Vitro and In Vivo," ASAIO Journal, vol. 40 (2), Apr.-Jun. 1994, pp. 157-163.

Updike S.J., et al., "Implanting the Glucose Enzyme Electrode: Problems, Progress, and Alternative Solutions," Diabetes Care, vol. 5 (3), May-Jun. 1982, pp. 207-212.

Updike S.J., et al., "Laboratory Evaluation of New Reusable Blood Glucose Sensor," Diabetes Care, vol. 11 (10), Nov.-Dec. 1988, pp. 801-807.

Updike S.J., et al., "Principles of Long-Term Fully Implanted Sensors with Emphasis on Radiotelemetric Monitoring of Blood Glucose Form Inside a Subcutaneous Foreign Body Capsule (FBC)," Edited by Fraser D M, Biosensors in the Body: Continuous in vivo Monitoring, John Wiley & Sons Ltd., New York, 1997, Chapter 4, pp. 117-137.

Updike S.J., et al., "The Enzyme Electrode," Nature, vol. 214, Jun. 3, 1967, pp. 986-988.

Utah Medical Products Inc., "Deltran—Disposable Blood Pressure Tranducers," Product Specifications, 2003-2006, 6 pages.

Vadgama P., "Diffusion Limited Enzyme Electrodes," NATO ASI Series: Series C, Math and Phys. Sci, vol. 226, 1988, pp. 359-377.

Vadgama P., "Enzyme Electrodes as Practical Biosensors," Journal of Medical Engineering & Technology, vol. 5 (6), Nov. 1981, pp. 293-298.

Valdes T.I., et al., "In Vitro and In Vivo Degradation of Glucose Oxidase Enzyme used for an Implantable Glucose Biosensor," Diabetes Technology & Therapeutics, vol. 2 (3), 2000, pp. 367-376.

Van Den Berghe, "Tight Blood Glucose Control with Insulin in "Real-Life" Intensive Care," Mayo Clinic Proceedings, vol. 79 (8), Aug. 2004, pp. 977-978.

Velho G., et al., "In Vitro and In Vivo Stability of Electrode Potentials in Needle-Type Glucose Sensors," Influence of Needle Material, Diabetes, vol. 38, Feb. 1989, pp. 164-171.

Velho G., et al., "Strategies for Calibrating a Subcutaneous Glucose Sensor," Biomed Biochim Acta, vol. 48 (11/12), 1989, pp. 957-964.

(56)          References Cited

OTHER PUBLICATIONS

Von Woedtke T., et al., "In Situ Calibration of Implanted Electro-chemical Glucose Sensors," Biomed. Biochim. Acta 48 Vol. 11/12, 1989, pp. 943-952.

Wagner, et al., "Continuous Amperometric Monitoring of Glucose in a Brittle Diabetic Chimpanzee with a Miniature Subcutaneous Electrode," Proc. Natl. Acad. Sci. USA, vol. 95, May 1998, pp. 6379-6382.

Wang J., et al., "Highly Selective Membrane-Free Mediator-Free Glucose Biosensor," Analytical Chemistry, vol. 66 (21), Nov. 1, 1994, pp. 3600-3603.

Wang X., et al., "Improved Ruggedness for Membrane-Based Amperometric Sensors using a Pulsed Amperometric Method," Analytical Chemistry, vol. 69 (21), Nov. 1, 1997, pp. 4482-4489.

Ward W.K., et al., "A New Amperometric Glucose Microsensor: In Vitro and Short-Term In Vivo Evaluation," Biosensors & Bioelectronics, vol. 17, 2002, pp. 181-189.

Ward W.K., et al., "Assessment of Chronically Subcutaneous Glucose Sensors in Dogs: The Effect of Surrounding Fluid Masses," ASAIO Journal, 1999, vol. 45 (6), pp. 555-561.

Ward W.K., et al., "Rise in Background Current Over Time in a Subcutaneous Glucose Sensor in the Rabbit," Relevance to Calibration and Accuracy, Biosensors & Bioelectronics, vol. 15, 2000, pp. 53-61.

Ward W.K., et al., "Understanding Spontaneous Output Fluctuations of an Amperometric Glucose Sensor: Effect of Inhalation Anesthesia and Use of a Nonenzyme Containing Electrode," ASAIO Journal, 2000, pp. 540-546.

Wientjes K.J.C., "Development of a Glucose Sensor for Diabetic Patients," (Ph.D. Thesis), 2000, 212 pages.

Wikipedia., "Intravenous Therapy," http://en.wikipedia.org/wiki/Intravenous_therapy, Aug. 15, 2006, 6 pages.

Wilkins E., et al., "Glucose Monitoring: State of the Art and Future Possibilities," Med. Eng. Phys., vol. 18 (4), 1996, pp. 273-288.

Wilkins E., et al., "Integrated Implantable Device for Long-Term Glucose Monitoring," Biosensors & Bioelectronics, vol. 10, 1995, pp. 485-494.

Wilkins E.S., et al., "The Coated Wire Electrode Glucose Sensor," Horm Metab Res Suppl., vol. 20, 1988, pp. 50-55.

Wilson G.S., et al., "Enzyme-Based Biosensors for In Vivo Measurements," Chem. Rev., vol. 100, 2000, pp. 2693-2704.

Wilson G.S., et al., "Progress Toward the Development of an Implantable Sensor for Glucose," Clinical Chemistry, vol. 38 (9), 1992, pp. 1613-1617.

Wood W D., et al., "Hermetic Sealing with Epoxy," Pave Technology-Mechanical Engineering, Mar. 1990, 3 pages.

Woodward S.C., "How Fibroblasts and Giant Cells Encapsulate Implants: Considerations in Design of Glucose Sensor," Diabetes Care, vol. 5 (3) May-Jun. 1982, pp. 278-281.

Worsley G.J et al., "Measurement of Glucose in Blood with a Phenylboronic Acid Optical Sensor," Journal of Diabetes Science and Technology, vol. 2 (2), Mar. 2008, pp. 213-220.

Wright M., et al., "Bioelectrochemical Dehalogenations Via Direct Electrochemistry of Poly(ethylene oxide)-Modified Myoglobin," Electrochemistry Communications, vol. 1, 1999, pp. 609-613.

Wu H., et al., "In Situ Electrochemical Oxygen Generation with an Immunoisolation Device," Annals New York Academy of Sciences, vol. 875, 1999, pp. 105-125.

Yamasaki Y., et al., "Direct Measurement of Whole Blood Glucose by a Needle-Type Sensor," Clinica Chimica Acta. 93, 1989, pp. 93-98.

Yamasaki Y., "The Development of a Needle-Type Glucose Sensor for Wearable Artificial Endocrine Pancreas," Medical Journal of Osaka University, vol. 35 (1-2), Sep. 1984, pp. 25-34.

Yang C., et al., "A Comparison of Physical Properties and Fuel Cell Performance of Nafion and Zirconium Phosphate/Nation Composite Membranes," Journal of Membrane Science, vol. 237, 2004, pp. 145-161.

Yang Q., et al., "Development of Needle-Type Glucose Sensor with High Selectivity," Science and Actuators B, vol. 46, 1998, pp. 249-256.

Yang S., et al., "A Glucose Biosensor Based On an Oxygen Electrode: In-Vitro Performances in a Model Buffer Solution and in Blood Plasma," Biomedical Instrumentation & Technology, vol. 30 (1), 1996, pp. 55-61.

Ye L., et al., "High Current Density Wired Quinoprotein Glucose Dehydrogenase Electrode," Analytical Chemistry, vol. 65, 1993, pp. 238-241.

Zamzow K.L., et al., "Development and Evaluation of a Wearable Blood Glucose Monitor," ASAIO Transactions, vol. 36 (3), 1990, pp. M588-M591.

Zavalkoff S.R., et al., "Evaluation Of Conventional Blood Glucose Monitoring as An Indicator of Integrated Glucose Values Using a Continuous Subcutaneous Sensor," Diabetes Care, vol. 25(9), 2002, pp. 1603-1606.

Zethelius B., et al., "Use Of Multiple Biomarkers to Improve the Prediction of Death From Cardiovascular Causes," N. Engl. J. Med., vol. 358, May 2008, pp. 2107-2116.

Zhang, et al., "Elimination of the Acetaminophen Interference in an Implantable Glucose Sensor," Analytical Chemistry, 1994, vol. 66 (7), pp. 1183-1188.

Zhang Y., et al., "Electrochemical Oxidation Of H2O2 On Pt and Pt + Ir Electrodes in Physiological Buffer and its Applicability to H2O2-Based Biosensors," J. Electro Analytical Chemistry, vol. 345, 1993, pp. 253-271.

Zhang Y., et al., "In Vitro and In Vivo Evaluation of Oxygen Effects on a Glucose Oxidase Based Implantable Glucose Sensor," Analytica Chimica Acta, vol. 281, 1993, pp. 513-520.

Zhu, et al., "Fabrication and Characterization of Glucose Sensors Based on a Microarray H2O2 Electrode," Biosensors & Bioelectronics, 1994, vol. 9, pp. 295-300.

Zhu, et al., "Planar Amperometric Glucose Sensor Based on Glucose Oxidase Immobilized by Chitosan Film on Prussian blue Layer," Sensors, 2002, vol. 2, pp. 127-136.

Ziaie, et al., "A Single-Channel Implantable Microstimulator for Functional Neuromuscular Stimulation," IEEE Transactions on Biomedical Engineering, 1997, vol. 44(10), pp. 909-920.

* cited by examiner

RETRIEVE SENSOR DATA — 111

SENSE AN INTERACTION — 113

TABULATE A SCORE — 115

DISPLAY AND/OR TRANSMIT A REWARD — 117

Figures 8A, 8B:
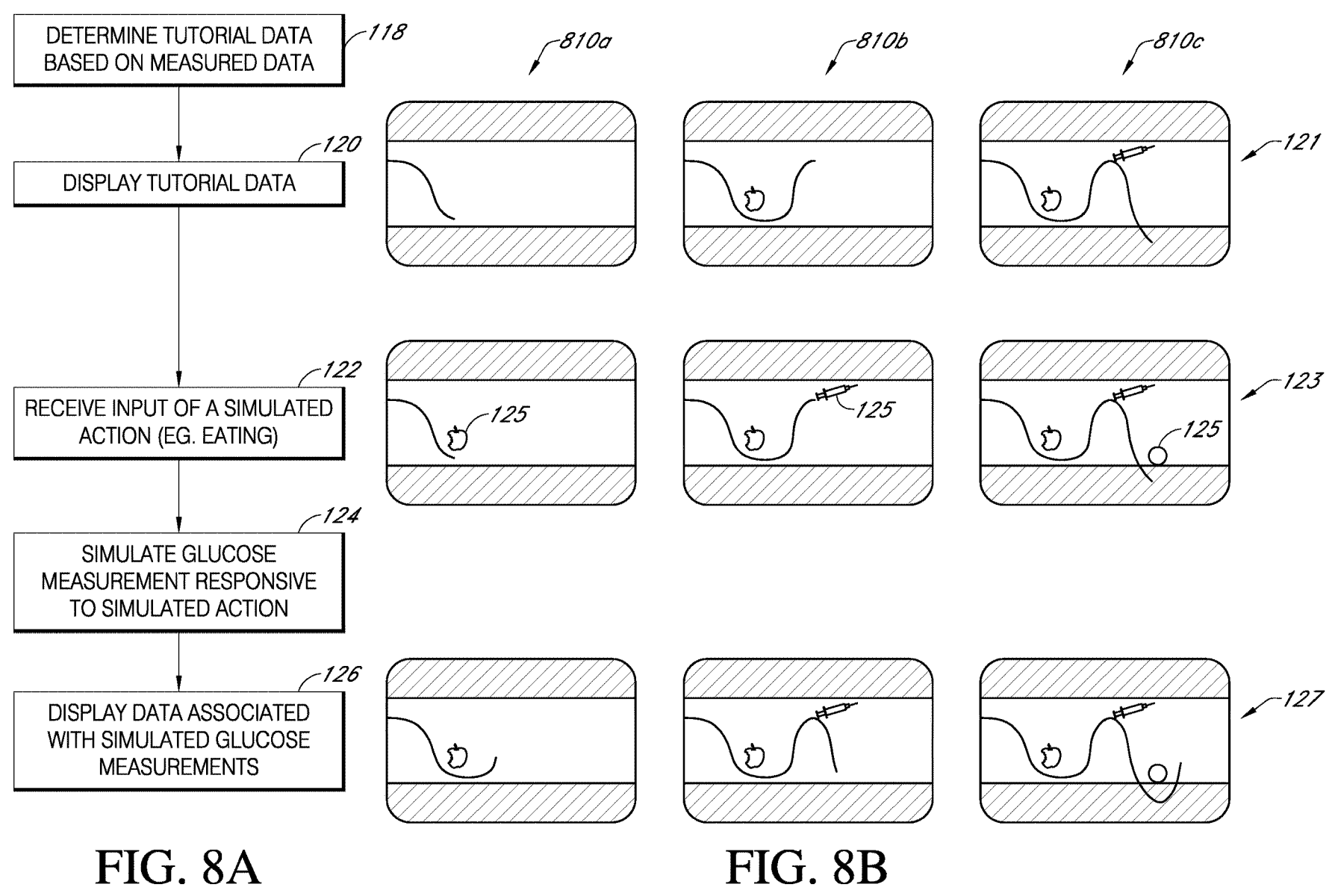

DETERMINE TUTORIAL DATA BASED ON MEASURED DATA — 118

DISPLAY TUTORIAL DATA — 120

RECEIVE INPUT OF A SIMULATED ACTION (EG. EATING) — 122

SIMULATE GLUCOSE MEASUREMENT RESPONSIVE TO SIMULATED ACTION — 124

DISPLAY DATA ASSOCIATED WITH SIMULATED GLUCOSE MEASUREMENTS — 126

METHODS AND SYSTEMS FOR PROMOTING GLUCOSE MANAGEMENT

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 14/971,886, filed Dec. 16, 2015, which is a continuation of U.S. application Ser. No. 14/144,489, filed on Dec. 30, 2013, which is a continuation of U.S. application Ser. No. 12/748,069, filed on Mar. 26, 2010, now U.S. Pat. No. 9,446,194, which claims priority to U.S. Provisional Application 61/164,326, filed on Mar. 27, 2009. Each of the aforementioned applications is incorporated by reference herein in its entirety, and each is hereby expressly made a part of this specification.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes will normally only measure his or her glucose levels two to four times per day. Unfortunately, these time intervals are so far apart that the person with diabetes will likely find out too late about hyper- or hypo-glycemic conditions. In fact, it is not only unlikely that a person with diabetes will take a timely SMBG value, it is likely that the person with diabetes will not know if their blood glucose value is going up (higher) or down (lower) based on conventional methods. Thus, their ability to make educated insulin therapy decisions is inhibited.

Some attempts have been made to continuously measure the glucose concentration in a person with diabetes. More frequent measurements can allow the person with diabetes to know of essentially current blood sugar conditions and to make appropriate decisions in response to the current conditions. However, these continuous glucose sensors typically use methods of displaying measurement data which is uninteresting to the person with diabetes. This is especially the case when the person with diabetes is young. Pediatric persons with diabetes often do not understand, forget about, or intentionally ignore the data displayed from their continuously measured glucose monitor. Accordingly, people with diabetes experience blood sugar excursions which may have been avoided had they been more diligently interacting with their sensor system.

Accordingly, there exists a need for improvements in displaying data from continuous glucose sensors in order to better entice the person with diabetes, such as pediatric patients, to use and interact with their monitor system.

SUMMARY

In one embodiment, the invention comprises a method of encouraging interactions with a receiver configured to receive sensor data from a glucose sensor. The method comprises sensing an interaction from a user with a receiver, wherein the receiver is configured to receive sensor data from the glucose sensor and to selectively display information associated with the sensor data and/or the sensor data in response to interactions from the user. In response to a plurality of different sensed interactions, a reward counter is incremented, and in response to determining that the reward counter has reached a predetermined reward threshold, a reward indication on the receiver is displayed, and/or a reward indication is transmitted.

In another embodiment, a method of encouraging interactions with a continuous glucose monitoring system comprises sensing a user interaction with a portion of the continuous glucose monitoring system and incrementing a reward counter in response to the sensed interaction independent of the creation or value of any sensor data.

In another embodiment, a portable sensor system is provided. The sensor system comprises a glucose sensor configured to provide real-time continuous glucose sensor data, a device comprising a user interface configured to receive user input and display the real time glucose sensor data responsive to user-interaction with the portable device, and a processor module configured to tabulate a score based at least in part on user interactions with the user interface.

BRIEF DESCRIPTION OF THE DRAWINGS

FIG. 8A is a flowchart that illustrates a process of displaying tutorial data for a user.

FIG. 8B illustrates exemplary frames of a tutorial.

DETAILED DESCRIPTION OF CERTAIN EMBODIMENTS

Figure 1:
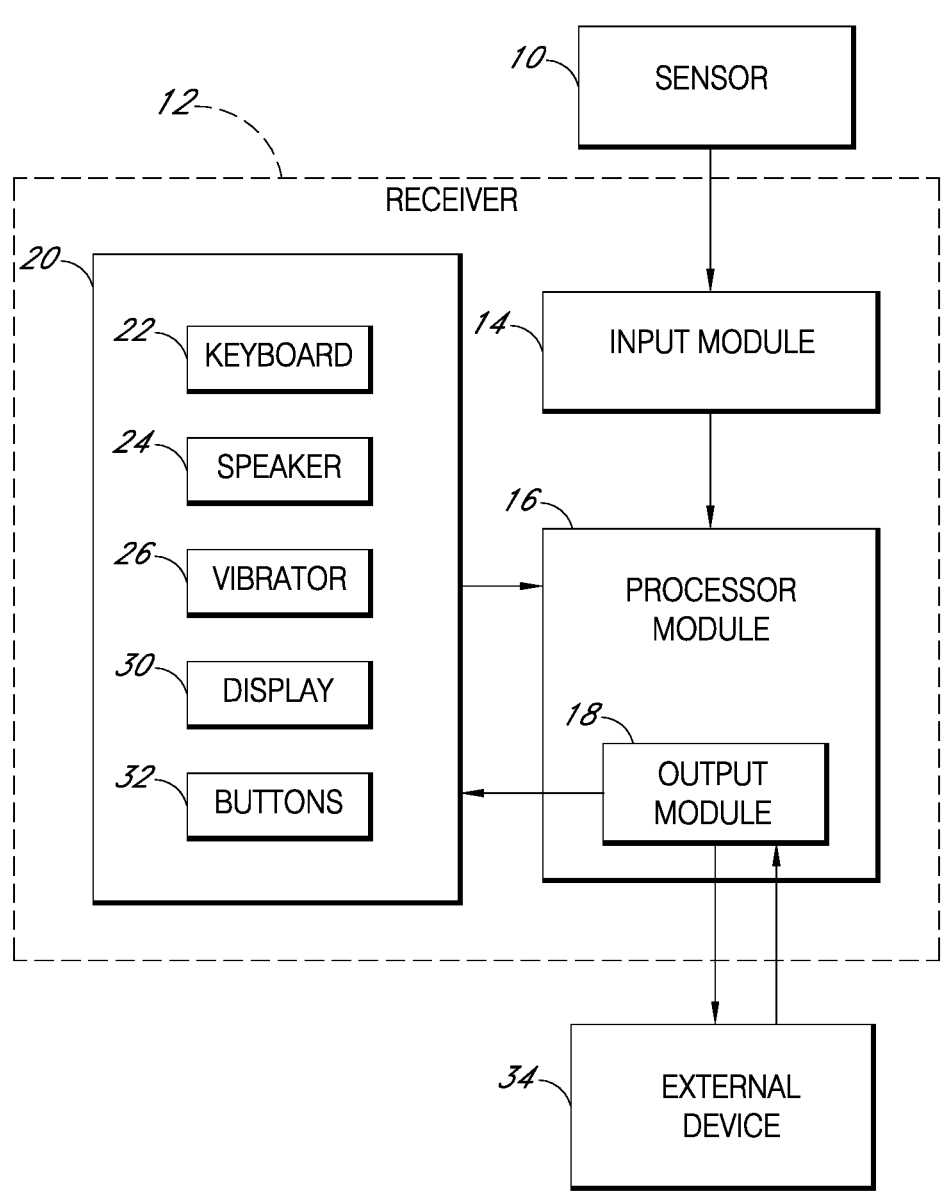
FIG. 1 is a block diagram that illustrates a configuration of a medical device in one embodiment, including a continuous analyte sensor, a receiver, and an external device.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "analyte," as used herein, is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "continuous analyte sensor," as used herein, is a broad term and is used in its ordinary sense, including, but not limited to, a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte sensing," as used herein, is a broad term and is used in its ordinary sense, including, but not limited to, monitoring of an analyte continuously, for example, at time intervals ranging from fractions of a second up to, for example, 1, 2, or 5 minutes, or longer.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "calibration" as used herein is a broad term and is to be given its ordinary and customary meaning to a person of ordinary skill in the art (and is not to be limited to a special or customized meaning), and furthermore refers without limitation to a process of determining a relationship between sensor data and corresponding reference data, which can be used to convert sensor data into calibrated data (defined below). In some embodiments, such as continuous analyte sensors, for example, calibration can be updated or recalibrated over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "time period," as used herein, is a broad term and is used in its ordinary sense, including, but not limited to, an amount of time including a single point in time and a path (for example, range of time) that extends from a first point in time to a second point in time.

The term "measured analyte values," as used herein, is a broad term and is used in its ordinary sense, including, but not limited to, an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The term "estimated analyte values," as used herein, is a broad term and is used in its ordinary sense, including, but not limited to, an analyte value or set of analyte values, which have been algorithmically extrapolated from measured analyte values. Typically, estimated analyte values are estimated for a time period during which no data exists. However, estimated analyte values can also be estimated during a time period for which measured data exists, but is to be replaced by algorithmically extrapolated data due to a time lag in the measured data, for example.

The term "alarm," as used herein, is a broad term and is used in its ordinary sense, including, but not limited to, audible, visual, or tactile signals that are triggered in response to detection of clinical risk to a patient. In one embodiment, hyperglycemic and hypoglycemic alarms are triggered when present or future clinical danger is assessed based on continuous analyte data.

The terms "target analyte values" and "analyte value goal," as used herein, are broad terms and are used in their ordinary sense, including, but not limited to, an analyte value or set of analyte values that are clinically acceptable. In one example, a target analyte value is visually or audibly presented to a patient in order to aid in guiding the patient in understanding how they should avoid a clinically risky analyte concentration.

The terms "therapy" and "therapy recommendations," as used herein, are broad terms and are used in their ordinary sense, including, but not limited to, the treatment of disease or disorder by any method. In one exemplary embodiment, a patient is prompted with therapy recommendations such as "inject insulin" or "consume carbohydrates" in order to avoid a clinically risky glucose concentration.

The term "computer," as used herein, is broad term and is used in its ordinary sense, including, but not limited to, machine that can be programmed to manipulate data.

The term "modem," as used herein, is a broad term and is used in its ordinary sense, including, but not limited to, an electronic device for converting between serial data from a computer and an audio signal suitable for transmission over a telecommunications connection to another modem.

The term "insulin pen," as used herein, is a broad term and is used in its ordinary sense, including, but not limited to, an insulin injection device generally the size of a pen that includes a needle and holds a vial of insulin. It can be used instead of syringes for giving insulin injections.

The term "insulin pump," as used herein, is a broad term and is used in its ordinary sense, including, but not limited to, a device that delivers a continuous supply of insulin into the body. The insulin flows from the pump through a plastic tube (called a catheter) that is connected to a needle inserted into the skin and taped in place, for example.

Overview

Certain embodiments provide a continuous analyte sensor that measures a concentration of analyte within a host and provides a data stream representative of the concentration of the analyte in the host, and a receiver that processes the data stream received from the analyte sensor for output as part of a user interface that is displayed on a display of the receiver, for example. In some embodiments, the analyte sensor is integral with the receiver, while in other embodiments, the analyte sensor is operatively linked to the receiver, for example, via a wired link or a wireless link.

Sensor data associated with a host may be displayed in a variety of manners that are interesting to the user, and are configured to motivate the user to interact with the receiver, for example, pediatric users. For example, the data may be depicted with graphical indicia so as to form a scene unrelated to glucose measurement. In some embodiments, the scene may form a real-life picture or an animation of an event. In some embodiments, the data may be depicted with an interactive animation, video game or cartoon. For example, the data may be depicted as a series of frames associated with a game or a cartoon that changes in accordance with changes in sensor data. The graphics displayed on the frames may include rewards based on actions taken by the user or based on sensor data. The data displayed may be used as a tutorial for educational interaction between the sensor system and the host. In some embodiments, data may be displayed with an avatar, an icon, or other character that is recognizable to the host. In some embodiments, therapy recommendations can be provided that are useful in guiding the host away from clinical risk. Interesting and/or intuitive display methods can help users to be more involved and aware of their glucose levels. This increased awareness provides the user with better recognition of current glucose trends and therefore better ability to react to and to control glucose excursions.

In some embodiments, the receiver casts diabetes management as a game in which users can earn and lose points according to their glycemic control over a length of time. The game may be played with instructions, such as "avoid glucose excursions outside target range for high score." Points may be earned for each sensor data point indicating a glucose level that falls within the target range. In some embodiments, points may be lost for each sensor data point indicating a glucose level above or below the target range. Scores may be tallied for a fixed period of time, such as 24 hours, 1 week, 1 month, 3 months or more, and compared from period to period. In some embodiments, the number of excursions that occur after a game begins may limit the duration of the game. For example, the user may be allowed 3 excursions before the game is over, at which time the final score is tallied. With improved scores, the target ranges may be tightened to encouraged further improvement. In some embodiments, game scores may be related to clinical measures of glycemic control, such as HbA1c, and provide users and their caregivers continuous assessment of their diabetes management.

In some embodiments, a receiver generates user interfaces that are based on and/or include real-time sensor data, such as measured analyte values, transformed sensor data, estimated analyte values, possible variations of estimated analyte values, targets or goals for analyte values, single-point values and/or the like. Additionally or alternatively, user interfaces and/or data that is useable to generate user interfaces, can be sent to a device external from the receiver, for example, a mobile computing device of a caretaker of the host, a computer, an electronic medical records system, a modem, or medical device. In some embodiments, input from the user or from another device, such as insulin injections (time and amount), meal times, exercise, personalized therapy recommendations, or the like, can be input into the receiver and processed to provide more customized data analysis and/or data output.

Accordingly, the systems and methods described herein display sensor data in such a way as to entice interaction between the user and the sensor system. This may increase the likelihood that the host will recognize that they are in a state, e.g., hypoglycemia or hyperglycemia, for which some action should be taken for their benefit.

Continuous Sensor

In some embodiments, a glucose sensor comprises an analyte sensor that measures a concentration of analyte of interest or a substance indicative of the concentration or presence of the analyte. A glucose sensor may use any known method, including invasive, minimally invasive, and non-invasive sensing techniques, to provide an output signal indicative of the concentration of the analyte of interest. In some embodiments, a glucose sensor comprises a continuous analyte sensor, for example a subcutaneous, transdermal, or intravascular device. In some embodiments, a glucose sensor can take a plurality of intermittent measurements. An analyte sensor can use any method of analyte-measurement, including enzymatic, chemical, physical, electrochemical, spectrophotometric, polarimetric, calorimetric, radiometric, or the like. Generally, an analyte sensor can be any sensor capable of determining the level of any analyte in the body, for example glucose, oxygen, lactase, hormones, cholesterol, medicaments, viruses, or the like. It should be understood that the devices and methods described herein can be applied to any device capable of continually or continuously detecting a concentration of analyte and providing an output signal that represents the concentration of that analyte.

In one embodiment, an analyte sensor is an implantable glucose sensor, such as described with reference to U.S. Pat. No. 6,001,067 and co-pending U.S. Patent Publication 2005/0027463 which are incorporated herein by reference in their entirety. In another embodiment, an analyte sensor is a transcutaneous glucose sensor, such as described with reference to U.S. Provisional Patent Application 60/587,787 and 60/614,683. In one alternative embodiment, the continuous glucose sensor comprises a transcutaneous sensor such as described in U.S. Pat. No. 6,565,509 to Say et al., for example. In another alternative embodiment, a continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, a continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al. All of the above patents are incorporated by reference herein in their entirety. Other signal processing techniques and glucose monitoring system embodiments suitable for use with the inventions described herein are also described in U.S. Patent Publications 2005/0203360 and 2009/0192745, both of which are incorporated herein by reference in their entireties.

FIG. 1 is a block diagram that illustrates a receiver 12 in communication with a sensor 10 and an external device 34. In general, the continuous analyte sensor 10 is any sensor configuration that provides an output signal indicative of a concentration of an analyte. The output signal (e.g., sensor data, such as a raw data stream, filtered data, smoothed data, and/or otherwise transformed sensor data) is sent to the receiver 12 and received by an input module 14, which is described in more detail below. The output signal may include a raw data stream that is used to provide a useful value of the measured analyte concentration to a patient or doctor, for example. In some embodiments, the sensor data from the sensor 10 can be continuously or periodically algorithmically smoothed, calibrated, or otherwise modified to diminish outlying points that do not accurately represent the analyte concentration, for example due to signal noise or other signal artifacts, such as described in co-pending U.S. Pat. No. 6,931,327, which is incorporated herein by reference in its entirety.

Receiver

Referring again to FIG. 1, the receiver 12, which is operatively linked to the sensor 10, receives a data stream from the sensor 10 via the input module 14. In one embodiment, the input module 14 includes a quartz crystal operably connected to an RF transceiver (not shown) that together function to receive and synchronize data streams from the sensor 10. However, the input module 14 can be configured in any manner that is capable of receiving data from the sensor. Once received, the input module 14 sends the data stream to a processor 16 that processes the data stream, such as described in more detail below.

The processor 16 is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, or the like. The processor includes hardware that performs the processing described herein, for example read-only memory (ROM) provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing.

An output module 18, which may be integral with and/or operatively connected with the processor 16, includes programming for generating output based on the sensor data received from the sensor 10 and its processing incurred in the processor 16. In some embodiments, output is generated via one or more input/output devices 20.

The input/output devices 20 of this embodiment comprise a keyboard 22, speaker 24, vibrator 26, backlight 28, display device 30, and one or more buttons 32. The components that comprise the input/output devices 20 include controls to allow interaction of the user with the receiver. The keyboard 22 can allow, for example, input of user information about himself/herself, such as mealtime, insulin and carbohydrate ratios, exercise, insulin administration, customized therapy recommendations, and reference analyte values. The speaker 24 can produce, for example, audible signals or alerts for conditions such as present and/or estimated hyper- and hypoglycemic conditions in a person with diabetes. The vibrator 26 can provide, for example, tactile signals or alerts for reasons such as described with reference to the speaker, above. In some embodiments, the display device 30 is a touch-sensitive screen. The buttons 32 can provide for toggle, menu selection, option selection, mode selection, and reset, for example. In some alternative embodiments, a microphone can be provided to allow for voice-activated control.

In some embodiments, analyte values are displayed on the display device 30. In some embodiments, prompts or messages can be displayed on the display device 30 to convey information to the user, such as reference outlier values, requests for reference analyte values, therapy recommendations, deviation of the measured analyte values from the estimated analyte values, or the like. Additionally, prompts can be displayed to guide the user through calibration or trouble-shooting of the calibration.

Additionally, data output from the output module 18 can provide wired or wireless, one- or two-way communication between the receiver 12 and an external device 34. The external device 34 can be any device that interfaces or communicates with the receiver 12. In some embodiments, the external device 34 is a computer, and the receiver 12 is able to download historical data for retrospective analysis by the physician, for example. In some embodiments, the external device 34 is a modem, and the receiver 12 is able to send alerts, warnings, emergency messages, or the like, via telecommunication lines to another party, such as a doctor or family member. In some embodiments, the external device 34 is an insulin pen, and the receiver 12 is able to communicate therapy recommendations, such as insulin amount and time to the insulin pen. In some embodiments, the external device 34 is an insulin pump, and the receiver 12 is able to communicate therapy recommendations, such as insulin amount and time to the insulin pump. The external device 34 can include other technology or medical devices, for example pacemakers, implanted analyte sensor patches, other infusion devices, telemetry devices, or the like. The receiver 12 may communicate with the external device 34, and/or any number of additional external devices, via any suitable communication protocol, including radio frequency, Bluetooth, universal serial bus, any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, and/or a proprietary communication protocol.

The input/output devices 20 including keyboard 22, buttons 32, a microphone (not shown), as well as the external device 34, can be configured to allow input of data. Data input can be helpful in obtaining information about the patient (for example, meal time, exercise, or the like), receiving instructions from a physician (for example, customized therapy recommendations, targets, or the like), and downloading software updates, for example. Keyboard, buttons, touch-screen, and microphone are all examples of mechanisms by which a user can input data directly into the receiver. A server, personal computer, personal digital assistant, insulin pump, and insulin pen are examples of external devices that can provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual.

In a further embodiment, input/output devices can be used to generate data for tracking physical exercise performed by the host. In this regard, a global positioning device (GPS) and/or accelerometer can be incorporated internally with or communicatively coupled externally to receiving unit 12 to provide positional and/or movement data of a host. Other sensors, such as a heart monitor, can also be used either alone or in combination with the GPS and accelerometer, to provide exercise-related data for tracking exercise performed by the host. In doing so, types of rewards and reward values can be tracked and awarded based partly or wholly on exercise performed by the host, as discussed in more detail later in this disclosure.

While a few examples of data input have been provided here, a variety of information can be input, which can be helpful in data processing as will be understood by one skilled in the art.

Customized User Interfaces Depicting Sensor Data

A data stream received from a continuous analyte sensor can provide an analyte value and/or other sensor data, and display the same to the host, which can be used to warn the host (or other interested party, such as a caretaker of the host or doctor) of existing clinical risk. A data stream received from an analyte sensor can provide historical trend analyte values, which can be used to educate a patient, caretaker, and/or doctor of individual historical trends of the patient's analyte concentration.

Sensor data may be displayed in such a way as to be more interesting to the user than a line graph, for example. In one embodiment, for example, sensor data may be depicted as a series of frames of a game, an animation, or a cartoon. The display may include rewards based on actions taken by the user or based on measurement data. The data displayed may be used as a tutorial for educational interaction between the sensor system and the user. In some embodiments, data may be displayed and/or otherwise conveyed (e.g., spoken instruction may be emitted from the speaker 24 of the receiver 12) by an avatar, an icon or a character depicted on the display device 30.

In some embodiments, receivers, such as receiver 12 of FIG. 1 have multiple games which can be selected by the user. In some embodiments, the game is selected randomly or pseudorandomly. Each game may have graphics which are used by the receiver 12 to display the frames of the game, where each frame comprises a depiction of graphical and/or textual data on a display device. The graphics associated with each game may be game-specific or may be applied to multiple games. The graphics may be used to represent one or more aspects of sensor data received from a sensor, such as sensor 10 of FIG. 1, and to represent game context information for the sensor data.

Figure 2:
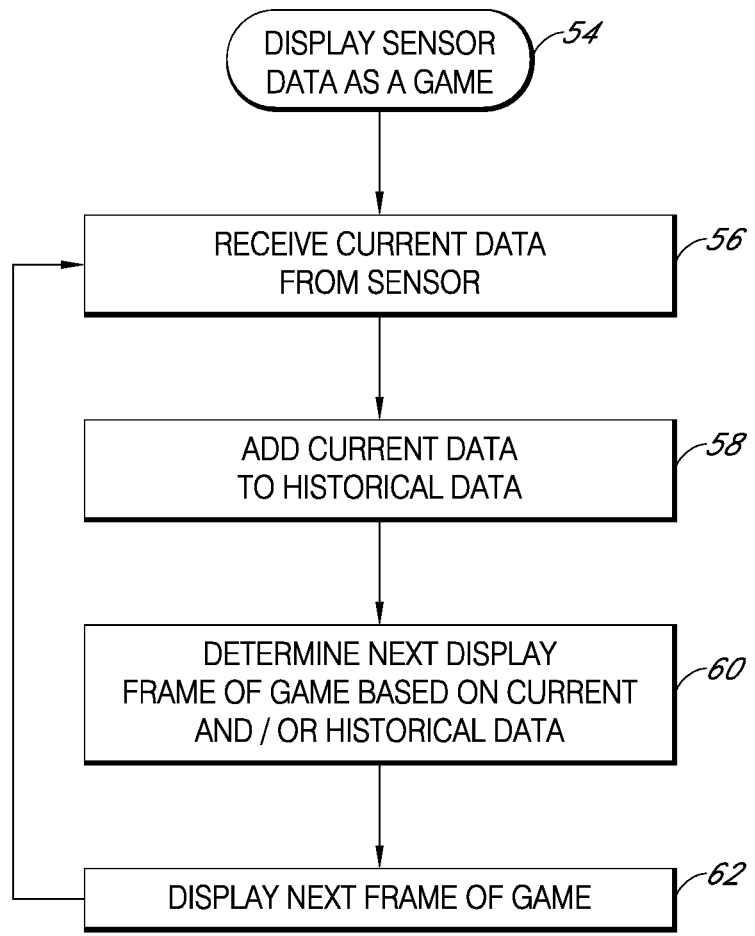
FIG. 2 is a flowchart that illustrates a process of displaying sensor data as a game.

FIG. 2 is a flowchart illustrating one embodiment of a method 54 of displaying sensor data as a game or a cartoon. The process is used by, for example, a receiver, such as receiver 12 of FIG. 1 to display a user interface that incorporates and/or is based on sensor data received. The process 54 includes receiving current sensor data from the sensor, which is the data point or data set most recently received, adding the received current sensor data to previously received data, determining a next frame to display based on the current sensor data and/or the previously received sensor data, and displaying the frame. In some embodiments, the receiver 12 generates graphical data indicative of a sequence of historical sensor data, as well as current sensor data, in a currently displayed frame. Depending on the embodiment, the method of FIG. 3 may include fewer or additional blocks and the blocks may be performed in a different order than is illustrated.

At block 56, current sensor data is received from the sensor 10. At block 58, the current sensor data is added to a memory containing sensor data received previously. The current sensor data and the previously received sensor data collectively form stored sensor data, which is used at block 60 to determine a next frame of the game. The sensor data may, for example, represent a glucose level, or a range of levels. In some embodiments, the sensor data is displayed with a resolution corresponding to the uncertainty of the measurement.

Each frame may be determined based on one or more selected sets of sensor data of the stored sensor data. The selection of a data set for determining a next frame may be based on a certain time frame. For example, the most recent sensor data may be selected. For example, the sensor data taken in the most recent 1 hour, 3 hours, 6 hours, day, week, month, or year may be selected. Sensor data in other most recent times may also be used. In some embodiments, sensor data received since a reference time may be selected. The reference time may include such times as when waking up, going to sleep, eating a meal, exercising, or taking insulin. Other reference times may be used. In some embodiments, sensor data received during specified time periods may be selected. For example, sensor data received between 1 pm and 5 pm on one or more days may be selected. Other time periods may be used.

In one embodiment, a host's glucose response associated with a consistent event, such as lunch, is analyzed such that a carbohydrate (referred to also as a "carb") estimate and insulin amount given, for example, are analyzed to determine a "typical" lunch size. For example, the insulin delivery information may be more accurate, with the time to action being the key variable such that reasonable estimates for that might estimate not only the typical, approximate meal size, but also the diversity of the meal (all carbs, high fat, etc.) based on the response, thereby allowing more customization for bolus calculation in the future based on "typical" meals. In one embodiment, hosts estimate a meal size (small, medium or large, for example) and/or meal makeup (high fat, high carb, low carb, balanced carb/fat/protein, etc.), and the sensor electronics may determine insulin delivery based on "learned" knowledge of the particular patients behavior and "typical" meal size and response.

In some embodiments, the selection of sensor data for a data set is based on the content of the sensor data, such as characteristics of transformed sensor data. For example, in some embodiments, sensor data taken over a specified time having glucose levels within a specified measurement range are selected and/or sensor data between upper and lower thresholds are selected. In some embodiments, sensor data greater than or less than a certain threshold are selected. The thresholds may, for example, correspond to blood glucose target range boundaries.

In some embodiments, the selected sensor data for a data set is selected based on processed data. For example, in some embodiments, raw sensor data is processed to determine rates of change in blood glucose levels for each time point for which sensor data is acquired, and data for the data set are selected for times when the rate of change in the sensor data meets certain criteria. For example, sensor data taken when the rate of change in the blood glucose levels is greater than a certain limit, less than a certain limit, or within a certain range may be selected. As another example, average glucose values for days of the past month during which the rate of change in data does not exceed a threshold may be selected for a data set. In some embodiments, the average values for days of the past month during which the rate of change in data does exceed a threshold may be also be selected as a second data set.

The selected one or more data sets are used in conjunction with graphics associated with the current game to determine the next frame of the game. For example, a selected data set may be represented with a series of frames, where each frame of the series depicts one or more data points, e.g. blood glucose levels, of the selected data set. In some embodiments, the most recent data point is represented with a first graphic and the historical data is represented as multiple second graphics. In addition, game context graphics may also be determined based on the current game and the previous frames of the game. In some embodiments, the game context graphics include graphics which represent target range boundaries. The range boundaries may be defined through an interface to a database storing the boundary data. The range boundaries may be defined by a caretaker of a child with diabetes via a computing device in communication with the child's receiver, for example. Thus, operation of the games may be customized according to the particular characteristics of the host.

In some embodiments, the game context graphics include graphics which represent a qualitative or quantitative assessment of performance. For example, a score can be shown, or an estimated HbA1c value. Other assessment graphics include a character having a smiling face or a frowning face, and/or a variation in a color of a graphic. In some embodiments, game context graphics include a target, which indicates a desired analyte level or analyte performance characteristic.

At block 62, graphics illustrative of at least portions of the selected one or more data sets are displayed in the next frame. In some embodiments, a sequence of frames is shown to generate an animation or a cartoon. For example, a series of frames, each depicting a subset of the selected data set may be shown sequentially, such that each successive frame shows more of the selected data. The series may be displayed in response to an input from the user.

Figure 3A:
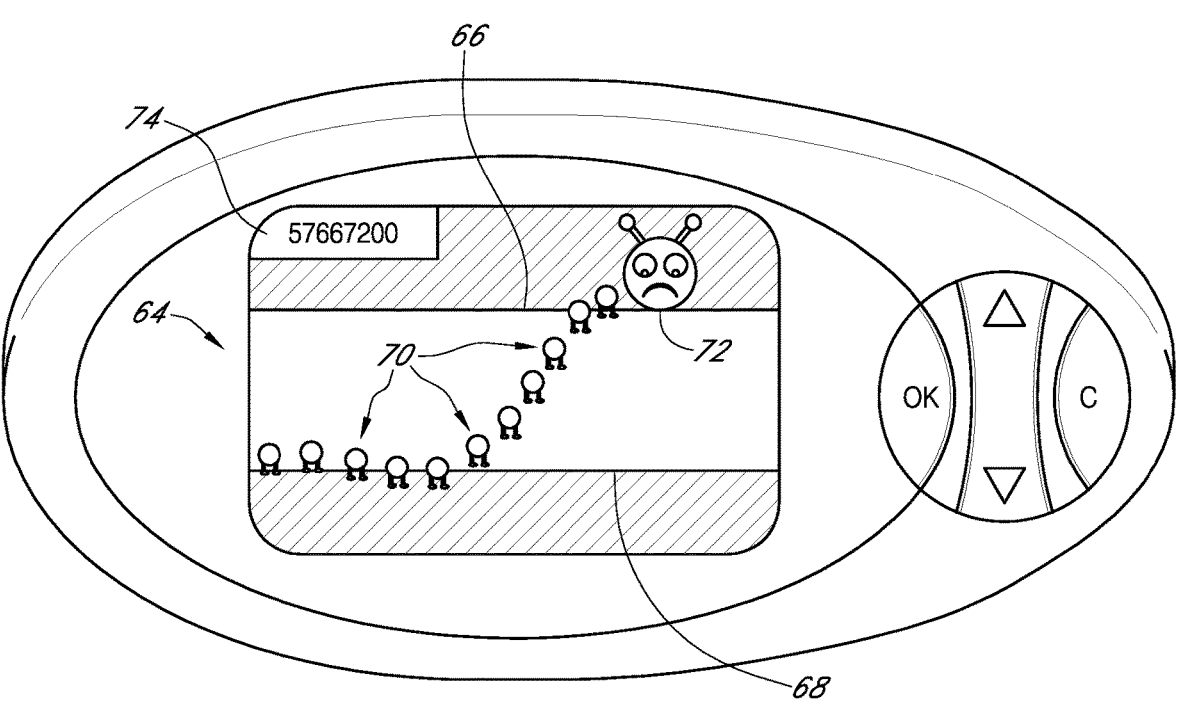
FIGS. 3A-3H are drawings illustrating various embodiments of displayed sensor data.

FIG. 3A is a drawing illustrating an embodiment of a frame 64 representing sensor data. The frame 64 includes a graphic 66 representing an upper limit of a target range for the host's glucose level, a graphic 68 representing a lower limit of the target range for the host's glucose level, a series 70 of graphics representing historical glucose level measurements, a graphic 72 representing the most recent measurement, and a graphic 74 representing an assessment of performance. In this embodiment, the graphics 70 and 72 cooperatively represent a centipede, where the centipede comprises body segment graphics 70 associated with historical sensor data, and a head graphic 72 associated with the latest sensor data. In this embodiment, the head graphic 72 has a face which is frowning because the latest glucose level is outside of a desired target range. In this embodiment, graphic 74 represents an assessment of performance as a numerical score.

Figure 3B:
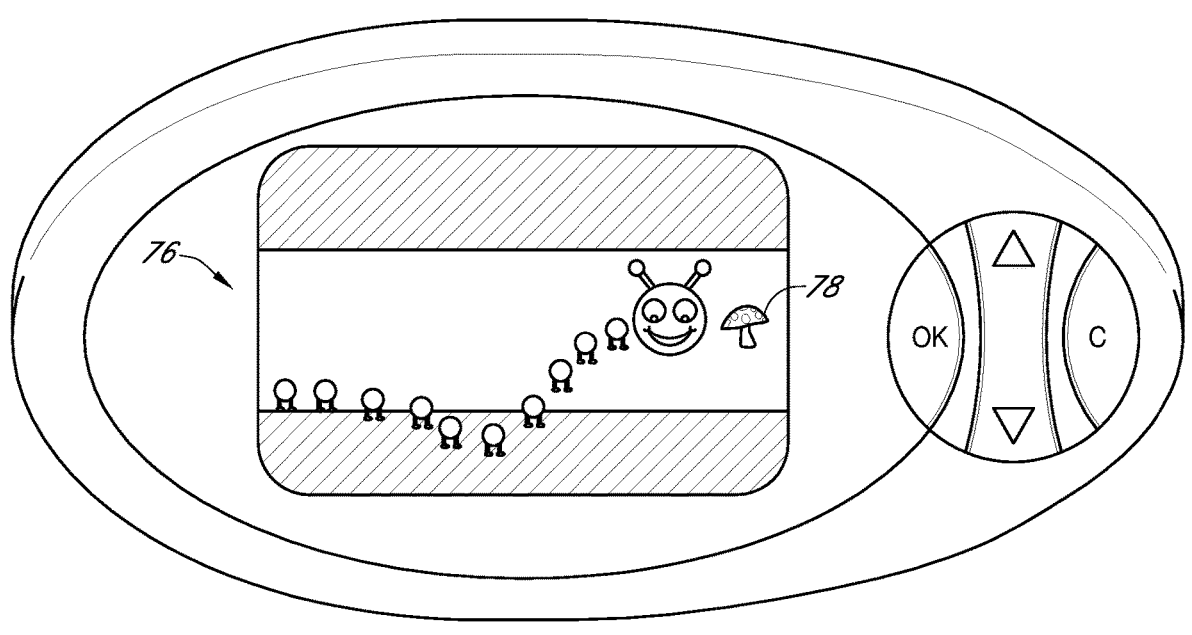

FIG. 3B is a drawing illustrating an embodiment of a frame 76 representing sensor data. Frame 76 includes a target graphic 78, which indicates a desired glucose level or range of glucose levels In some embodiments, the target graphic 78 can change positions from frame to frame in order to entice better analyte control from the user.

Figure 3C:
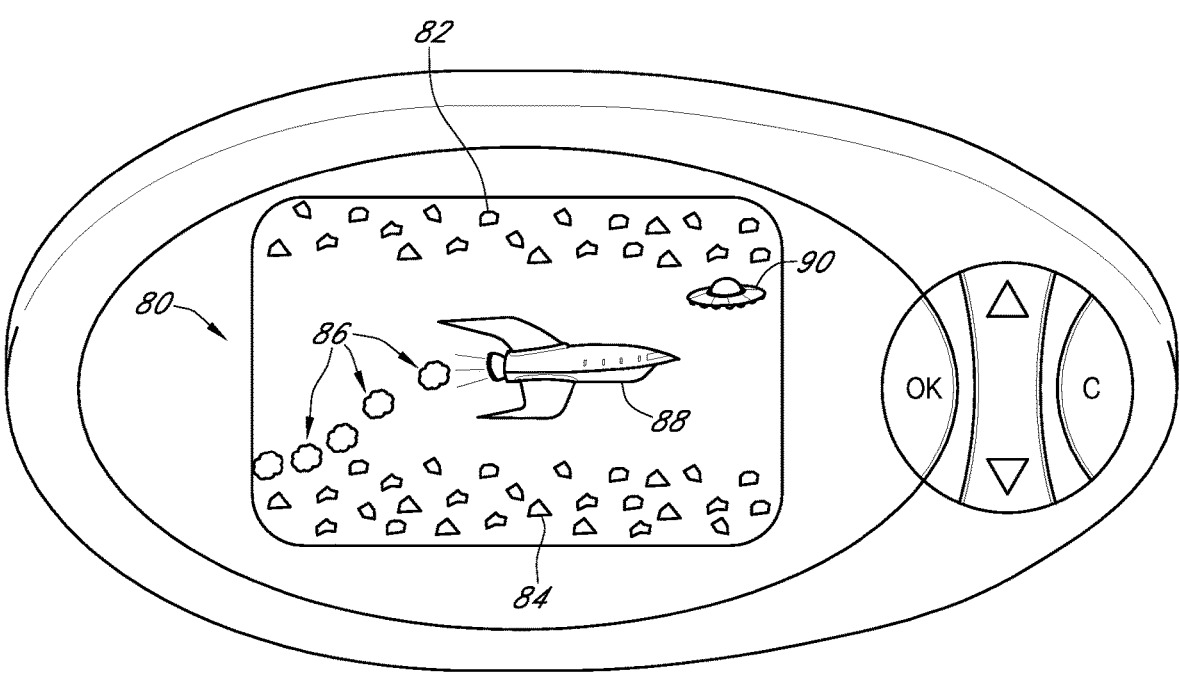

FIG. 3C is a drawing illustrating an embodiment of a frame 80 representing sensor data. The frame 80 includes a graphic 82 representing a higher than target range for the host's glucose level, a graphic 84 representing a lower than target range for the host's glucose level, a series 86 of graphics representing historical glucose levels, a graphic 88 representing the latest glucose level, and a graphic 90 representing a target glucose level. Depending on the embodiment, the frames of a game (e.g., FIGS. 2 and 3) may be updated in response to each newly received sensor data point or set, after a predetermined quantity of sensor data points or sets are received (e.g., a new frame is provided after five sensor data points or sets are received by the receiver), and/or in response to receiving sensor data matching a predefined criteria (e.g., a glucose level that is approaching a hypoglycemic level). In the embodiment of FIG. 3C, the graphic 90 is at the high end of the target range so as to entice the user to generate higher glucose levels.

Figure 3D:
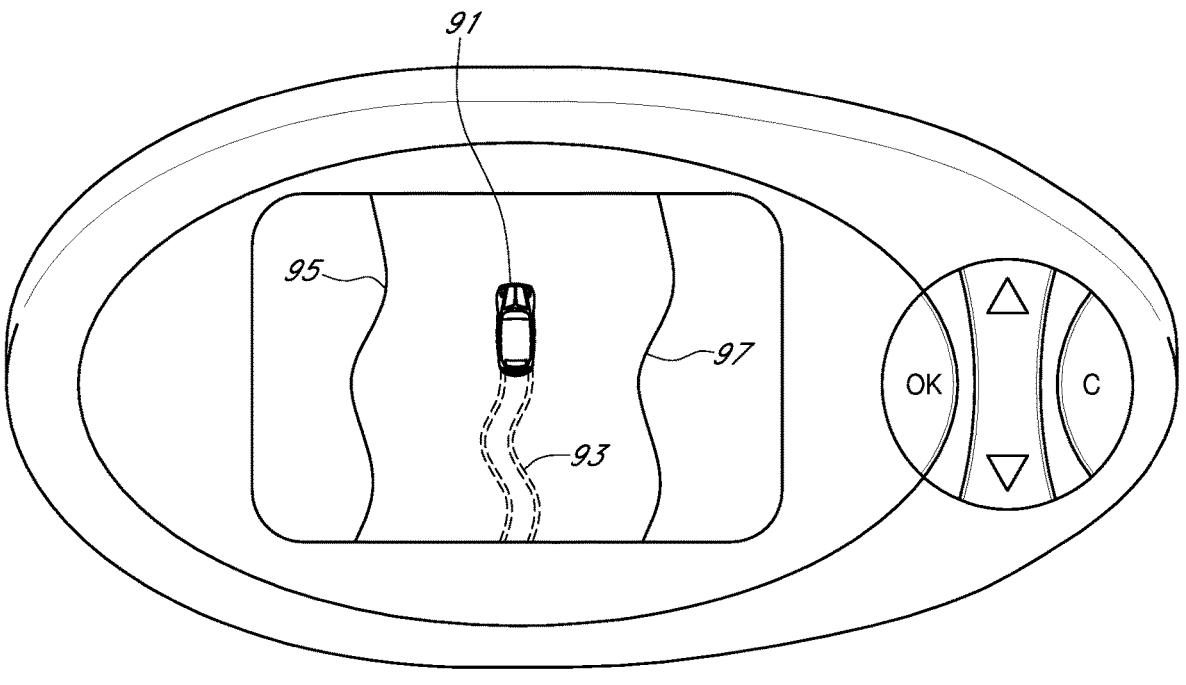
Figure 3E:
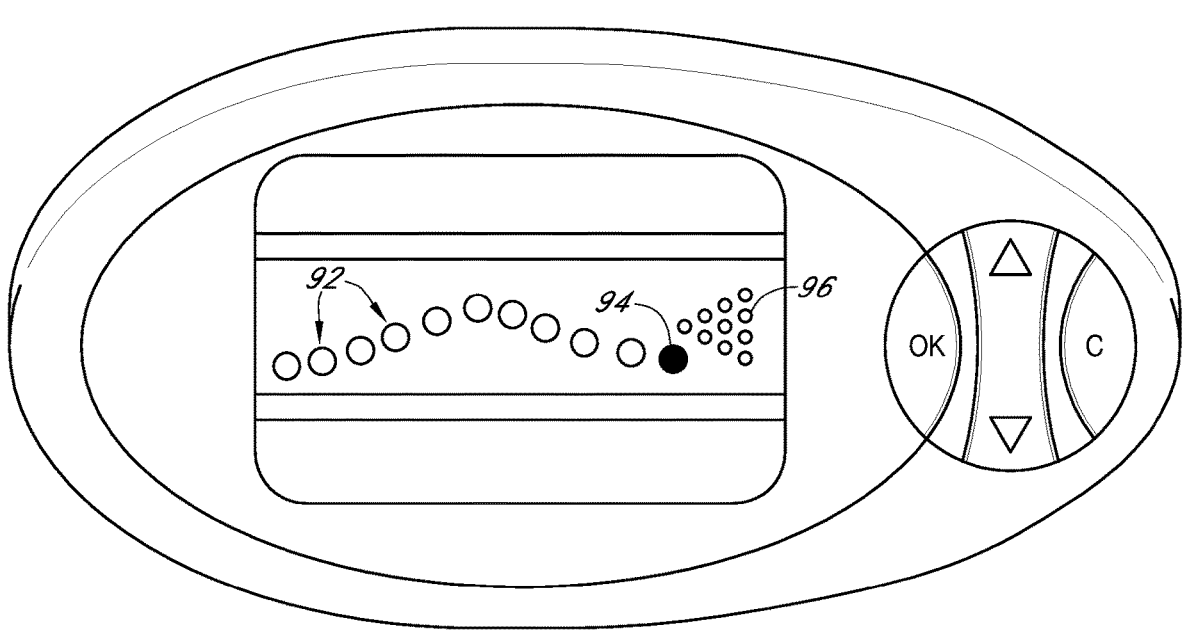

FIG. 3D is a drawing representing another exemplary frame illustrating graphics representative of historical and current sensor data. In this embodiment a vehicle graphic 91 represents the latest sensor data and a plurality of a track graphics 93 represent historical sensor data. The graphics 95 and 97 represent the boundaries of the desired target range, such as the sides of a road or racetrack, and may be generally vertical. In other embodiments, the boundaries, e.g., sides of the road, may be generally horizontal. In the illustrated embodiment, graphics 95 and 97 are non-linear. The non-linear boundaries can be used to further entice the user to achieve preferred glucose levels. In other embodiments, the boundaries (e.g., similar to graphics 95 and 97), which illustrates the sides of a road or racetrack, for example, may be non-linear, but parallel, or the boundaries may be linear. Depending of the embodiment, the boundaries may be user-settable and may be representative of a target glucose levels or ranges and/or may be representative of an alarm level (e.g. alert setting for hypo- or hyper-glycemia actual, predicted, or near).

Figure 3F:
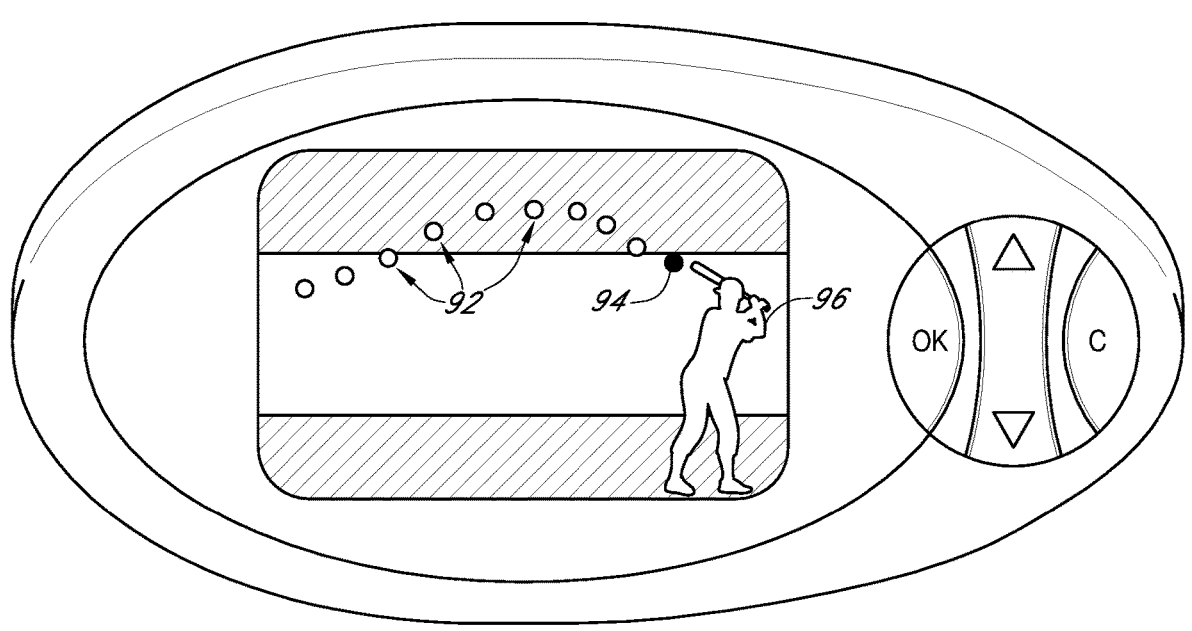
Figure 3G:
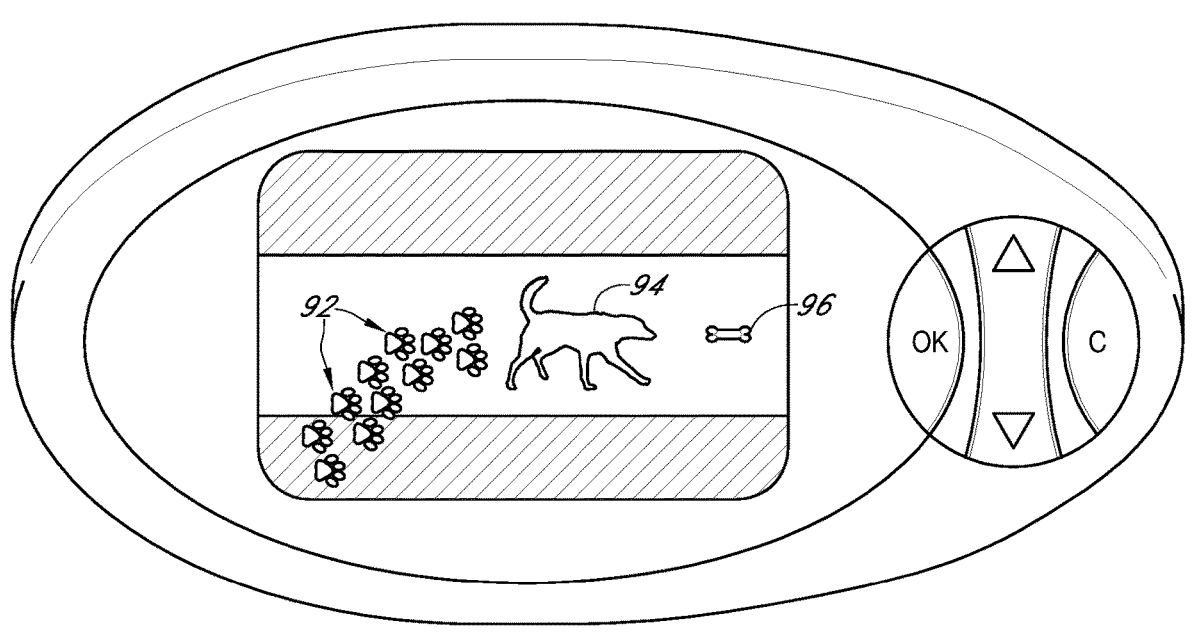
Figure 3H:
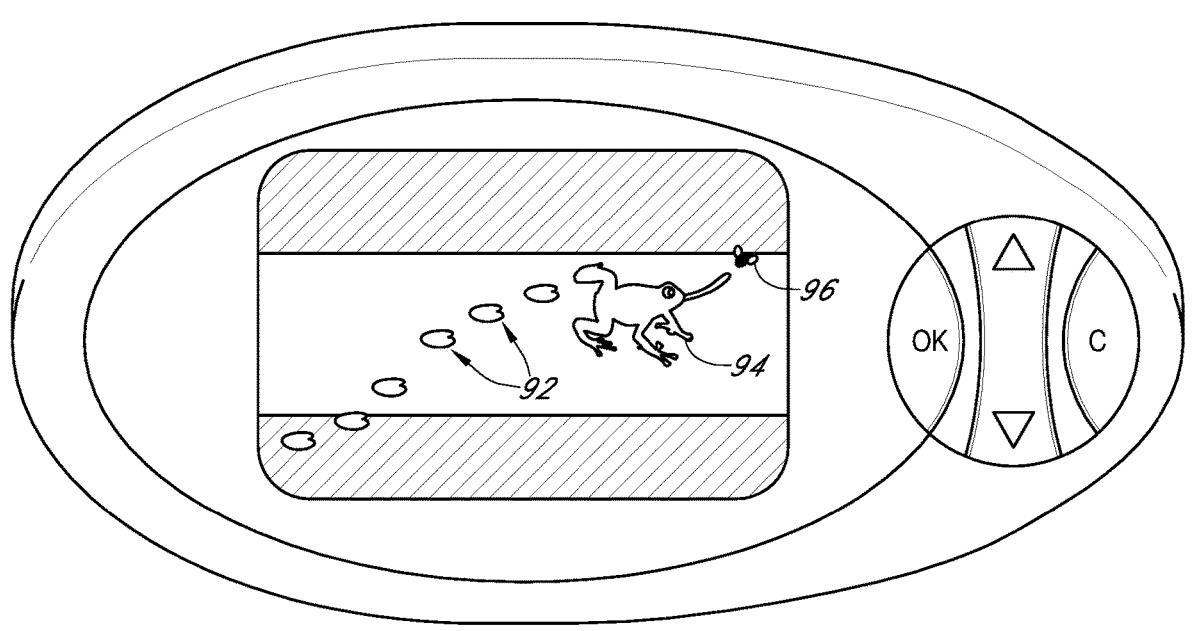
Figure 4A:
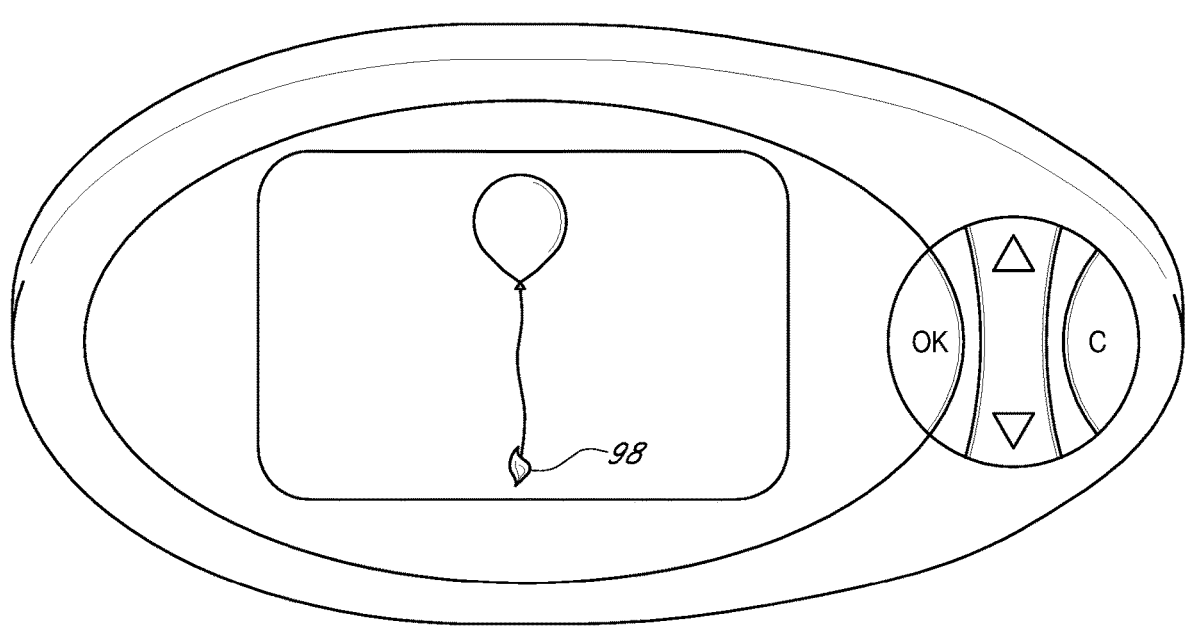
FIGS. 4A-4G are drawings illustrating an embodiment of displayed sensor data.
Figure 4B:
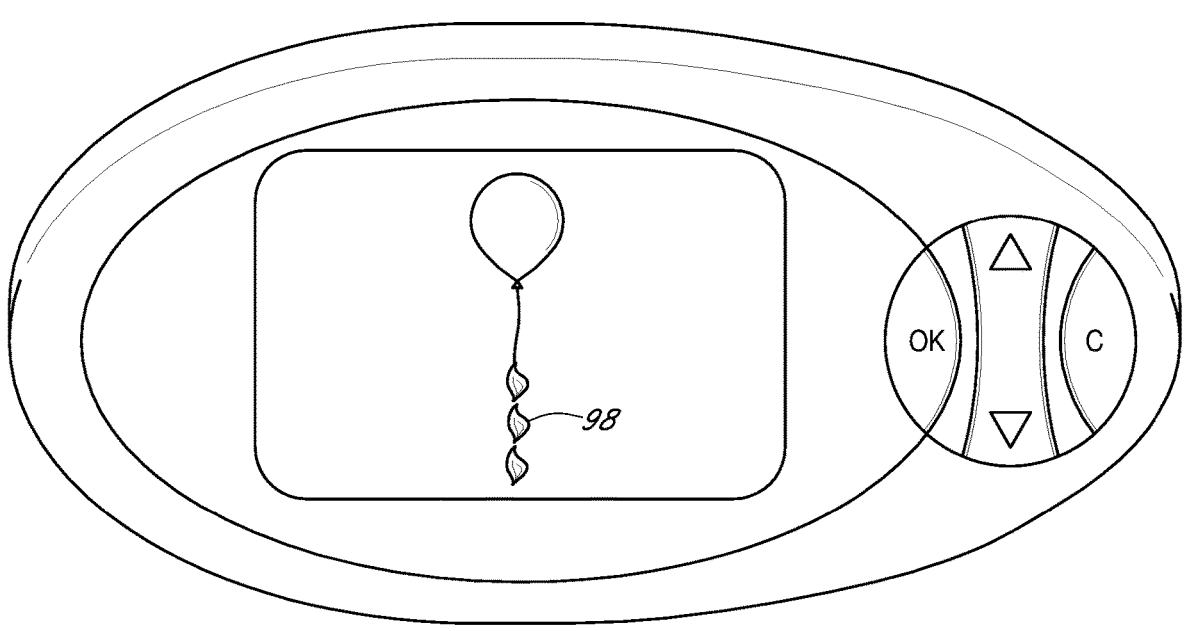
Figure 4C:
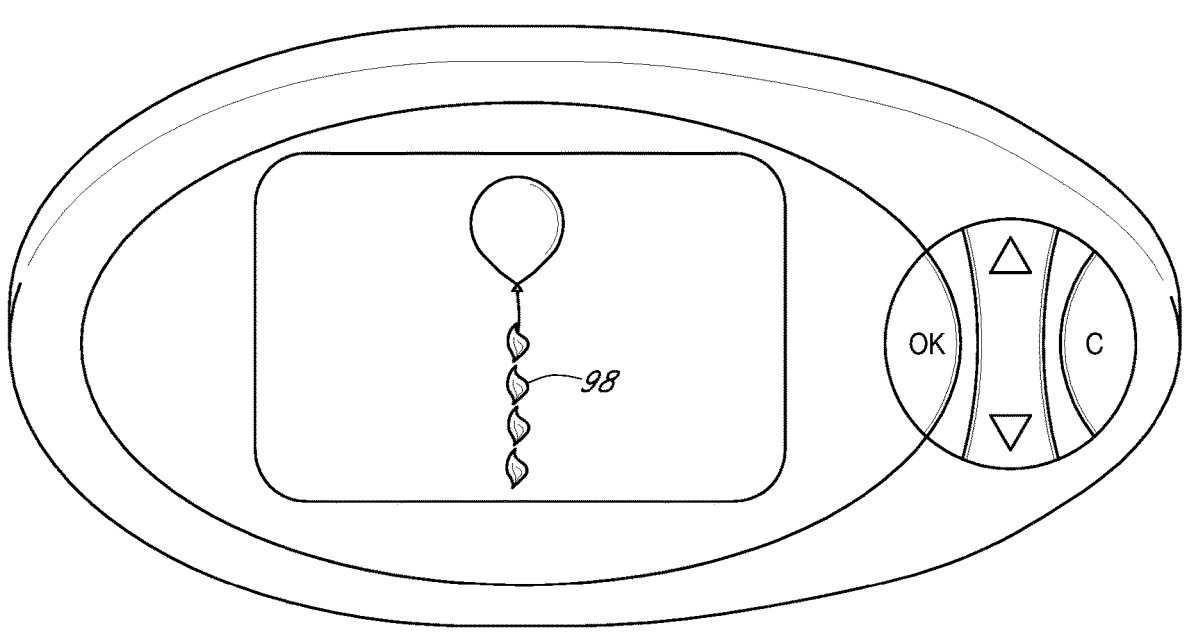
Figure 4D:
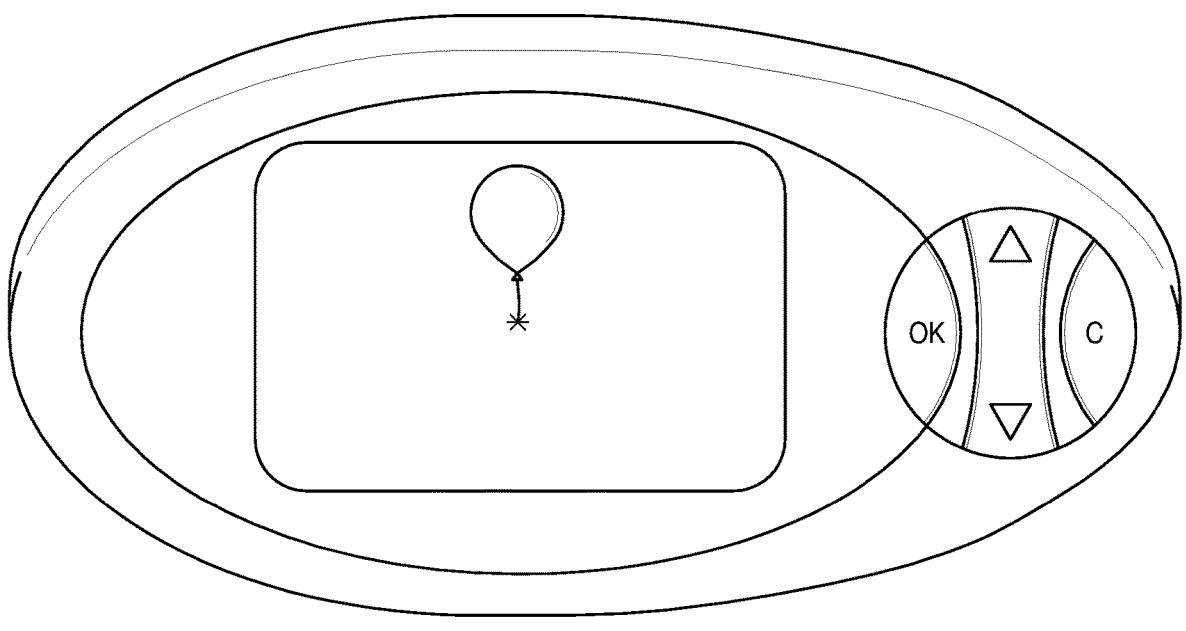
Figure 4E:
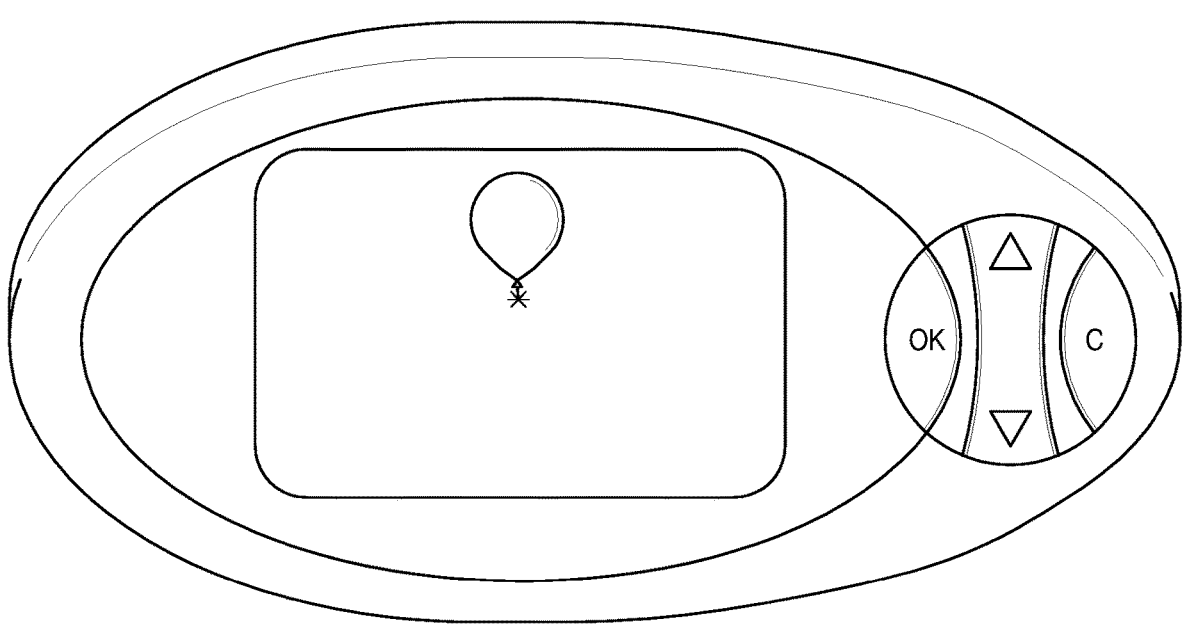
Figure 4F:
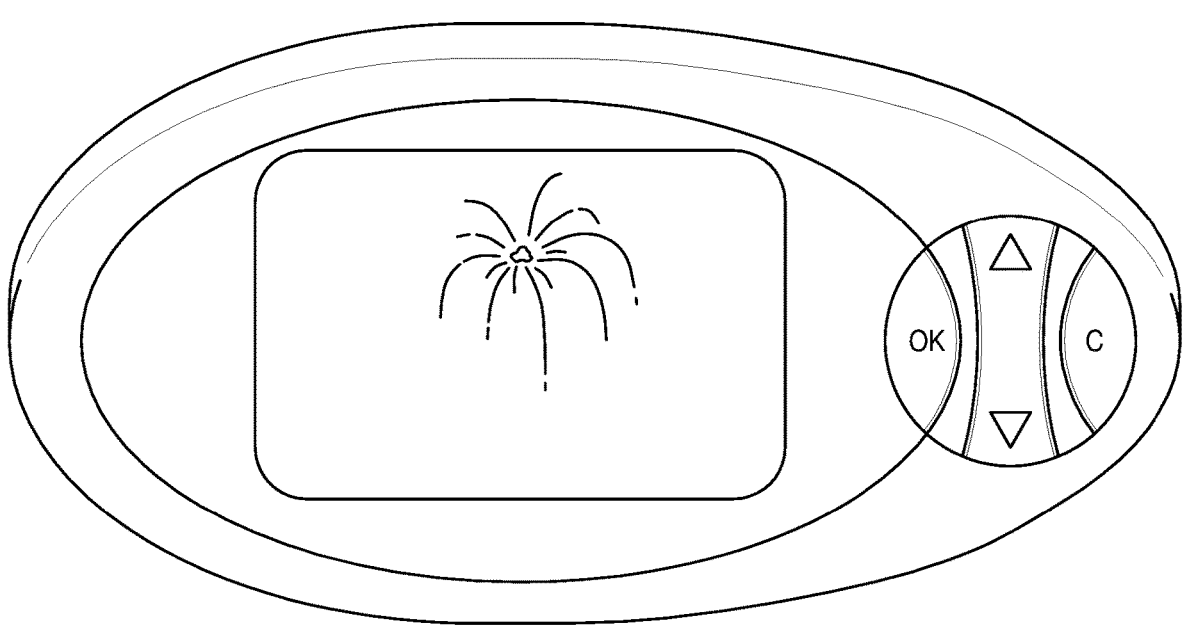
Figure 4G:
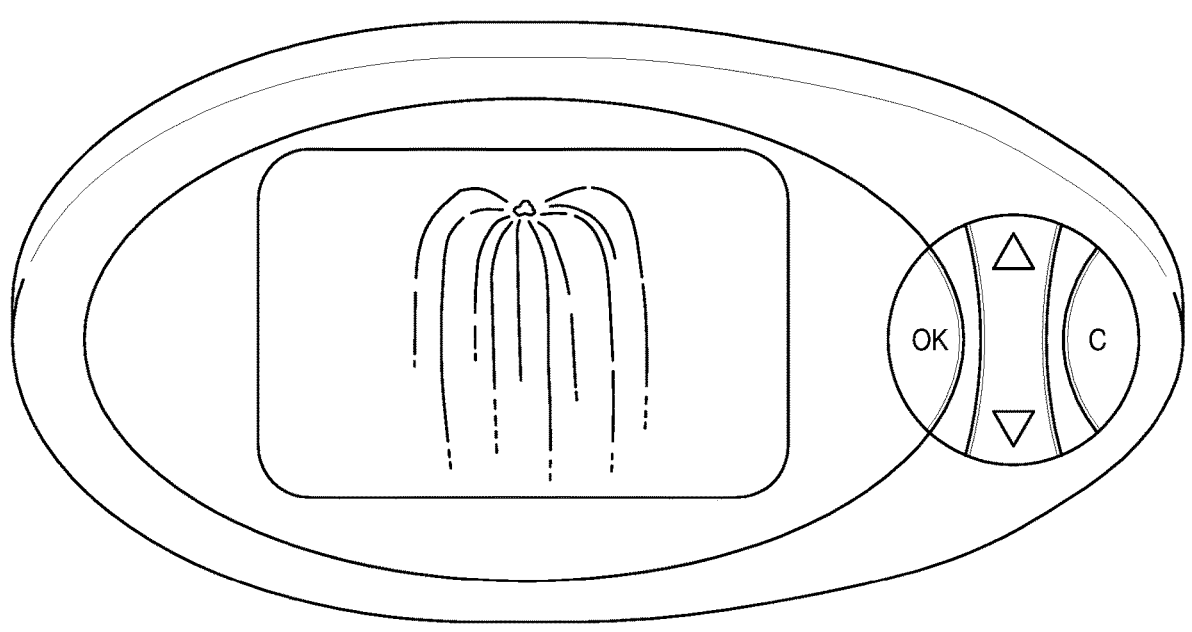

FIGS. 3E-3H are drawings representing other exemplary frames illustrating graphics representative of historical and current sensor data. In these embodiments the graphics 92 associated with historical sensor data trace paths of respective objects 94 moving toward respective targets 96. In some embodiments, once the object hits the target, such as by having the latest sensor data within a desired range, an animation is displayed. For example, in the embodiment of FIG. 3E, an animation showing a bowling ball knocking down the pins may be displayed. In the embodiment of FIG. 3F the hitter may be shown hitting a home run. In the embodiment of FIG. 3G, the dog may be shown eating the treat. In the embodiment of FIG. 3H, the frog may be shown eating the fly. Depending on the embodiment, the games may be configured so that the targets 96 are reached at predetermined times of the day, such as just before lunch, dinner, and/or bedtime.

In addition, various embodiments can be configured to give different types of awards depending upon whether the historical and current data stay within one or more predefined ranges (e.g., 1, 2, 3, 4 or more different ranges). Each award can correspond to a different award value or range of values, so that a higher award can be given if a host achieves a higher award value and a lower award can be given if the host achieves a lower award value. For example, if the historical and current data stay within a first, narrow range for a predetermined amount of time, then a higher award is given than if the historical and current data exceeds the first, narrow range during one or more time periods, but never exceeds a second, broader range during the predetermined amount of time. To illustrate, this process can be used in an environment of a virtual baseball game provided on receiver 12. In this regard, should the historical and current data stay within a first range for a predetermined amount of time, then the highest award, such as a home run, is awarded; if the historical and current data exceed the first range, but does not exceed a second range for the predetermined amount of time, then the second highest award, such as a triple base hit, is awarded; if the historical and current data exceed the first and second ranges, but does not exceed a third range for the predetermined amount of time, then the third highest award, such as a double base hit, is awarded; if the historical and current data exceed the first, second and third ranges, but does not exceed a fourth range for the predetermined amount of time, then a fourth highest reward, such as a single base hit, is awarded; and if the historical and current data exceed the first, second, third and fourth ranges at one or more points in time during the predetermined amount of time, then the lowest reward, such as a strike, out, end of game or the like, will be given. The process can then repeat with a new predetermined amount of time and a score of the baseball game can be tallied based on the results. In this manner, a virtual baseball game can be played based on a host's glucose sensor data.

Moreover, in place of or in addition to the various ranges discussed above, a type of reward given (e.g., homerun, base hit or out) can be based wholly or partly on other criteria. For example, the type of reward given can depend on a duration and/or amplitude of the historical and current data exceeding one or more ranges before the historical and current data fall back within the range during the predetermined amount of time. To illustrate, a homerun can be awarded if the historical and current data never fall outside of a range during the predetermined time period, and a triple base hit can be awarded if the historical and current data fall outside of the range for less than a threshold duration and/or the amplitude of the sensor data exceeds the range by less than a threshold amplitude. Second and single base hits can similarly be awarded based on other thresholds not being exceeded. An "out" or "end of game" can be given if one or more (including all) thresholds are exceeded. In the event both the amplitude and duration thresholds are taken into account for awarding a type of award, various weighting measures can be applied to the amplitude and duration threshold exceeded for determining the type of reward given.

FIGS. 4A-4G are a series of drawings representing other exemplary frames illustrating an animation representative of historical and current sensor data. In the series of Figures, a number of flames 98 are shown, where each of the first three frames (FIGS. 4A-4C) illustrate a successively greater number of flames 98. Each flame 98 represents a good glucose level, for example, a day in the past 30 days when the glucose level stayed within a target range, or an amount of time of the current day when the rate of change in the glucose level was less than a threshold. If a sufficient number of flames 98 are generated, an animation follows, which shows a fuse being lit, and fireworks exploding (e.g., FIGS. 4D-4G).

Figure 5:
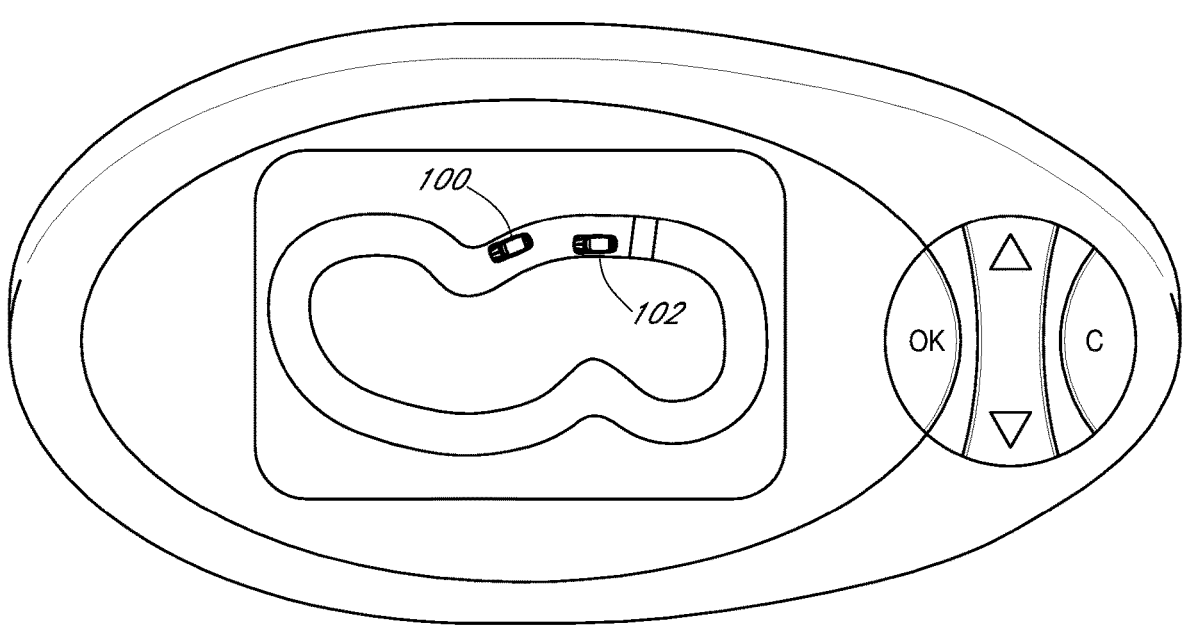
FIG. 5 is a drawing illustrating an animation graphically comparing two sets of sensor data.

FIG. 5 shows another exemplary frame illustrating graphics representative of historical and current sensor data. In this embodiment, the graphics are associated with at least two types of sensor data, such as data sets associated with a percentage of time within a target glucose range and percentage of time outside of the target glucose range. In this embodiment, two cars 100 and 102 are on a race track. Each car represents one of the data sets. Some aspect of each cars performance corresponds to the data of the associated data set. For example, the speed or the distance traveled for car 100 may represent a first data set—the percentage of time in target range, and the speed or distance traveled for car 102 may represent a second data set—percentage of time out of target range. Thus, the animation of FIG. 5 illustrates a graphical comparison of the two data sets. In some embodiments, the two data sets may be corresponding data (e.g., data from the same host) taken during two different time periods (e.g., the first data set may represent sensor data from a current week and the second data set may represent sensor data from a previous weeks). Accordingly, the animation may illustrate a graphical comparison of, for example, glucose control performance this week compared to last week.

Figure 6:
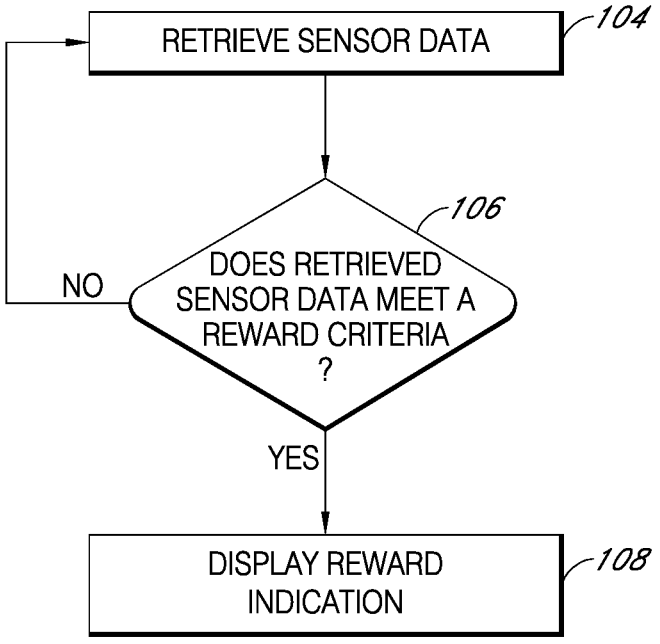
FIG. 6 is a flowchart that illustrates a process of displaying sensor data as a game where rewards are given.

FIG. 6 is a flowchart illustrating an embodiment of a method of displaying sensor data as a game where rewards are given. The process is used by, for example, a receiver, such as receiver 12 of FIG. 1. The process includes retrieving sensor data 104, determining whether the retrieved data meets a reward criteria 106, and displaying (or otherwise providing) a reward indication 108. In some embodiments, the process illustrated in FIG. 6 is initiated by a command generated in response to a request by a user. In some embodiments, the process is initiated by any interaction with the receiver which contributes toward meeting the reward criteria. In some embodiments, any interaction with the receiver contributes toward meeting the reward criteria.

The sensor data retrieved at block 104 includes at least one of current data and historical data. For example, the retrieved data may include the sensor data for the past 24 hours, or may include the sensor data for measurements taken between 12 pm and 6 pm. In some embodiments, the retrieved data may include transformed sensor data, such as calibrated and/or filtered blood glucose levels and/or one or more trend or rate of change indicators, for example.

The reward criteria to which the retrieved data is compared at block 106 may be dependent on the type of data retrieved. For example, if the retrieved data comprises sensor data for the past 24 hours, the reward criteria may be based on a minimum percentage of time for which the sensor data is within a target range. For example, the reward criteria may be set to 75%, and the retrieved data may indicate that the sensor data was within the target range 85% of the past 24 hours. In some embodiments, the reward criteria may be based on improvements in the sensor data. Accordingly, a comparison of the criteria with the retrieved data determines that the criteria for a reward has been met. If the reward criteria is not met, in some embodiments, the receiver displays an indication that the criteria is not met.

In one embodiment, points are awarded in response to certain actions by the host, such as receiving sensor data including a glucose level that is within an acceptable range. Thus, if sensor data is received every 5 minutes, for example, the host may receive more points every 5 minutes.

The points may be incremented until they reach a reward threshold and then the receiver may initiate communication of a reward to the host and/or caretaker, for example. The reward threshold may be an incremental point level, e.g., every 5,000 points, and/or may be associated with reaching a high score (e.g., higher than previously reached by the host, possibly within a certain time period).

If the reward criteria is met, at block 108 the receiver displays an indication of a reward. The indication may include a series of frames forming an animation. In some embodiments, the indication includes a single frame. In some embodiments, the display depicts the retrieved data, the criteria, and the reward indication simultaneously. Other rewards include having the opportunity to select a new "skin" for the receiver (e.g., colors, icon designs, etc.), unlocking levels of a game, unlocking an avatar, receiving credits towards purchase of a product. In some embodiments, the reward indicator is transmitted to a caretaker indicating that the user has met the reward criteria. The reward indication may be transmitted, for example, to a mobile device of the caretaker via email or sms. In some embodiments, the reward indication is randomly or pseudo-randomly selected from a plurality of stored reward indications.

In some embodiments, analysis information for the retrieved data, such as the target range, and the reward criteria, such as the 75% time within range, are entered by the user. In some embodiments, access to the entry of the analysis information and the reward criteria is limited by a security device, such as a password. For example, a parent may enter a password to gain access to a data entry mode by which the parent enters reward criteria, e.g., 75% within a target range over a 24 hour period.

Figure 7A:
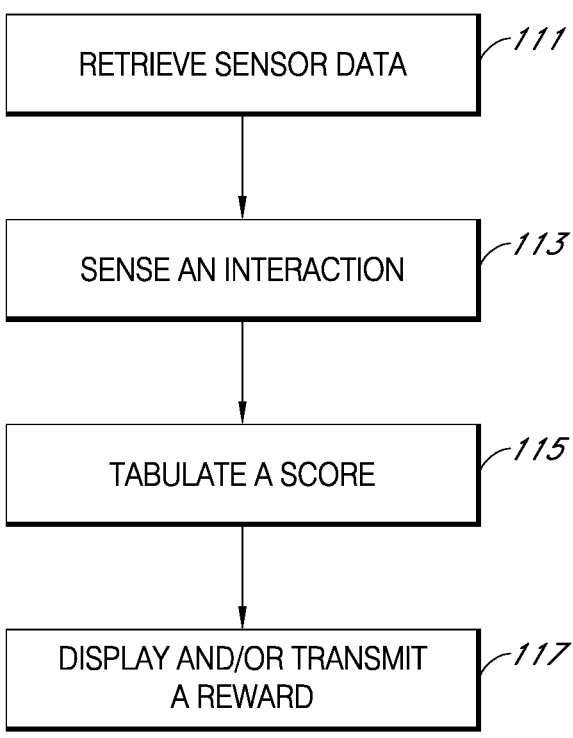
FIG. 7A is a flowchart that illustrates a process of generating rewards based on user interaction.
Figure 7B:
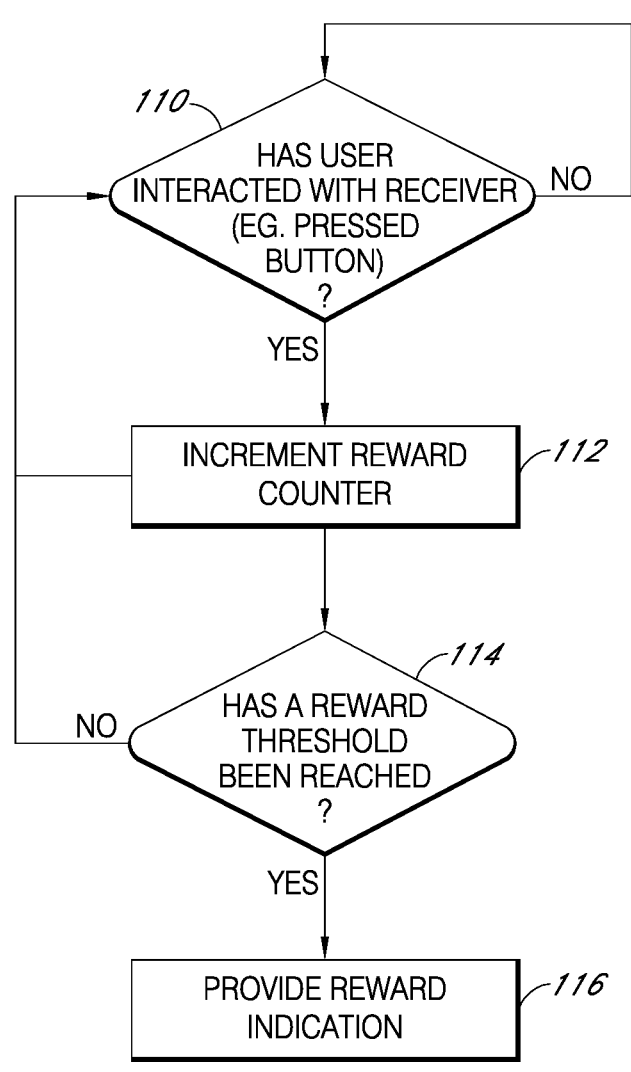
FIG. 7B is a flowchart that illustrates another process of generating rewards based on user interaction.

FIGS. 7A and 7B illustrate embodiments including systems and methods for providing rewards to a user to encourage interactions associated with a continuous glucose monitoring system. Some studies of pediatric diabetes have shown that as the child increases interactions with their receiver, hypoglycemic and hyperglycemic events are decreased. Much of this difference in glucose control may be due to the fact that users that are interested in being diligent in controlling glucose levels will interact with the receiver more according to this interest. However, this improvement in control can also be attained with less naturally diligent users by encouraging interactions of all kinds with the glucose monitoring system, even when those interactions are independent of the creation of or value of any sensor data. Encouraging a variety of different interactions with the system (in some embodiments all or substantially all interactions) will indirectly promote familiarity with the system operation, familiarity with typical user glucose levels, and familiarity with the effects user behavior has on their glucose levels. All these things will help the user control glucose levels better. Thus, by providing rewards to a child or other user with diabetes in response to many different types of interactions with their receiver or other portions of the monitoring system (e.g. pressing various buttons, changing display outputs, setting alarms, etc.), the frequency of hypoglycemic and/or hyperglycemic events may in turn be decreased.

In one such exemplary embodiment, the continuous glucose monitoring system includes a glucose sensor configured to provide real-time continuous glucose sensor data, a portable device comprising a user interface configured to receive user input and display the real time glucose sensor data responsive to user-interaction with the portable device and a processor module configured to tabulate a score based at least in part on user interactions with the user interface. While the exemplary embodiment may include a configuration wherein the processor module may be located within the portable display device, it should be understood that some or all of the processing and electronic circuitry associated therewith can be located local to the sensor, for example, within a transmitter body wired to the sensor. Additionally, some or all of the processing and electronic circuitry associated therewith can be located within hardware or software operably connected with the monitoring system, for example, through a download cable or through a wireless connection to a personal computer, mainframe computer, server, or the like.

Referring now to FIG. 7A, at block 111, the processor module is configured to retrieve the sensor data, either directly or indirectly through a wired or wireless connection with the sensor. As described in more detail elsewhere herein, the data can be transformed using a variety of algorithms to provide useful data to a user. Examples of useful data include not only real-time analyte values, but can also include trend information in the form of graphs or directional indicators, statistical data associated with a period of time, improvement in diabetes management or other metabolic control associated with an improvement with analyzed data from one time period to another time period, amount of time within a target range, and/or the like.

At block 113, a user interaction with the continuous glucose monitoring system is sensed or detected. In the exemplary embodiment of a portable display device, wherein the device is configured to receive sensor data from the glucose sensor, the device is configured to selectively display information associated with the sensor data and/or the sensor data in response to interactions from the user, which can be sensed by the device. However, other user interactions with the continuous glucose monitoring system can be sensed; for example, interactions associated with a remotely located device, such as a software program or internet site running on a computer system associated with the continuous glucose monitoring system, and these interactions can be provided to the portable display device, or any processing circuitry associated with the continuous glucose monitoring system that tabulates a score or increments a reward, as described in more detail elsewhere herein.

In some embodiments, the sensed interaction includes at least one of pressing a button, touching a screen of the receiver, activating another input device, selecting sensor data for viewing on the receiver, downloading data, inputting events, setting parameters, confirming sensor data, and the like. In some embodiments, the score may be based at least in part on receiving sensor data during a predetermined time period. In some of these embodiments, the system may sense an interaction with the system that comprises the attachment or continuous wearing of at least a portion of the glucose monitoring system for a predetermined amount of time. The attachment or placement of the receiver on the user may, for example, be detected by continuous or periodic reception of sensor data from an implanted sensor without significant interruption or periods of failed data reception. For example, wherein the monitoring system is configured for a particular sensor session time period (e.g., 3, 5, 7, 10 days, or the like), score or reward counters may be incremented based at least in part on a completion of a sensor session (e.g., 3-, 5-, 7- or 10-day sensor session), a plurality of sensor sessions (e.g., 1, 2, 3, 4, 5, 6, 7, or more sensor sessions), predetermined number of substantially consecutive sensor sessions, a predetermined time period (e.g., 1-, 3-, 5-, 7-, 10, 14-, 21-, 30-day, or more), or the like.

In some embodiments, the sensed interaction is any action that causes current sensor data to be displayed. For example, pressing a button, touching a screen, adjusting an alarm for increased sensitivity (e.g., more sensitive alarm thresholds). In some embodiments, the sensed interaction causes historical sensor data to be displayed, for example display of the 1, 3,6, 9, 12, 24 hour trend screen(s) or the like. In some embodiments, the sensed interaction initiates or changes a display on the receiver. For example, pressing a button or touchscreen may awaken the device from a sleep mode and cause the device to display current sensor data. A button push may change the display from current data to historical data, or may change the display to one that contains a projected future glucose concentration. It may be noted here that the score increase or reward may be given in response to many different interactions regardless of the user's diligence in measuring glucose levels or success at maintaining them. Providing rewards based at least in part on such interactions, however, may lead to better success at glucose control in the future.

At block 115, the processor module is configured to tabulate a score, also referred to as incrementing a reward counter, associated with one or more user interactions, such as the user interactions described herein. In some embodiments, the processor module is configured to detect substantially all sensed interactions, where substantially all sensed interactions are input into the score tabulation or reward counter. In some embodiments, the processor module is configured to detect one or a plurality of predefined interactions, whereby the score or reward counter can be incremented. In some embodiments, the sensed interactions used to increment the score or reward counter are independent of the creation or value of any sensor data; for example, a user can be simply rewarded for interacting with the device regardless of any performance associated with their disease management.

In some cases, it is advantageous to include time based limitations on which interactions can cause the score or reward counter to be incremented. Thus, in some embodiments, the processor module is configured for sensing time periods between interactions, and incrementing the reward counter in response to a second interaction when the second interaction is sensed within a predetermined time period from a first interaction. For example, the score may be incremented only if interactions with the device are performed with a certain pre-defined frequency or frequency range. Excessive delay between interactions may result in reduced or no score increment. At the other end of the spectrum, to avoid having a user just mindlessly press buttons to achieve high scores, a limit on the amount of reward or score may be set for a given time period, for example, a user may achieve up to a predetermined number of points for up to a predetermined number of interactions in a predetermined time period. One of ordinary skill in the art can appreciate a variety of numerical and time-based limits that may be applied to encourage a reasonable or optimal interaction frequency.

As noted above, it is believed to be advantageous to increment scores/reward counters based on interactions that are not dependent on glucose measurements themselves. However, this does not mean that providing rewards for direct success in glucose management is not also worthwhile as part of a reward system. Thus, in some embodiments, the score may also be based at least in part on one or more sensor data values falling within a predetermined range. For example, when a predetermined number or average of a predetermined number of glucose values are within a target glycemic range over a period of time.

In some embodiments, the score is based at least in part on sensor data associated with a predetermined time period meeting one or more criteria. For example, criteria can include target range of analyte values, average and/or statistical measures of analyte information over a time period. Average and/or statistical measures can include area under the curve, MARD, ARD, A1c, and the like. Some additional examples include measures of, sustained outcomes of increased normoglycemia, decreased area under curve, decreased hypoglycemic episodes, decreased variability, and the like.

In some embodiments, the score is based at least in part on a change in one or more sensor data values within a predetermined time period immediately after an alarm is triggered. For example, when a hypoglycemic alarm is triggered, a score can be tabulated based on the amount of time before the user achieves normoglycemia (e.g., glucose within a predefined target range). For example, the increment or value of the score can be based on whether the user achieves normoglycemia within 10, 20, 30, 40, 50, 60, 90, 120 or more minutes.

In some embodiments, the score is based at least in part on sensor data associated with a first time period indicative of an improvement in glycemic control or diabetes management as compared to sensor data associated with a historical time period, including averages or statistical measures evaluated over a predetermined time period. For example, if a user decreases the amount of time spent in a hyperglycemic range during a week time period as compare to a previous week time period, a particular score or reward amount can be calculated or tabulated. It should be appreciated that numerous other statistical and/or analytical measures of analyte data can be used to compare between any definable time periods and provided with any number or scoring options associated therewith, as can be understood by one of ordinary skill in the art.

In some embodiments, the score is based at least in part on user interactions involving setting of or changing of receiver operation parameters. Some receiver operation parameters include alarm settings (e.g., analyte thresholds, rate of change thresholds, predictive alarm settings, type of output, display features, and the like). It should be noted that operational parameters can be also be set, displayed and/or applied in a portable device type receiver and/or any other device that receives and/or displays the sensor data, including, downloadable software, web-hosted databases, servers, and the like.

In some embodiments, the score is based at least in part on user interactions that cause downloading of data by a user from the receiver to another processing system, for example downloadable software, web-hosted databases, servers, and the like. In some embodiments, the score is based at least in part on whether or how the user sets or confirms alarm settings on the receiver; for example, when an alarm criteria is met, the receiver triggers an alarm, and the user acknowledges the alarm by pressing a button, touching the screen, or the like.

In some embodiments, the score is based at least in part on an evaluation of the sensor data to determine whether the user is maintaining good control, for example by tracking a running average of average glucose over time. Maintaining good control can include a variety of statistical and clinical evaluations of the data, wherein the determination of good control or improvement in a particular patient's diabetes can be user settable, physician settable, adaptable by an algorithm on the system, relative to a previous sensor session or time period, or the like.

In some embodiments, the score is based at least in part on user events, for example, when a user enters an event into the receiver and/or other systems associated with the system. Some examples of events include caloric intake, level of activity, health, and the like.

Whether tabulating a score, incrementing a reward counter, or the like, it should be appreciated by one of ordinary skill in the art that different criteria can be given different weighting and/or points. For example, wherein the goal of a physician is to simply encourage regular wear of the continuous glucose monitoring system, the system can be set with a heavy weight (e.g., highest scoring) for continuous sensor wear and/or user interaction as compared to achieving targets with regard to sensor data. Numerous scoring or incrementing methods can be implemented by the manufacturer, user settable (e.g., by a user or care giver), via downloadable software, via communication with an internet site and/or the like.

At block 117, the processor module is configured to display a reward indication (or score) on the receiver and/or transmit a reward indication (or score). A score can be a numerical value associated with a calculation with a variety of user interactions, however, other methods of scoring are possible. A reward indication, which can include a score and/or be based at least in part on a score, can provide a physical and/or conceptual reward, including but not limited to a numerical value, credit from the manufacturer, an "opt-in" to a social networking group or site, changing of a display on the receiver when the score reaches a predetermined reward threshold (e.g., transformation of character or display animation as a reward such as described above with reference to FIGS. 3-5), achieving new sounds (e.g., tones, downloading of tones, animation, etc), and the like.

The reward indication can be displayed on and/or transmitted to any component associated with the continuous glucose monitoring system, including, a user interface of a portable receiver, a text or email to a care giver's device linked to the user's system, downloadable software, internet site, and the like). Additionally, the score or reward indication can be configured to be displayed or transmitted continuously, at predetermined levels of achievement, at a predetermined reward threshold or value, at predetermined time periods or events, and the like.

In some embodiments, displaying and/or transmitting the reward includes transmitting a score and/or reward to an internet site, whereby users can connect with other users and/or their physician to share or compete. It is believed that by interacting through social networking or data sharing, additional motivation can be achieved. Additionally, rewards can be used by a manufacturer to provide credits, new features, upgrades, accessories, and the like.

FIG. 7B is a flowchart that illustrates another exemplary process of generating rewards based on interactions of the host with the receiver. The method of FIG. 7B may be performed by a receiver, such as receiver 12 of FIG. 1. Depending on the embodiment, the method of FIG. 7B may include fewer or additional blocks and/or the blocks may be performed in an order than is different than illustrated.

In the embodiment of FIG. 7B, interactions with the receiver contribute towards meeting one or more reward criteria. The method of FIG. 7B includes determining that an interaction with the receiver has occurred 110, incrementing a reward counter 112, determining whether a reward threshold has been reached 114, and providing a reward indication 116.

At block 110 an interaction with the receiver is sensed. Depending on the embodiment, and as described above as well, the interaction may include pressing a button, touching the screen, or activating another input device on the receiver. Interactions may also include other actions taken by the user, such as viewing sensor data on an external device. In some embodiments, interaction includes downloading data, inputting events, setting parameters, confirming sensor data, and the like, as described in more detail elsewhere herein. In some embodiments, interaction is based on an amount of time the sensor is used, for example, over a predetermined time period.

At block 112 a reward counter is incremented in response to sensing of an interaction at block 110. In some embodiments, all interactions generate a same increment value. In some embodiments, some interactions have higher increment values than other interactions. For example, interacting with the receiver in order to view glucose level trend information may be associated with a higher increment value than interacting with the receiver in order to view a current glucose level. In one embodiment, increment values for the same or similar interaction may be limited during a predetermined time period. For example, a child may be limited to receiving reward points only for a first 5 times that a particular button on the receiver is pressed within any 5 minute period. In some embodiments, increment values for various interactions are programmable.

In addition, a higher increment value award can be given if a first interaction is followed by a particular second interaction. The first interaction can be different from or the same as the second interaction. As an example, a higher increment value can be given if a user follows interacting with the receiver 12 in order to view glucose level trend (a first interaction) with exercise (a second interaction). In various embodiments, the receiver 12 receives or generates exercise data for determining whether the host has exercised from one or more external or internal devices, such as a GPS device, accelerometer and a heart rate sensor. Furthermore, a higher increment value can be awarded based on the level of exercise performed as determined from the exercise data.

At block 114 the value of the reward counter is compared to a reward threshold. If the comparison indicates that a reward has not been achieved, the method returns to block 110. However, if the comparison indicates that a reward has been achieved, the method moves to block 116, where a reward indication is provided to the host, a caretaker, a doctor, and/or other interested party. The reward indication may be similar to the reward indication of block 108 of FIG. 6.

FIG. 8A is a flowchart illustrating one embodiment of a method of interacting with a host via a tutorial. The method of FIG. 8A displaying tutorial data to the host, such as a series of glucose levels of an exemplary host, receiving input from the host of an action that should be taken in response to the provided exemplary glucose levels, and generating next glucose levels in response to the received input from the host. In this way, the tutorial may be used to educate the host as to how certain actions affect (or don't affect) the blood glucose levels. The tutorial data may be used to educate the user about expected consequences to various actions in various circumstances. The method may be performed by, for example, a receiver, such as receiver 12 of FIG. 1. Depending on the embodiment, the method of FIG. 8 may include fewer or additional blocks and/or the blocks may be performed in an order than is different than illustrated.

For example, a tutorial may display graphics representing glucose measurements that are increasing. The user may select exercise as a response. The tutorial then calculates simulated glucose values based at least in part on the response. In this example, the tutorial helps the user become more familiar with expected results of performing the various actions.

FIG. 8B illustrates three series 810A, 810B, 810C, of frames that may be displayed on a receiver as part of an interactive tutorial. Each of the frame series 810 has three frames, including a first frame 121 that corresponds with block 120 of FIG. 8A wherein tutorial data is displayed to the host, a second frame 123 that correspond with block 122 of FIG. 8A wherein input of a simulated action is received from the host, and a third frame 127 that correspond with block 126 of FIG. 8A including graphics indicating simulated glucose measurements that are responsive to the simulated action received from the host.

Beginning in block 118, the receiver determines tutorial data. The tutorial data may be based at least in part on actual measurements from a glucose monitor and/or other sensor, such as episodic SMBG. In some embodiments, the measurements were taken while monitoring the current host and stored in a memory. In some embodiments, the memory has data from one or more other users. The memory data may additionally contain synthesized data, which is not the result of measurements, but is generated by a method or using a synthesis algorithm. The memory may contain data representing various glucose excursion scenarios, such as blood glucose levels increasing towards hyperglycemia and decreasing towards hypoglycemia.

In one embodiment, patterns in the tutorial data are identified and a list of potential causes, allowing user, doctor/HCP, algorithm or remote analysis to determine most likely causes, are generated and displayed as a list of potential solutions or responses. With the potential solutions/responses, the user, doctor/HCP, algorithm or remote analysis can then determine the most likely actions or responses to recommend. In one embodiment, the response impact may be estimated by the sensor electronics and/or documented, e.g. whether the user/caretaker followed the advice, and if not what actions were taken. In one embodiment, similar methods may be used in data management software or any remote analysis done whether by algorithm or remote HCP or clinical personnel or other trained to interpret data.

At block 120, the tutorial data is displayed. The tutorial data may be displayed as a series of frames displaying a game, an animation, or a cartoon. For example, a series of blood glucose levels may be displayed as graphics similar to those of any of FIGS. 3A-3H. In other embodiments, the tutorial data may be displayed in the form of textual data or as one or more graphs. As noted above, frames 121 of FIG. 8B illustrates exemplary displayed tutorial data.

Next, in block 122, the receiver receives an indication of an input from the host. The input indicates an action to be taken in response to the currently displayed tutorial data. For example, the action can be any of eating food, eating a glucose tablet, exercising, injecting insulin, responding to stress or injury, contacting someone for help, such as a teacher, a parent, or a medical professional, and/or taking no action. As noted above, frames 123 of FIG. 8B illustrate selected actions 125 displayed alongside the glucose data so as to indicate the relative timing of the actions 125 and the glucose data.

At block 124, the receiver simulates a response to the action indicated by the user. For example, based on the glucose levels, trends in the glucose levels, and/or the action indicated by the user, a processor in the receiver may generate a simulated response to the action based on a simulation algorithm. In one embodiment, a trend in the tutorial data may not change immediately after the host indicates that an action should be taken. For example, if the host indicates an action of eating food, the tutorial data may not indicate any changes in the current trend of the blood glucose levels for 30 minutes (or some other time period) representative of a time period that is required to digest the food and increase the blood sugar levels of the exemplary host. In one embodiment, the simulated responses may be compared to sensor data that was actually measured/seen, and the different in the simulated responses and the actual responses may be utilized in by the algorithm for additional user customization and response knowledge.

At block 126, the simulated response to the action is displayed. As noted above, frames 127 of FIG. 8B illustrate simulated responses displayed along with the tutorial data and the actions 125. In some embodiments, the simulated response is displayed along with the data representing measurements prior to the action. In some embodiments, the action take is represented with an icon in the display. In some embodiments, an animation is generated indicating the simulated response. In some embodiments, a reward indication is displayed if reward criteria are met. In some embodiments, simulated responses for one or more alternate actions may be generated and displayed, for example, in response to an input indicating a request for such a display. In some embodiments, a simulated response of an alternate action is generated and displayed if the action indicated by the user is not optimal.

In one embodiment, the method repeats blocks 120-126 as more simulated actions are received from the host and more simulated blood glucose levels responsive to the actions are generated by the receiver. In this way, the host is able to simulate an extended time period of activities (e.g., from morning until night) in a very short time frame (e.g., in 1-15 minutes, for example) while learning how certain actions affect blood glucose levels. In one embodiment, the graphics used for the tutorial are similar/same as used for the actual sensor data of the host, e.g., one or more of the games illustrated in FIGS. 3A-3H or the like.

Figure 9A:
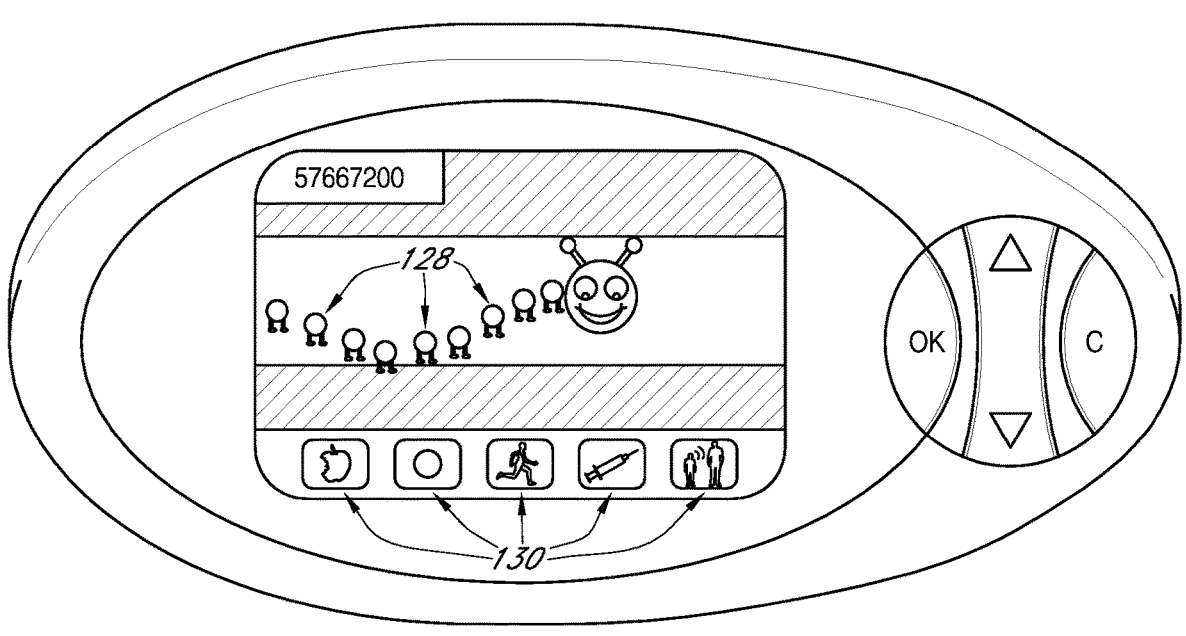
FIGS. 9A and 9B are drawings illustrating embodiments of displayed tutorial data.
Figure 9B:
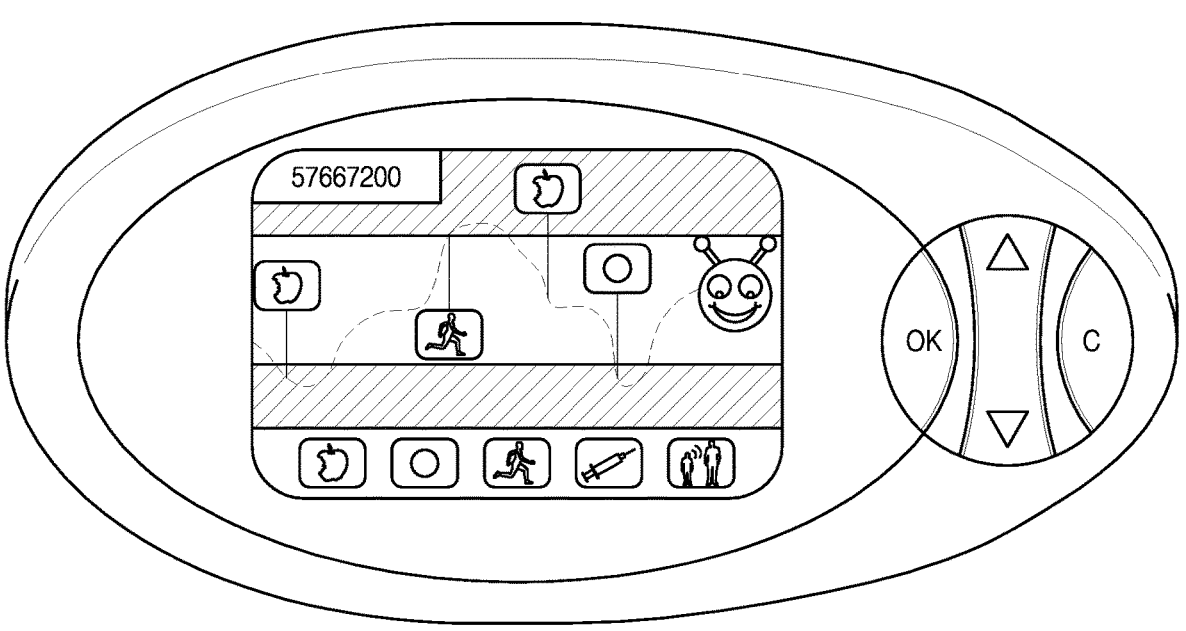

FIGS. 9A and 9B are drawings illustrating embodiments of displayed tutorial data. FIG. 9A shows tutorial data 128 representing a selected glucose scenario. Icons 130 represent eating food, eating a glucose tablet, exercising, injecting insulin, or contacting someone for help, respectively. FIG. 9B shows tutorial data with actions and results of the actions. In some embodiments, the actions are real actions taken by a user from whom measurements were taken and are included in the tutorial data. In some embodiments, at least some of the actions are actions selected within a tutorial, and the measurements shown after the actions are simulated responses to the selected actions. In some embodiments, icons such as icons 130 are used outside of a tutorial to graphically indicate actions taken by the user.

Systems and methods can also be configured to provide a diabetes management game based on simulated or sample data. These games can be run and played on a computer system such as a PC, a PDA, a mobile phone, or the receiver 12 described above, for example. One mode can be configured to cause a user to compete against the computer system, wherein the computer system makes decisions (e.g., insulin dosing decisions) based on standard bolus wizards that take into account single point glucose sensor data (e.g., from a meter or significantly time spaced sensor data by at least about 4 hours) in one embodiment or continuous glucose sensor data (e.g., from an implantable sensor) in another embodiment. Preferably, the goal of this game is for the user to achieve a good score or beat the computer system. In one embodiment, the largest contributor to the score is based on exposure to glucose; in one embodiment, it could be an A1c score derived from the area under the curve over time. Deductions from the score can occur if a player has a severe hypoglycemia episode. Low variability of glucose concentration can amplify the score. The game can be designed to be repeatedly played by the user. In this exemplary embodiment, the game does not provide help or assistance or any advice about actions to take, but the game requires the user to read only the glucose information provided by an actual continuous glucose sensor session (e.g., glucose value, trend arrow, and/or graphical time display) and make insulin dosing decisions.

In one example, the game begins with simulated and/or sample data consistent with an "out of control" patient level (e.g., high glucose variability and/or high A1c) and sequentially move toward simulated and/or sample data consistent with a "well controlled" patient level (e.g., low glucose variability and/or low A1c) as the user successfully achieves tighter glucose control (e.g., reduced exposure to glucose). For example, a defined series of levels with increasing difficulty can be provided. All players may start with an A1c of 11 or higher. Corresponding high and low settings can be 120 and 300, for example. The user successfully completing this level can mean that the user has achieved an improved A1c of, for example, 10 or 10.5, and the game gets progressively more difficult as the A1c gets lower, and the high and low limits narrow.

For example, the screen moves along at about 1 hour every few seconds and at periodic times it freezes and states a scenario (e.g., "you are about to stop at fast food restaurant for a specified meal deal. How much insulin should you take?") The user enters their estimation for insulin dosing, while the computer enters its estimation for insulin dosing based on the bolus wizard value. At the end of a prescribed period of time, the player either loses or wins against the computer. Advantageously, the user is motivated to play again and again until they beat the computer and improved the glycemic control of the simulated or sample data is revealed. In embodiments wherein the bolus wizard is based on single point glucose sensor data, it is believed that the usefulness of continuous glucose sensor data can easily be exemplified. In embodiments wherein the bolus wizard is based on continuous glucose sensor data, the simplicity and ease of use of graphical and/or trend information associated with continuous glucose sensor data can be illustrated.

In another mode, the system can be configured to cause the user to play against a physician. In this mode, the system is configured to display a retrospective data set from a sensor session (e.g., 3, 5 or 7 days of sample data) to the patient. The user is not given physician information, but instead makes insulin dosing decisions at specified events and/or time points in the data set. The computer system is programmed with physicians' instructions (from a real or sample physician). The goal of this game is to beat the physician. Advantageously, this mode raises awareness of the difficulty of analyzing data sets retrospectively, and points to the power of real time continuous glucose sensor data.

In yet another mode, the system can be configured to allow two or more users to compete. In this mode, the same simulated and sample data (real-time or retrospective) is provided to multiple users (e.g., user vs. doctor, users online, etc).

Figure 10:
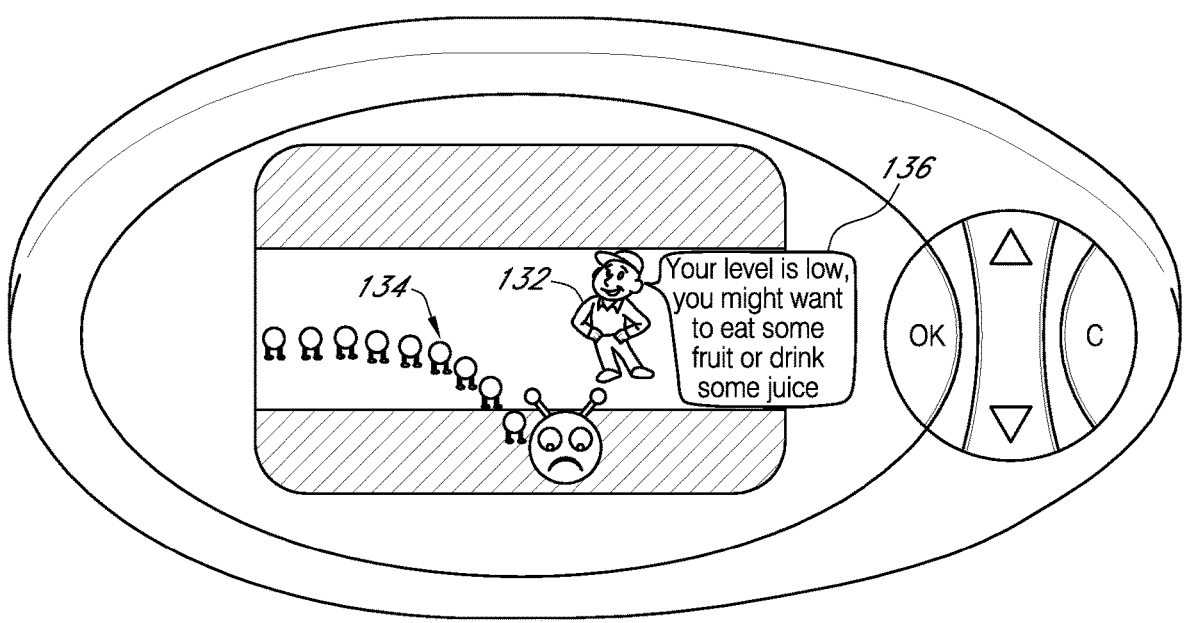
FIG. 10 is a drawing illustrating an embodiment of displaying data with a graphical character.

FIG. 10 is a drawing illustrating an embodiment of presenting information, such as sensor data or help information, in conjunction with an avatar or other graphical character. In this embodiment, a graphical character 132, such as a character that may be selected by a pediatric host (e.g., as a reward for maintaining their blood glucose level within a predetermined range over a certain time period) is displayed with sensor data 134, however, in some embodiments a graphical character is displayed without sensor data. In this embodiment, the graphical character 132 is displayed with a message 136, however, in some embodiments a graphical character is displayed without a message.

The graphical character 132 may be, for example, any of a person, a child, an imaginary creature, an avatar, an animal, or the like. In some embodiments, the graphical character 132 is a character used with other media, such as in television or movies. In some embodiments, the graphical character 132 is displayed as having supernatural abilities. The graphical character 132 may include one or more characters. In some embodiments, two or more characters are displayed as interacting with one another. In some embodiments, the graphical character 132 is selected through an input to the receiver. The graphical character 132 may include a portion or all of an uploaded pictures, such as pictures of family members, children, bucket list, etc. In some embodiments, the graphical character 132 is selected randomly or pseudorandomly from a group of selectable characters.

In the embodiment of FIG. 10, the graphical character 132 provides a message 136. The message 136 contains a therapeutic suggestion and/or motivational message in response to the sensor data 134. Other messages in response to the sensor data 134 may be used. For example, messages may include any of encouragement, congratulations, and warnings in response to the sensor data 134. In some embodiments, the message is not in response to sensor data. For example, the message may ask for input, such as requesting the user to indicate if the user has eaten lunch. The message may give a reminder to perform an action, such as to request the receiver to display sensor data from the past week. In some embodiments, the message may not be related to glucose monitoring. For example, the message may be a joke, or display the current time of day. Messages may be displayed on a display device of the receiver, may be pictoral or graphical, and/or spoken (e.g., in the voice of the character) using a speaker of the receiver.

In some embodiments, a character is displayed in response to an input by the user, such as the push of a button. In some embodiments, the character is displayed in response to another event, such as the sensor data having a specified characteristic, such as being above or below a threshold. The character may also be displayed in response to a time. The time may be programmed, or may be a random or pseudorandom time. In some embodiments, the character is used to display the sensor data, such as the centipede 134 of FIG. 10.

In some embodiments, a receiver (such as receiver 12) is configured to interface with a network to upload and/or download data. For example, using the receiver 12, the user may upload game scores, sensor data, and/or tutorial scenarios. In some embodiments, using the receiver 12, the user can download data representing games, graphics (such as graphics 70 and 72 of FIGS. 3A and 3B and graphic 82 of FIG. 3C), target graphics (such as target graphic 78 of FIG. 3B), animations (such as that shown in FIGS. 4A-4H and 5), rewards, backgrounds, sensor data, tutorial data, icons (such as icons 130 of FIGS. 9A and 9B), graphical characters (such as graphical character 132 of FIG. 10), and messages (such as message 136 of FIG. 10). The downloaded data, may, for example, be accessible only as a reward. For example, a reward may be achieved for glycemic control, where the reward allows the user or caregiver, for example, to access a network database and download a new avatar. In some embodiments, parents, doctors, and/or other caretakers of patients with diabetes may make recommendations that are provided to a particular host (or a group of hosts) in response to particular alerts. For example, the doctor of a particular pediatric patient may customize textual, graphical, audible, and/or other information that may be provided to the particular patient in view of the doctors knowledge of the patient needs, tolerances, etc.

In general, any of the above methods of data input and output can be combined, modified, selectively viewed, selectively applied, or otherwise altered without departing from the scope of the present invention. The various tasks performed in connection with processes (i.e. methods) described herein may be implemented by software, hardware, firmware, a computer-readable medium storing computer executable instructions for performing the process, or any combination thereof. It should be appreciated that the processes described herein may include any number of additional or alternative tasks. The tasks described and illustrated in the figures need not be performed in the described and illustrated order, and the processes may be incorporated into a more comprehensive procedure or process having additional functionality not described in detail herein. Moreover, the descriptions of the processes may refer to elements mentioned above in connection with FIG. 1, but it is understood that other devices and systems may be used to implement aspects of the processes.

For example, methods and devices that can be suitable for use in conjunction with aspects of the embodiments described herein are disclosed in U.S. applications including U.S. application Ser. No. 11/007,920 filed Dec. 8, 2004 and entitled, "SIGNAL PROCESSING FOR CONTINUOUS ANALYTE SENSOR"; U.S. application Ser. No. 10/695,636 filed Oct. 28, 2003 and entitled, "SILICONE COMPOSITION FOR BIOCOMPATIBLE MEMBRANE"; U.S. application Ser. No. 10/633,367 filed Aug. 1, 2003 entitled, "SYSTEM AND METHODS FOR PROCESSING ANALYTE SENSOR DATA"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE;" U.S. Pat. No. 6,931,327 issued Aug. 16, 2005 and entitled, "SYSTEMS AND METHODS FOR REPLACING SIGNAL ARTIFACTS IN A GLUCOSE SENSOR DATA STREAM"; U.S. Pat. No. 7,134,999 issued Nov. 14, 2006 and entitled, "OPTIMIZED SENSOR GEOMETRY FOR AN IMPLANTABLE GLUCOSE SENSOR"; U.S. Pat. No. 7,192,450 issued Mar. 20, 2007 and entitled, "POROUS MEMBRANES FOR USE WITH IMPLANTABLE DEVICES"; U.S. Pat. No. 6,702,857 issued Mar. 9, 2004 and entitled "MEMBRANE FOR USE WITH IMPLANTABLE DEVICES"; U.S. Pat. No. 6,741,877 issued May 25, 2004 and entitled "DEVICE AND METHOD FOR DETERMINING ANALYTE LEVELS"; U.S. Pat. No. 6,558,321 issued May 6, 2003 and entitled "SYSTEMS AND METHODS FOR REMOTE MONITORING AND MODULATION OF MEDICAL DEVICES"; and U.S. Pat. No. 6,862,465 issued Mar. 1, 2005 and entitled "DEVICE AND METHOD FOR DETERMINING ANALYTE LEVELS." All of the above patents and patent applications are incorporated in their entirety herein by reference.

The above description provides several methods and materials of the invention. This invention is susceptible to modifications in the methods and materials, as well as alterations in the fabrication methods and equipment. Such modifications will become apparent to those skilled in the art from a consideration of this application or practice of the invention provided herein. Consequently, it is not intended that this invention be limited to the specific embodiments provided herein, but that it cover all modifications and alternatives coming within the true scope and spirit of the invention as embodied in the attached claims. All patents, applications, and other references cited herein are hereby incorporated by reference in their entirety.

All numbers expressing quantities are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

What is claimed is:

1. A method of using a continuous analyte monitoring system, the method comprising:

receiving sensor data from a continuous analyte sensor worn by a patient, the sensor data indicative of glucose concentration values of the patient over a time period;

determining that the glucose concentration values fell outside of and returned to a glucose concentration range of the patient during the time period;

determining a first metric associated with the glucose concentration values falling outside and returning to the glucose concentration range during the time period, the first metric including a duration of time during which the glucose concentration values fell outside of the glucose concentration range;

determining that the first metric exceeds a first metric threshold by a first amount;

applying a first weight to the first amount that the first metric exceeds the first metric threshold;

determining a second metric associated with the glucose concentration values falling outside and returning to the glucose concentration range during the time period, the second metric including an amplitude of the glucose concentration values while outside of the glucose concentration range;

determining that the second metric exceeds a second metric threshold by a second amount;

applying a second weight to the second amount that the second metric exceeds the second metric threshold, where the second weight is different from the first weight;

determining a first type of reward for the patient using the weighted first amount and the weighted second amount; and displaying or transmitting the first type of reward to the patient.

2. The method of claim 1, wherein the second metric threshold comprises a threshold amplitude.

3. The method of claim 1, wherein the first metric threshold comprises a threshold time duration.

4. The method of claim 1, wherein the first metric comprises a percentage of time the glucose concentration values fell outside of the glucose concentration range during the time period, and wherein the first metric threshold comprises a threshold time percentage.

5. The method of claim 1, wherein the first type of reward is included in a plurality of reward types, and a second type of reward corresponds to the glucose concentration values not falling outside and returning to the glucose concentration range during the time period.

\*   \*   \*   \*   \*